US006317731B1

(12) United States Patent
Luciano

(10) Patent No.: US 6,317,731 B1
(45) Date of Patent: Nov. 13, 2001

(54) METHOD FOR PREDICTING THE THERAPEUTIC OUTCOME OF A TREATMENT

(76) Inventor: Joanne Sylvia Luciano, 45 Orchard St., Belmont, MA (US) 02478

( * ) Notice: Subject to any disclaimer, the term of this patent is extended or adjusted under 35 U.S.C. 154(b) by 0 days.

(21) Appl. No.: 09/568,762

(22) Filed: May 11, 2000

Related U.S. Application Data

(62) Division of application No. 09/045,734, filed on Mar. 20, 1998, now Pat. No. 6,063,028.
(60) Provisional application No. 60/041,287, filed on Mar. 20, 1997.

(51) Int. Cl.[7] ...................................................... G06E 3/00
(52) U.S. Cl. .................................. 706/21; 706/15; 706/52
(58) Field of Search .................................. 706/21, 15, 17, 706/45, 52

(56) References Cited

U.S. PATENT DOCUMENTS

| | | | |
|---|---|---|---|
| 4,839,822 | * 6/1989 | Dormond et al. | 706/45 |
| 5,222,194 | 6/1993 | Nishimura et al. | 706/25 |
| 5,295,197 | 3/1994 | Takenaga et al. | 382/158 |
| 5,435,324 | 7/1995 | Brill | 128/897 |
| 5,517,405 | * 5/1996 | McAndrew et al. | 706/45 |
| 5,591,588 | 1/1997 | Goldstein et al. | 435/7.1 |
| 5,598,509 | 1/1997 | Takahashi et al. | 706/20 |
| 5,701,394 | 12/1997 | Arita et al. | 706/10 |
| 5,708,591 | 1/1998 | Givens | 702/22 |
| 5,812,992 | * 9/1998 | De Vries | 706/25 |
| 5,983,211 | * 11/1999 | Heseltine et al. | 706/15 |
| 6,052,679 | * 4/2000 | Aparicio, IV et al. | 706/15 |
| 6,092,058 | * 9/1998 | Smyth | 706/10 |
| 6,185,548 | * 2/2001 | Schwartz et al. | 706/21 |

OTHER PUBLICATIONS

Lin et al, "Computer access authentication with neural network based keystroke identity verification", IEEE, pp. 174–178 Aug. 1997.*
Lin et al. "Computer support system for aneurysm treatment", IEEE, pp. 1–6 Jan. 2000.*
Quinn et al, "Remote afterloading brachytherapy: Human factors in a partially automated treatment system", IEEE, pp. 266–271, 1993.*
see attached 3 sheets.

* cited by examiner

Primary Examiner—Mark R. Powell
Assistant Examiner—Anil Khatri
(74) Attorney, Agent, or Firm—Sharon L Day

(57) ABSTRACT

A method useful for facilitating choosing a treatment or treatment regime and for predicting the outcome of a treatment for a disorder which is diagnosed and monitored by a physician or other appropriately trained and licensed professional, such as for example, a psychologist, based upon the symptoms experienced by a patient. Unipolar depression is an example of such a disorder, however the model may find use with other disorders and conditions wherein the patient response to treatment is variable. In the preferred embodiment, the method for predicting patient response includes the steps of performing at least one measurement of a symptom on a patient and measuring that symptom so as to derive a baseline patient profile, such as for example, determining the symptom profile with time; defining a set of a plurality of predictor variables which define the data of the baseline patient profile, wherein the set of predictor variables includes predictive symptoms and a set of treatment options; deriving a model that represents the relationship between patient response and the set of predictor variables; and utilizing the model to predict the response of said patient to a treatment. A neural net architecture is utilized to define a non-linear, second order model which is utilized to analyze the patient data and generate the predictive database from entered patient data.

33 Claims, 30 Drawing Sheets

Treatment specific recovery model

FIG. 3-8

$$L = \int_0^T \sum_{ik} \left( \underbrace{(X_{ik} - \hat{X}_{ik})^2}_{810} + \mu_{ik}\left(\hat{X}_{ik} - f\left(\hat{X}_{ik}\right)\right) \right) dt + K \underbrace{\sum_j P_j^2}_{820}$$

estimated — 820
actual

810

Obtain optimized parameters
- fit patient data
- train on entire recovery period
- minimize error term L
- gradient descent on parameters $L$ = Error term
$k$ = patients
$i$ = symptoms
$j$ = parameter
$x$ = data (a) Immediate Treatment Effects Table 4.1

| Prediction of Outcome from Baseline Symptoms ||||||||||||||
| Symptom | Treatment |||||||||||||
| HDRS Item | Other | Tricyclic |||||||| MAOI || SSRI | Psycho-therapy || ECT |
| | | Ami | Nor | IMI | DMI | Clo | Lev | Map | Phe | Tran | Flu | IPT | CBT | ECT |
| Severity | 5,9− | 10− | | 10−,11,16+,17+ | 1,8 | 8,13 | 3− | 3−,6+ | 17+ | | 1 | 16+ | 7 | 14− |
| Depressed Mood | 2 | 10−,15 | 4 | 10−,11 | 1,8 | 8 | | | 4 | 18+ | 1 | | | 14− |
| Feelings of Guilt | | 15 | | 11 | 1,8 | 8 | | | | 18 | 1 | | | 14 |
| Suicide | 5 | 15 | | 11 | 1,8 | 8 | | | | 18 | 1 | | | 14 |
| Insomnia: early | 2 | 15 | 4 | 11 | 1,8 | 8 | | | 12,4 | 18 | 1 | | | 14 |
| Insomnia: middle | 2 | 15− | 4 | 11 | 1,8 | 8 | | | 12,4 | 18− | 1 | | | 14 |
| Insomnia: late | 2 | 15 | 4 | 11,12+ | 1,8 | 8 | | | 4 | 18− | 1 | | | 14 |
| Work and Interests | | 15 | 4 | 11,12 | 1,8 | 8 | | | 11 | 18 | 1 | | | 14− |
| Retardation | 2 | 10,15 | 4 | 10,11,12+ | 1,8 | 8 | | | 4 | 18+ | 1 | | | 18 |
| Agitation | 2 | 10,15 | | 10,11,12 | 1,8 | 8 | | | 12,4 | 18 | 1 | | | 14− |
| Anxiety: somatic | 2 | 10,15 | 4 | 10,11 | 1,8 | 8 | | | 4 | 18 | 1 | | | |
| Anxiety: psychic | 2 | 10,15 | 4 | 10,11 | 1,8 | 8 | | | 4 | 18 | 1 | | | |
| Somatic: gastrointestinal | | 15− | | 11 | 1,8 | 8 | | | | 18 | 1 | | | 14− |
| Somatic: general | | 10,15 | 4 | 10,11 | 1,8 | 8 | | | 4 | 18 | 1 | | | |
| Genital symptoms | | 15 | | 11,12 | 1,8 | 8 | | | 11 | 18 | 1 | | | 14 |
| Hypochondriasis | | 15− | 4 | 11 | 1,8 | 8 | | | 4 | 18 | 1 | | | 14 |
| Loss of Weight (or change) | 2 | 15 | 4 | 11,12 | 1,8 | 8 | | | 12,4 | 18+ | 1 | | | 14 |
| Insight | | 15+ | | 11 | 1,8 | 8 | | | | 18 | 1 | | | |
| Diurnal variation | | 15 | 4 | 11,12 | 1,8 | 8 | | | 12,16 | 18 | 1 | | | 14 |
| Depersoneliztion and derealization | | 15 | | 11 | 1,8 | 8 | | | | 18 | 1 | | | |
| Paranoid symptoms | 2 | 15 | | 11 | 1,8 | 8 | | | | 18 | 1 | | | |
| Obsessive and compulsive | 2 | 15 | | 11 | 1,8 | 8 | | | | 18 | 1 | | | |

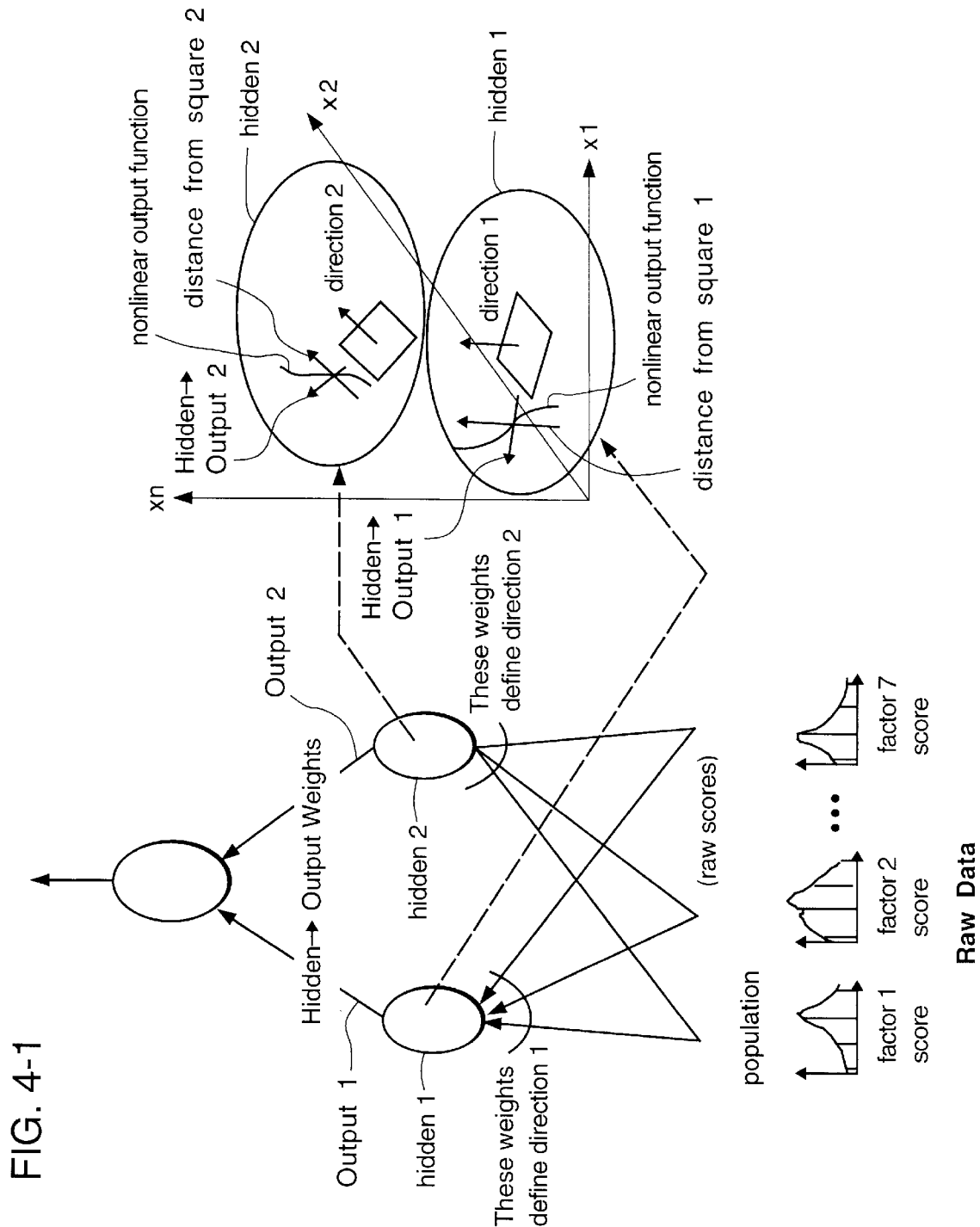

Table 4.2

1. Bowden, C., Schatzberg, A., Rosenbaum, A., Contreras, S., Samson, J., & Dessain, E. (1993). Fluoxetine and desipramine in major depressive disorder. Journal of Clinical Psychopharmacology,13, 305-311.

2. Carney, M., Reynolds, E., & Sheffield, B. (1986). Prediction of outcome in depressive illnesses by the Newcastle diagnosis scale: Its relationship to with the unipolar/bipolar and DSM-III systems.British Journal of Psychiatry.

3. Filip, V., Hoschl, C., Karen, P., Seifertova, D., Bornova, L., Praskova, H., & Prasko, J. (1993). Predicting therapeutic results with levoprotiline and maprotiline in major depression: The role of the outcome criteria. British Journal of Psychiatry, 163, 35-38.

4. Georgotas, A. & McCue, R. E., Cooper, T., Chang, I., Mir, P., & Welkowitz, J. (1987). Clinical Predictors of Response to Antidepressants in Elderly Patients. Biological Psychiatry, 22, 733-740.

5. Hinrichsen, G. A. & Hernandez, N. A. (1993). Factors associated with recovery from and relapse into major depressive disorder in the elderly. American Journal of Psychiatry, 150, 1820-18 25.

6. Hoencamp, E., Haffmans, P. M. J., Duivenwoorden, H., knegtering, H., & Dijken, W. A. (1994). Predictors of (non-)response in depressed outpatients treated with a three-phase sequential mediation strategy. Journal of Affective Disorders, 31, 235-246.

7. Johnson, S. L., Monroe, S., Simons, A., & Thase, M. E. (1994). Clinical characteristics associated with interpersonal depression: symptoms, course, and treatment response. Journal of Affective Disorders, 31, 97-109.

8. Joyce, P. R., Mulder, R. T., & Cloninger, C. R. (1994). Temperament predicts clomipramine and desipramine response in major depression. Journal of Affective Disorders, 30, 35-46.

9. Katon, W., Lin, E., Von Korff, M., Bush, T., Walker, E., Simon, G., & Robinson, P. (1994). The predictors of depression in primary care. Journal of Affective Disorders, 31, 81-90.

10. Katz, M., Koslow, S., Maas, J., Frazer, A., Bowden, C., Casper, R., Croughan, J., Kocsis, J., & Redmond Jr., E. (1987).The timing, specificity, and clinical predictors of tricyclic drug effects in depression. Psychological Medicine, 17, 297-309.

11. Kocsis, J. H., Mason, B. J., Frances, A. J., Sweeney, J., Mann, J. J., & Marin, D. (1989). Prediction of response of chronic depression to imipramine. Journal of Affective Disorders, 17, 225-260.

12. McGrath, P. J., Stewart, J. W., Harrison, W. M., Ocepek-Welikson, K., Rabkin, J. G., Nunes, E. N., Wagner, S. G., Tricamo, E., Quitkin, F. M., & Klein, D. F. (1992). Predictive value of symptoms of atypical depression for differential treatment outcome. Journal of Clinical Psycho pharmacology, 12, 197-202.

13. Nagayama, H., Nagano, K., Ikezaki, A., & Tashiro, T. (1991). Prediction of efficacy of antidepressant by 1-week test therapy in depression. Journal of Affective Disorders, 23, 213-216.

14. Pande, A., Krugler, T., Haskett, R., Greden, J., & Grunhaus, L. (1988). Predictors of response to electroconvulsive therapy in major depressive disorder. Biological Psychiatry, 24, 91-93.

15. Sauer, H., Kick, H., Minne, H. W., & Schneider, B. (1986). Prediction of the amitriptyline response: Psychopathology versus neuroendocrinology. International Clinical Psychopharmacology, 1, 284-295.

16. Sotsky, S. M., Glass, D. R., Shea, T. M., Pilkonis, P. A., Collins, J. F., Elkin, I., Watkins, J. T., Imber, S. D., Leber, W. R., Moyer, J., & Oliveri, M. E. (1991). Patient predictors of response to psychotherapy and pharmacotherapy: Findings in the NIMH treatment of depression collaborative research program. American Journal of Psychiatry, 148, 997-1008.

17. Vallejo, J., Gasto, C., Catalan, R., Bulbena, A., & Menchon, J. (1991). Predictors of antidepressant treatment outcome in melancholia: psychosocial, clinical, and biological indicators. Journal of Affective Disorders, 21, 151-162.

18. White, K. & White, J. (1986). Tranylcypromine: Patterns and predictors of response. Journal of Clinical Psychiatry, 47, 380-382.

METHOD FOR PREDICTING THE THERAPEUTIC OUTCOME OF A TREATMENT

This divisional application claims the benefit of Ser. No. 09/645,734, now U.S. Pat. No. 6,063,028 filed Mar. 20, 1998 which claims the benefit of U.S. Provisional Application Ser. No. 60/041,287 filed on Mar. 20, 1997, the disclosure of which is incorporated herein by reference.

FIELD OF THE INVENTION

A method for facilitating the selection of a treatment regime and for monitoring the outcome of a particular treatment regime on a disease based upon the expected outcome is provided. The treatment is selected from a group of possible treatments based upon the pre-treatment diagnostic data where more than one treatment regime could be selected. The method finds utility, for example, in the treatment and monitoring of disease states wherein the symptoms of the disease can result from more than one physiological condition.

BACKGROUND OF THE INVENTION

While the method of the instant invention is useful for the treatment selection for more than one type of disorder which is diagnosed and treated based upon the symptoms, for simplicity, the treatment selection for a disorder wherein the diagnosis is made by a physician based upon somatic symptoms such as for example depression and especially unipolar depression, will be discussed therein.

Recent studies suggest that in the U.S. about 6–10% of the population exhibit varying symptoms of depression which costs society billions of dollars annually. Depression is an affective metal health disorder which is diagnosed based upon descriptive criteria or somatic symptoms which are set forth in the Diagnostic and Statistical Manual of Mental Disorders (DSM-IV) (APA, 1994). The severity of the disorder is diagnosed using the Hamilton Depression Rating Scale (HDRS) (Hamilton, 1960) which is a clinical instrument devised by Hamilton which assesses the severity of the symptoms of the disorder. The instrument evaluates twenty-one psychological, physical, and performance deficits. Many different malfunctions may give rise to the same set of somatic symptoms and the physiological basis for these malfunctions is not thoroughly understood. Thus, it is difficult to determine the correct treatment regime for a patient.

In clinical research studies which are performed to assess the effect of a treatment, pre-treatment or baseline scores and post-treatment scores are typically compared. Several prior research efforts focused on the recovery pattern of depression symptoms. In 1984, Quitkin (Quitkin, F. M., et al.; *Arch General Psychiatry* (1984) 41: 782–786) analyzed the patterns of general improvement in depressed patients in response to treatment with drug therapy. He compared four antidepressant drug treatments with a placebo (N=318). The results showed that a "true drug response" was indicated by a pattern of delayed and persistent improvement. The delay was up to 4 weeks, but once improvement started it continued. These results were replicated by Quitkin et al. in 1987 (Quitkin, F. M., et. al.; *Arch. Gen. Psychiatry* (1987) 44: 259–264). They used a measurement of overall general improvement in the patient's condition (CGI: Clinical Global Impression scale).

Katz et al. (1987) (Katz, M., et.al.; *Psychological Medicine* (1987) 17: 297–309)found that specific changes in symptoms after one week of treatment were predictors of response to imipramine and amitriptyline treatments in bipolar and unipolar patients (N=104). As the symptom measure, they used "state constructs" which included HDRS as one of its measurements. According to their analysis (analysis of covariance), these measurements indicated week-one predictive symptoms to be a reduction in disturbed affects ((distressed expression and anxiety ($p<0.001$); depressed mood, hostility and agitation($p<0.01$)); and cognitive functioning ((cognitive impairment($p<0.01$)). Retardation drops only after these symptoms drop. Sleep disorder drops non-differentially from an early stage for responders and non-responders. These symptoms were the ones that dropped early and were predictive of the outcome. Sleep disorder dropped early too, but was not predictive of the outcome because it dropped both in responders and non-responders. Retardation dropped later in responders.

The advantages of time series analysis were illustrated by Hull et al. (Hull, J. W., et.al.; *Journal of Nervous and Mental Disease* (1993) 181: 48–53) in documenting the treatment effects of fluoxetine in a 58 week in-patient trial. The data analyzed were from a self-report symptom scale obtained for a single patient (N=1). Forty weeks of pre-treatment data were available for the analysis. The amount of data obtained was sufficient for time series (intervention analysis) of the time course of depression symptoms. The data before intervention was best fit by the model identified as (AR, I, MA)=(0, 1, 1). This is a first order moving average model that operates on the first degree differential of the time series data. Eight "dummy" variables corresponding to the intervention were then introduced. Each was a step function that changed from zero To one at week i after intervention (i=0, 1, . . . , 7). Most symptom scores dropped significantly during the second week. The most noticeable was depression ($p<0.001$). Some symptom scores showed additional drops by the fourth week. Psychoticism, characterized by delusions or hallucinations was an exception, in that is primary response occurred during the first week.

Recently, a method of diagnosing or confining a diagnosis of depression has been developed by Goldstein et. al. (U.S. Pat. No. 5,591,588; Goldstein et. al.; the disclosure of which is incorporated herein by reference). Based upon laboratory determined blood values of the neurohormone arginine vasopressin and on the thymic hormone thymopoietin taken from blood samples obtained in the afternoon from patients and using a logistic regression model which was confirmed using a linear discrimination analysis, this diagnostic criterion was found to be accurate in 81% of the patients who were diagnosed as depressed using Hamilton Depression Rating Scale.

The above described methods are useful for characterizing and diagnosing an affective disorder. However, assignment of a treatment based upon the diagnosis and characterization of the disorder is not achieved by these methods. Further, once a treatment is assigned to a patient based upon the currently used methods, no treatment specific recovery pattern is available to monitor the progress achieved by the patient at various time points of treatment in between pre- and post-treatment assessment.

The time resolution of the measurements is coarse. Data is collected weekly at best. Frequently data points are missing. Further, patient data gathered is rated on a five point scale and is qualitatively assessed. The population studied may not be representative of the entire range of the disorder; it may not be normally distributed in a statistical sense. In particular, the patient's progress is not compared with the pattern of recovery shown by patients who have received similar treatment regimes and who have been determined to be 'recovered' based on HDSR with respect to the time course of the disappearance of symptoms.

Several treatment regimes have proven effective in treatment depression when pre- and post-treatment are compared, but the response to the various treatments is highly variable. Within a group of patients all assessed to have the same HDSR, response to the same treatment is highly variable. Some people respond in the expected manner, while others do not. Further variability is added in that some patients response in the same manner to different treatments. These treatments include psychotherapy such as for example cognitive behavioral therapy (CBT) and/or drug treatment, such as for example with a tricyclic antidepressant drug (TCA) such as for example despiramine (DMI) or such as for example with a selective serotonin reuptake inhibitor, such as for example, fluoxetine (FLU). Each treatment has proven successful with a certain subset of patients exhibiting somatic symptoms of depression derived from the Hamilton Depression Rating Scale. However, identification of members of a subset prior to the onset of treatment is difficult. Thus, optimal treatment selection is difficult for any given individual.

Currently, once a patient is diagnosed as having the disorder, depression and the severity of the disorder is assessed using the Hamilton Depression Rating Scale (HDRS), a single total score is obtained based upon a series of somatic indicators. Using the HDRS score, the doctor selects one treatment regime from among several possible treatment regimes. The choice of treatment has been based on the absence of undesirable side effects and on the training background of the clinician rather than on the knowledge of the potential efficacy of the treatment regime for the patient. Trial and error methods of treatment assignment have proven to have met with limited success. Previous attempts at using statistical techniques to predict the outcome of treatment for depression have also proven to be weak indicators. A model with predictive value is needed to facilitate successful selection of a treatment regime for a patient exhibiting symptoms with varying severity associated with depression.

Once the patient starts treatment, monitoring of the recovery process is performed qualitatively by the physician's assessment of the patient's rate of recovery. This assessment is based upon the physician's previous experience of recovery patterns from other individual patients. However, this experience is limited. What is needed is a method for monitoring the patient's recovery with time that would allow early detection of deviation from an expected recovery path where the recovery path is derived from a larger population sample. This would provide the physician with a more accurate predictor of the outcome of treatment. By comparing the individual's response to a representative response which resulted in recovery, the physician would be provided with a more rapid way to re-evaluate the treatment, and if needed, would allow the physician to alter the treatment regime, thus facilitating patient recovery.

However, patient recovery is very idiosyncratic and highly variable. Thus, establishing predictive patterns of recovery has been thought to be unfeasible. Further, the pattern of recovery of any individual patient is thought to be too unique. Therefore, the usefulness of comparing any individual's recovery pattern with a predicted recovery pattern has been considered to have very limited usefulness. What is needed is a model which allows for variability while providing predictive value.

Due to the variability of the data and confounded by the iodiosyncratic response of patients to the assigned treatment, analysis of the data in order to assign treatment and predict the outcome to that treatment, much less monitor the patient's progress in response to the treatment so that early intervention and alteration of treatment can be achieved has proven difficult. What is needed is a system to analyze the data which provides the physician with a method to predict and monitor outcome of treatment.

It is an object of the instant invention to provide a method for standardizing the assignment of a treatment for a disorder, such as for example, depression.

It is a further object of the instant invention to provide a method for monitoring the effectiveness of an assigned treatment for a disorder which is diagnosed and monitored based upon symptoms assessed at various time intervals.

It is an additional object of the instant invention to facilitate more timely intervention by the physician with respect to treatment choice when treatment is not progressing as expected.

SUMMARY

The invention relates to a method useful for facilitating choosing a treatment or treatment regime and for predicting the outcome of a treatment for a disorder which is diagnosed and monitored by a physician or other appropriately trained and licensed professional, such as for example, a psychologist, based upon the symptoms experienced by a patient. Unipolar depression is an example of such a disorder, however the model may find use with other disorders and conditions wherein the patient response to treatment is variable.

Further, the method provides a modeling system for generating the expected recovery pattern of a patient receiving a particular treatment which is useful for comparison with the actual recovery pattern of the patient to provide for monitoring of the patient's response. The expected recovery pattern is particularly one that has been generated by the recovery model of the instant invention. When the patient's response does not correspond to the predicted recovery pattern, the treatment regime can be re-evaluated.

The preferred recovery model is a non-linear, second order neural network model for analyzing data to generate expected outcomes from a plurality of individual patterns of response. A data system which integrates individual responses, and through analysis by the model, provides a generalized expected pattern of outcome in response to the treatment when a particular pattern of symptoms is exhibited is also provided.

A processing unit that weights the inputted patient data is provided. The weight depends upon the strength of the effect. At each point in time each unit of data has an activation value. The activation value is passed through a function to produce an output.

Each patient's recovery pattern is represented by a second order differential equation. The recovery pattern characteristics are represented by three parameters: latency (change with time) or when patient response begins within a six week treatment regime; interaction effects or how each of seven symptoms influence each other; and treatment effects or how each treatment effects each symptom. Symptoms are simplified for analysis and include parameters early sleep; middle and late sleep; energy; work; mood; cognitions; and anxiety. Responders are defined as those patients who exhibit an improvement of greater than 50% during the treatment period.

The recovery model takes into account latency, treatment effects, and the interaction of the treatment effects. Time to response is also modeled. The model is trained to optimize the parameter values. The model output which is based upon the estimated parameters and the pretreatment symptoms, is compared to the desired patient data over a six week period of time on a day by day basis. The parameter estimates are adjusted so that the difference between the model output and the patient data decreases. This process is repeated until the parameters are optimized and thereby yield a model and output that best fit the patient data.

The model can gain additional accuracy and precision through entry of additional patient data which is integrated into the model. Increased precision can be achieved by collecting patient data on a continuous basis from clinical studies and from physicians and psychologists, inputting the data, and updating the model. Thus, in an aspect of the invention, a method is provided for integrating data to provide treatment patterns that have greater predictive value than that typically available to an individual physician.

Further, a method is provided for comparing individual patient response to a predicted outcome, thereby allowing the physician the ability to monitor the patient's response with time and to assess whether or not the treatment is resulting in the expected improvement in the disorder. When the expected improvement is not observed, the physician then can intervene and alter the treatment.

Additionally, the invention provides a method for inputting data from patients, integrating that data into a data system to modify the expected recovery pattern for a particular symptom set and for a particular treatment or treatment regime and thereby provide a predictive pattern of recovery for individual patterns of symptoms and responses to treatment that has greater predictive value.

BRIEF DESCRIPTION OF THE DRAWINGS

FIG. 3-2 illustrates a flow chart for a training cycle for training a model on actual patient data.

FIG. 3-3 illustrates an overview of a recovery model and the parameters used therein.

FIG. 3-4 illustrates the annotated second order differential equation used to model the pattern of recovery.

FIG. 3-5 illustrates latency modeling.

FIG. 3-6 illustrates direct effects and interactions of the recovery model.

FIG. 3-7 provides an over view of the training process.

FIG. 3-8 provides a schematic description of an equation useful for training the model.

FIGS. 3-9A and 3-9B illustrate predicted patterns of recovery vs. actual patterns of recovery based upon two different modeling systems.

FIGS. 3-10A, 3-10B, 3-10C, and 3-10D illustrates individual patterns of recovery for four patients, wherein patients a and b receive CBT and patients c and d receive DMI.

FIGS. 3-11A and 3-11B illustrate respectively predicted and actual patterns of patient data based upon the mean values.

FIG. 3-12 illustrates mean half reduction time based upon the model's predicted values of latency for individual symptom factors.

FIG. 3-13 graphically illustrates the predicted CBT and DMI temporal response sequence of symptom improvement in patients diagnosed as having depression.

FIGS. 3-14A and 3-14B illustrate a comparison of the model's predicted immediate and delayed direct effects of treatment on symptoms for CBT and DMI treatment.

FIG. 3-15 graphically illustrates a representation of the sequence of symptom factors in recovery with CBT treatment for the second order model system.

FIG. 3-16 graphically illustrates a representation of the sequence of symptom factors in recovery with DMI treatment for the second order model system.

FIG. 3-17 graphically illustrates a sequence and casual relationship among patterns of recovery.

FIG. 4-1 graphically illustrates nonlinear mapping of back propagation.

FIG. 4-2 provides a schematic representation of the effect of normalizing transformations on reducing nonlinearity of score-to-output relationships.

DESCRIPTION OF THE BEST MODE OF THE INVENTION

Factors for analysis of recovery patterns were selected from the Hamilton Depression Rating Scale (HDRS). Three types of factors, physical, performance and psychological, were included. Generally described these factors include: early sleep; middle and late sleep; energy; work performance; mood; cogitions; and anxiety. General methods useful for statistical tests for verification of the modeling efforts as modified for use with a neural net model which correct for over-fitting are described by Luciano (Luciano; U.S. Provisional Patent Application Ser. No. 60/041,287, filed Mar. 21, 1997). Also described therein are time series prediction verification methods to validate results obtained and outcome prediction verification methods.

Figure 1A:
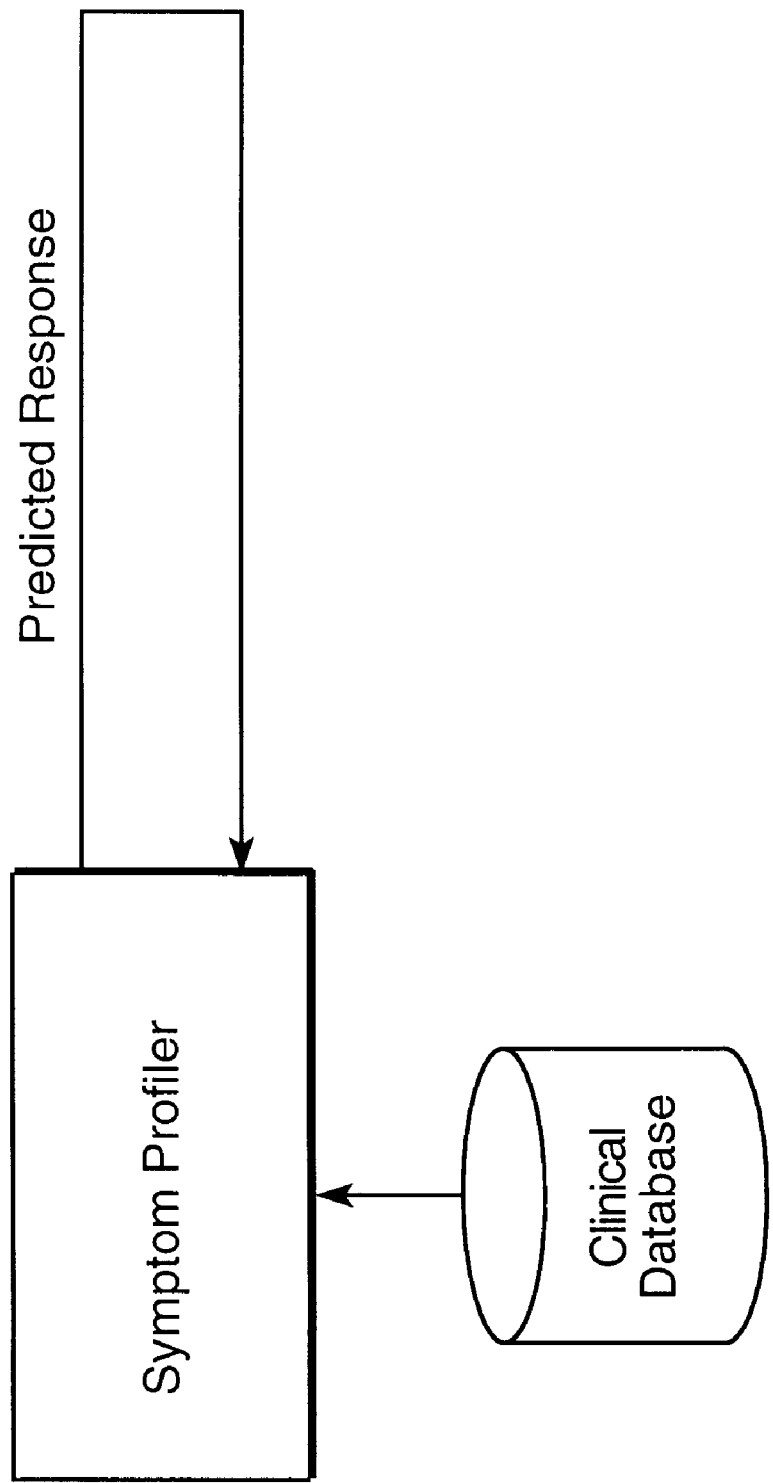
FIG. 1A illustrates a flow chart for a prototypical symptom profiler.
Figure 1B:
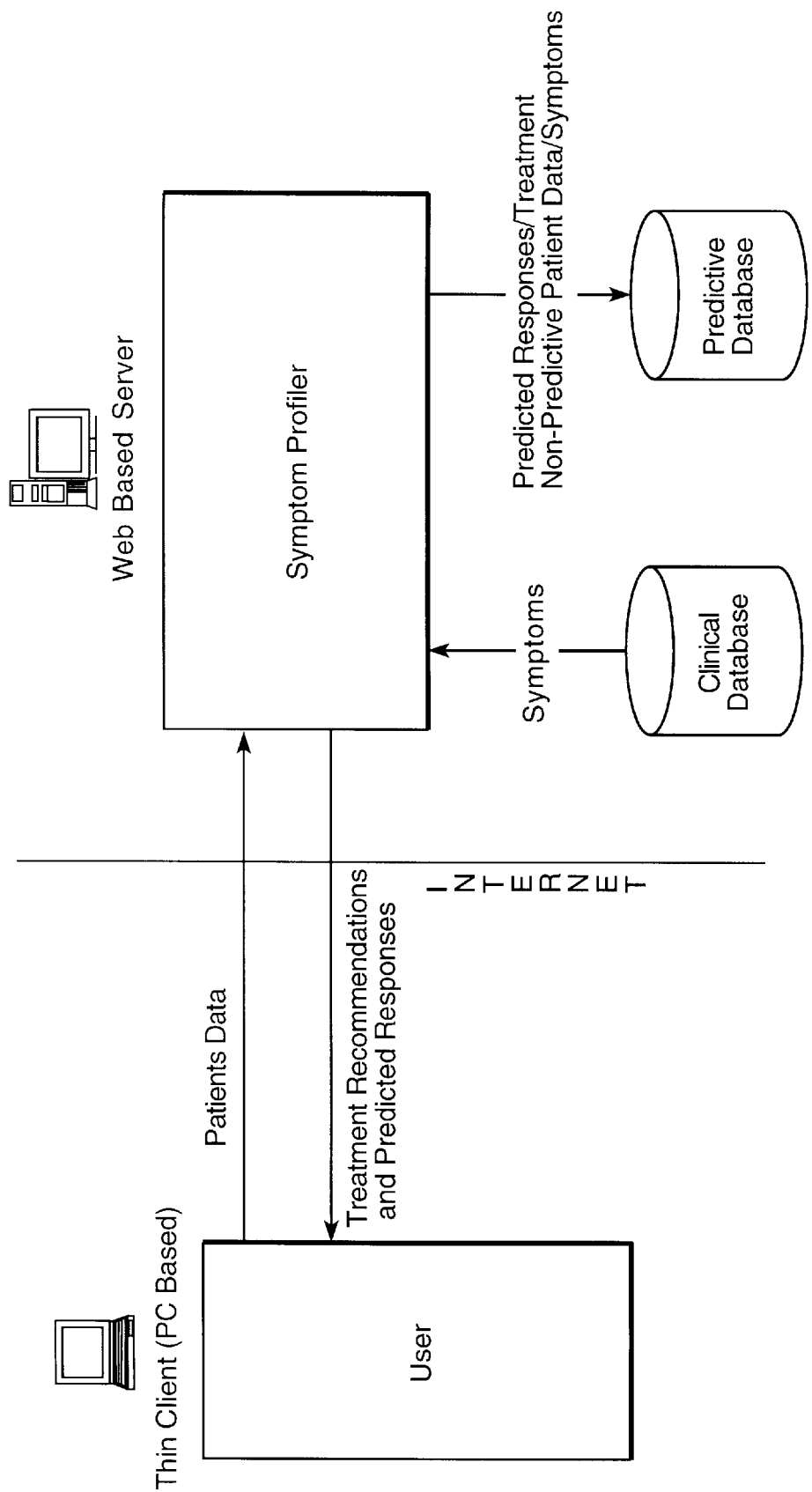
FIG. 1B illustrates a flow chart system architecture for Phase I.
Figure 1C:
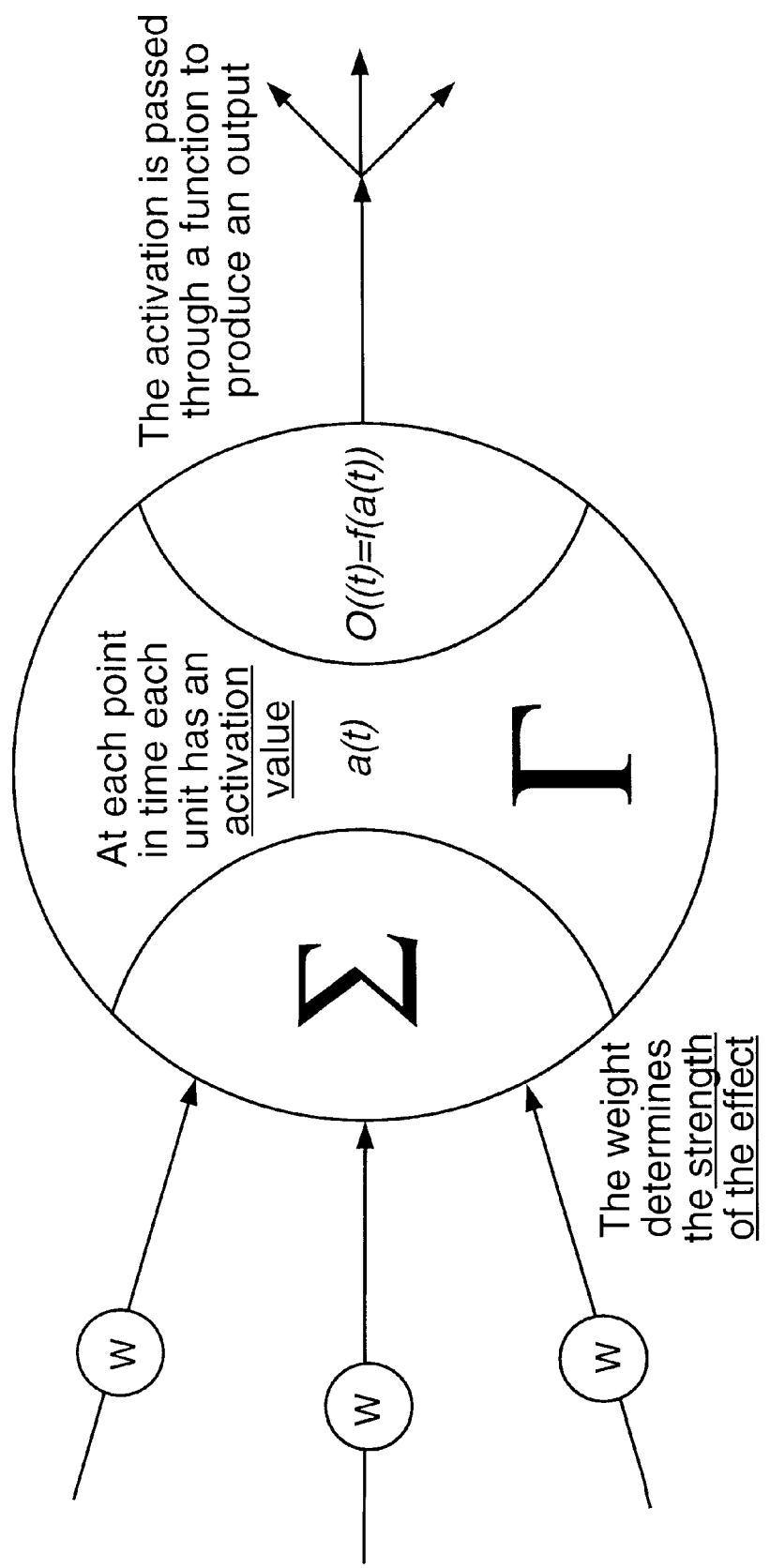
FIG. 1C illustrates a flow chart for a patient data processing unit.

Referring now to FIGS. 1A and 1B, a symptom profile developer and a system architecture for Phase I, (idealized profile development), respectively are illustrated. FIG. 1$a$ provides an overview of the development of the symptom profiler. A prototypical system is developed to provide expected or so-called idealized profiles or patterns of symptoms over time in response to a selected treatment regime. These patterns are based upon actual clinical data derived from individual patient response to a selected treatment. Clinical data are input from multiple sources. The data are pre-processed and undergo statistical tests as is illustrated in FIG. 1C, tests are standard and some are modified according to the methods described in detail below. The data are processed until the profiles are optimized on the data available at that time to create a trained symptom profiler. Completion of the training process of the system is then assessed based upon optimization of the preprocessed steps. In FIG. 1B, an overview of how the system can be used and modified to further optimize the system for providing treatment recommendations and predicted responses is presented. The trained system profiler contains a database of predicted responses. A user, such as for example a physician, enters patient data, such as for example via a computer, to the trained symptom profiler and receives a treatment recommendation and a profile of predicted responses to that treatment. Access to the trained symptom profiler optionally is through the Internet. Further, individual patient data and data from clinical studies may be input to the symptom profiler for on-going training of the symptom profiler. profiler.

Figure 2:
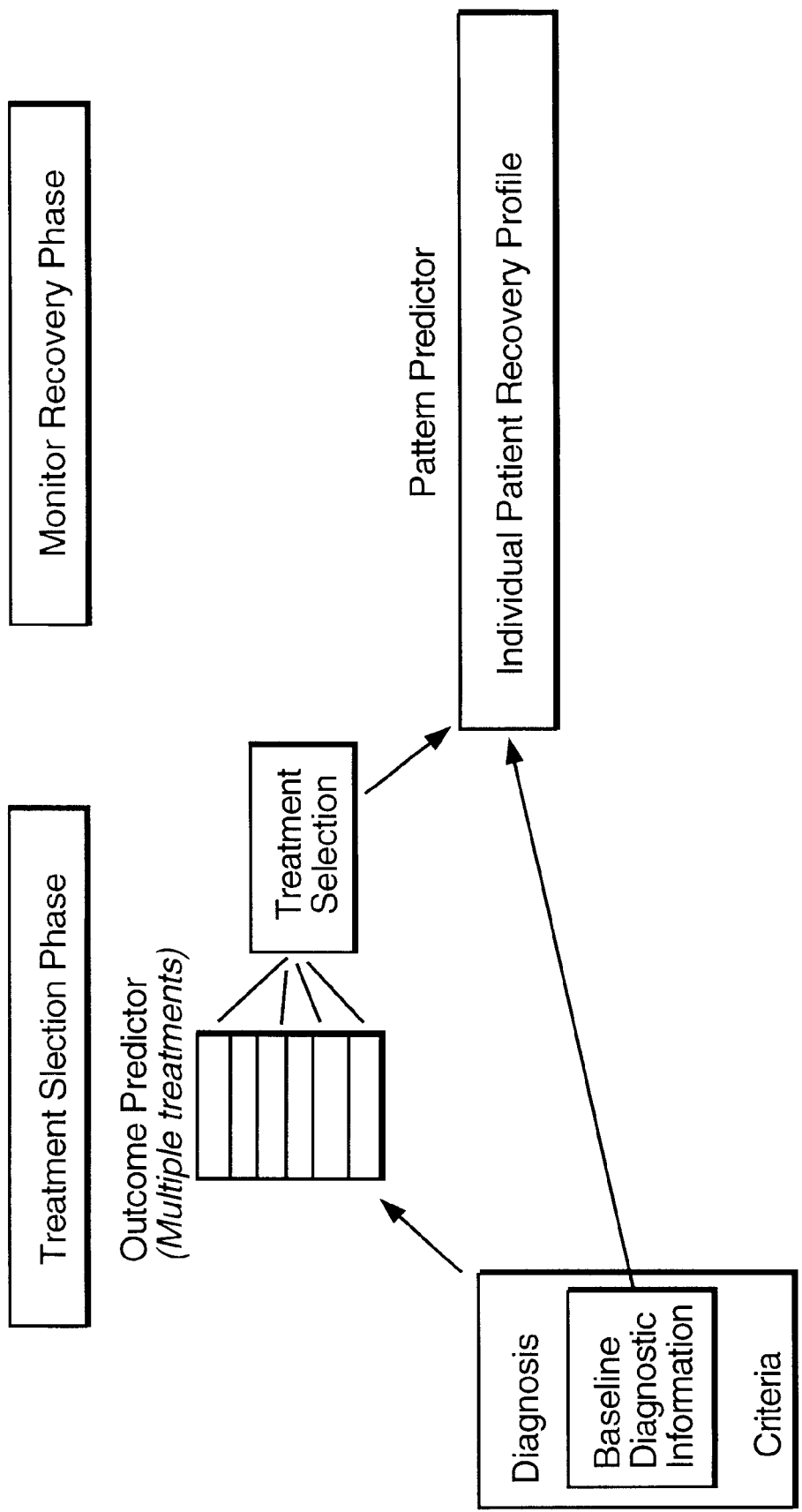
FIG. 2 illustrates a flow chart for a depression disorder integrated model.

Referring now to FIG. 2, a flow chart of a depression disorder integrated model (DDIM) is illustrated. After depression has been broadly diagnosed using DSM-IV, data are gathered from the patient using an instrument based upon the Hamilton Depression Rating Scale which is described below. During the treatment selection phase, these data are entered into the Outcome Predictor which provides a database of predicted outcomes in response to multiple treatments by comparing the patient's data to predicted outcomes based upon the information in the trained Outcome Predictor. The physician uses this information to choose the treatment most likely to produce the desired results, i.e. improvement in symptoms of depression. The physician monitors the patientOresponse to treatment and compares that response to a predicted response generated by the trained Pattern Predictor. When the patient's respond deviates from the expected response, the physician may alter the treatment regime assigned to the patient being treated.

How the symptoms of depression as assessed by the Hamilton Depression Rating Scale (HDRS) change over time in response to treatment was studied to provide detailed patterns of recovery over time. A series of analyses of two groups of patients who responded to a particular treatment regime was performed. One group of six patients responded to treatment with despiramine (DMI), an antidepressant drug medication, and the other group of six patients responded to treatment with cognitive behavioral therapy (CBT), a psychotherapy treatment. The detailed patterns of recovery in each of these patient groups were studied and modeled using systems of ordinary differential equations. This method revealed new information about how the symptom response patterns differ across treatments.

A direct approach to fitting more than one patients' recovery data over time has not been previously attempted. The problems which must be overcome are the high level of noise and the inter-subject variation in recovery. Also lacking is a detailed model which uses the subjects initial data as a starting point. The instant invention describes a differential equation model which partially deals with this problem. Another problem has to do with the large amount of variance that remains after the best fitting model is constructed. Some of this variability is unavoidable and is due to defects in the measuring instrument. The model is shown to capture a significant part of the variance of the subjects data.

The statistical reliability of the model's predictions over the two patient groups in recovery is demonstrated. From this model which is based upon a database comprised of data points gathered from assessment of individual patients over time, clear predictions as to the timing of recovery within and between treatments can be made which can be further validated and extended by additional research data inputting into the database.

To understand and explain, rather than just describe how treatments affect recovery as has been done, more detail about the pattern of recovery than previously described was sought. This meant to build upon the pattern of drug response that Quitkin, et al.(Quitkin, F. M., et al.; *Arch General Psychiatry* (1984) 41: 782–786;;Quitkin, F. M., et.al.; *British Journal of Psychiatry* 163 (suppl. 21): 30–34) described by following specific symptoms over time rather than a single indicator of global improvement. It also sought to connect the snapshots described by Katz (Katz, M., et.al.; *Psychological Medicine* (1987) 17: 297–309) and show how they relate to outcome. To do this, a sample of patients who responded to treatment was selected, and then a set of quantitative rules which describe the evolution of symptoms during recovery was estimated. Thus the resultant model is able to predict the detailed pattern of recovery from the pre-treatment symptoms. The fit of the model to the data is described in Section Qualitative Reasons for Choice of Second Order System. This work also extended the work of Hull et.al. (Hull, J. W., et.al.; *Journal of Nervous and Mental Disease* (1993) 181: 48–53) in that we had a larger sample of patients. In Hull, each symptom was modeled independently as an ARIMA process, not allowing for interactions among symptoms. Interactions of symptoms were allowed for, which enabled a more detailed analysis of the recovery sequence.

METHODS
Models of Patient Group Response Over Time

Much of individual pattern of recovery appears predictable from the subjects' initial data even though there is considerable idiosyncratic variation from subject to subject. In order to capture the maximum amount of individual variation within a treatment group as possible, and to compare the differing responses across groups, the problem was defined: Are there any differences in how symptoms improve in depressed patients who respond to cognitive behavioral therapy vs. those who respond to desipramine? The approach taken was to recast the problem as a dynamic system. Recovery patterns for patients were modeled using differential equations, wherein the differential equation parameters were specific to a treatment group. A comparison of the features of recovery patterns was made to examine latency of response to treatment. A determination of which symptoms were the first to respond to treatment was made. Further, whether or not the symptoms affect each other was evaluated. Then, statistical analysis was applied to determine the significant differences in the model predicted recovery pattern features found in the different treatment groups.

Figures 2, 3:
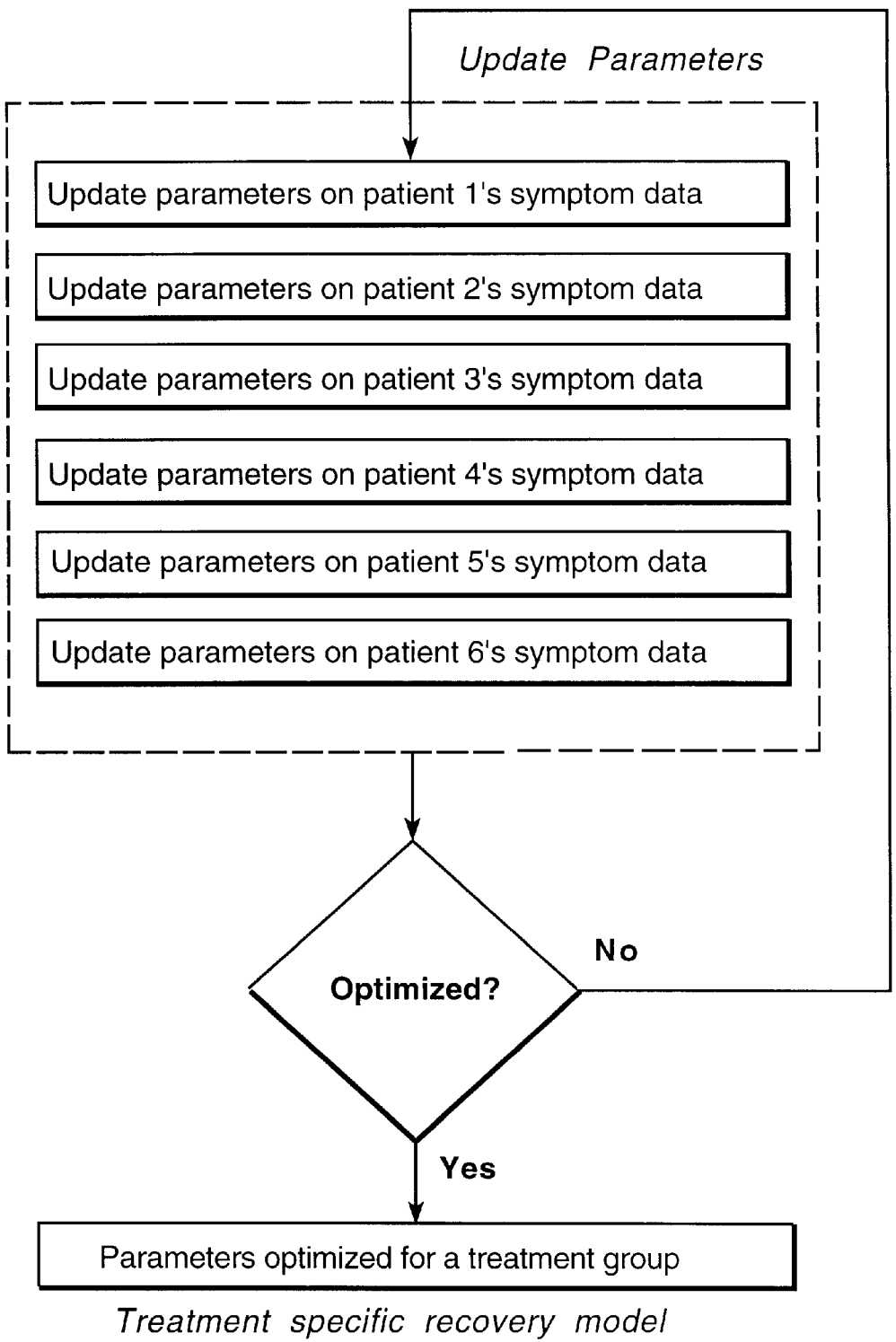
Figure 3:
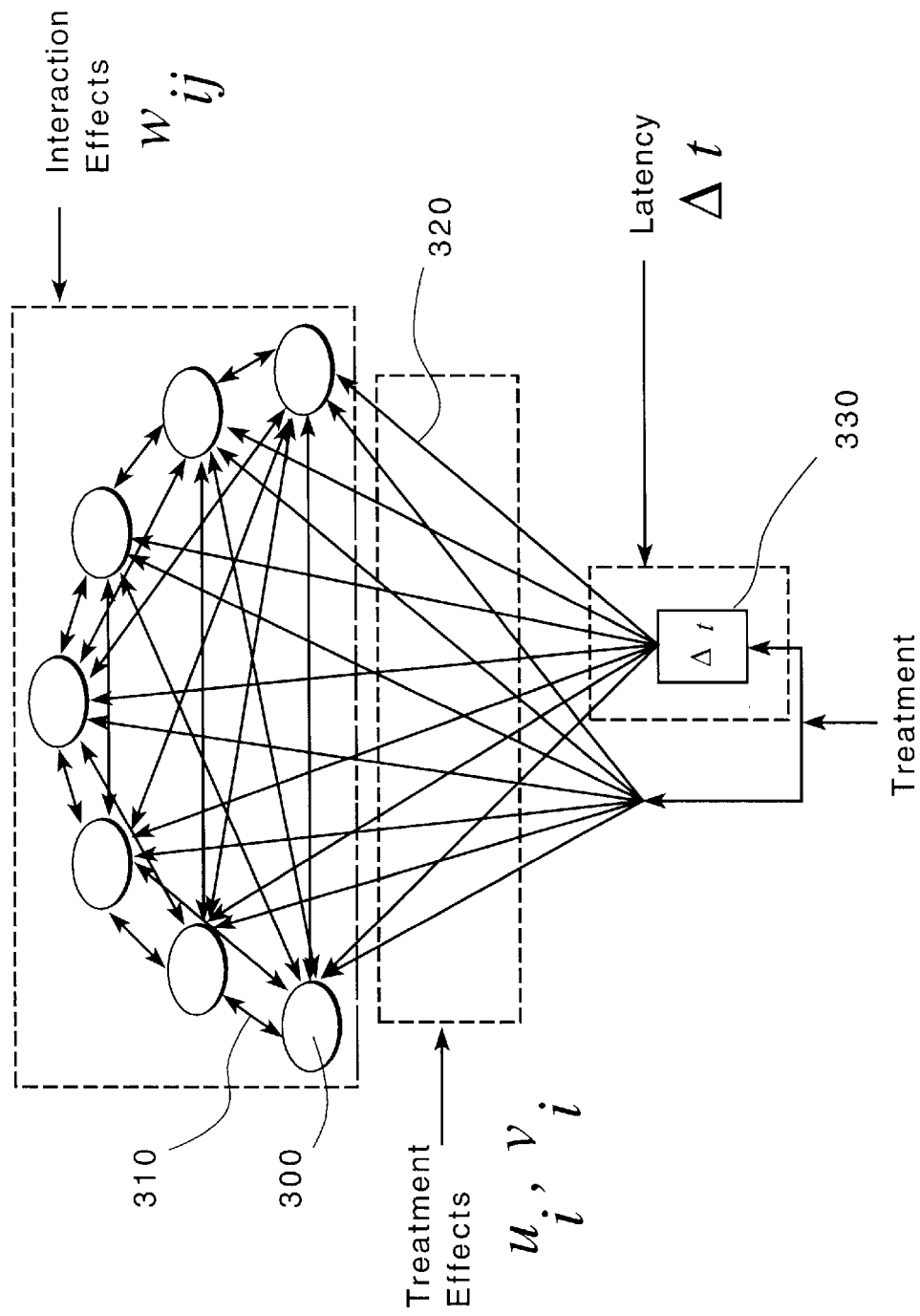

To accomplished this, an architecture or network of connections among variables corresponding to symptoms and the treatment input was constructed. Then two separate types of models of this architecture, namely a shunting model and a second-order model, so named because of the kind of differential equations that define the model, were constructed. Then, for each of these two types of models, the data were used to estimate a different set of parameters for each treatment group, DMI and CBT. Thus, parameters were estimated for four separate models (two treatment groups by two model types). The parameters were estimated iteratively by cycling through the individual data within the treatment group as shown in FIG. 1*b* and FIG. 3.2 which describes the training cycle for each treatment group. Referring to FIG. 1*b*, for each of the two different models, the same architecture but different separate parameter sets were provided. Each model was trained by cycling through individual data within the respective treatment group. After each cycle, the cost function which reflects the degree of fit of the model predictions to the actual data was evaluated to determine the completion of training. Finally, we analyzed the parameters and behavior of the trained models when initialized with individual patient's baseline data values. In this way, the reliability of the predicted behavior within the across treatment groups was quantified.

Each model was fit to the seven constructed symptom factors derived from the Hamilton Depression Rating Scale. Three primary characteristics of the response pattern were studied: (1) direct effects (from treatment to symptoms); (2)

interaction effects (between pairs of symptoms, which are indirect because they are not directly caused by the treatment); and (3)latency, which is the average time that elapses, from the start of the treatment to a 50 percent improvement in the symptoms.

Each model was designed so that its output could be easily related to the evolving symptom factor values. To accomplish this, the network architecture was specified to have one variable for each of the seven symptom factors under study. The direct effects of treatment and the interactions among symptoms were represented as modifiable connections from treatment to symptom factor variables and between the symptom factor variables. In addition to the above, a latency variable was introduced to represent varying symptom response time (the time it takes for symptoms to respond to treatment).

Differential equations were used to describe the dynamics of the model. Two systems of differential equations were studied. One was a second order linear system, the other was a shunting system—(Grossberg, S.; *Studies of Mind and Brain* (1982), D. Reidel, Dordecht, Holland) based on a first order non-linear differential equations.

After the architecture for the model was constructed, parameters were estimated using the learning algorithm described in Section Training Procedure which was adapted from optimal control theory. The optimized models are compared for goodness of fit. The parametric differences in latency, treatment effects (both immediate and delayed), and interactions between symptoms are discussed.

Patient Data

Weekly patient data were linearly interpolated to yield daily data for training. Data were converted to z-scores as follows according to Equation 1.

$$O_i = \frac{(O_i' - \overline{O'})}{\sigma(O')}$$ Equation 1 where $O_i$'s are daily training data, sigma is the standard deviation, O is the overall sample mean and sigma is the overall sample variance. The difference from each day to the next day was used as the training data for the first derivative of each day. For the last day, the first derivative was assumed to be the same as that of the previous day.

Based or the premise that the symptoms are at equilibrium before the onset of treatment, seven days of data were added before the beginning of treatment. The training data for these added data (week-1 to week 0), were set to the pre-treatment (baseline) values. For this period, training data for derivatives were set to zero.

Data from five weeks were used in the calculation of the F statistics because the first week was used as the initial value.

In addition to linear interpolation, splining by third order polynomial was also considered. It was not adopted because it tended to create artifacts that manifested as large curvatures around endpoints that potentially would distort the fit.

Assumptions of the Model Design

Several assumptions were made to highlight behavioral aspects of the effect of different treatments on and among the symptoms of depression. These assumptions apply to both the first and second order models.

Treatment Effect

The first assumption was that treatments act directly on symptoms, possibly by affecting neuromodulatory pathways acting on brain regions that control the behavior manifested in the symptom. In both models, this effect corresponds to the direct effect weights, i.e. the strengths of the response in the pathway from symptoms to treatment. Other possible causes, such as spontaneous recovery, specific fluctuations of symptoms, life events, and anticipatory anxiety about treatment termination, were not considered. Note that for both models, the symptoms tended to converge to baseline levels which represented pre-treatment symptom scores rather than non-depressed normal levels in the absence of treatment. Spontaneous recovery,i.e., recovery that may be due to lifestyle changes, supportive environment, or other uncontrolled life events were not considered for this model.

Latency

The second assumption was that there are two components of the direct treatment effect described above. One component acts directly on the symptoms, referred to as immediate and the other reflects underlying processes that cause a delay in the response, referred to as delayed or latent. Latency was included in the model because it has been observed in antidepressant drug response (Quitkin, F. M., et al.; *Arch General Psychiatry* (1984) 41: 782–786; Quitkin, F. M., et al.; *Arch Gen. Psychiatry* (1987) 44: 259–264) and was an open question for CBT response. Latency is modeled by a parameter of the transfer function of an idealized node. This node transforms elapsed time (linear) into an overall latent effect (nonlinear). The latency is assumed to be the same across all factors. The latency determines the time when the level of input (which linearly increases with the treatment duration) which results in half of the maximum possible output.

Interactions

The third assumption was that symptoms affect other symptoms, possibly through interconnections among regions such as transcortical connections, and through environmental and metabolic feedback in response to the behavioral changes. This effect is modeled by the coefficients (weights) of the links among symptom nodes.

Network Architecture

An overview of the architecture for both recovery models is shown in FIG. 3-3. It is independent of the treatment data and was used as the architecture for both first and second order systems on the CBT and DMI data. The intensity of each symptom (it's HDRS score) is represented by network nodes which are shown as ellipses and are generally referenced as 300. These correspond to the activities levels of the nodes $(x_I)$ in the system of differential equations, which describes the behavior of the network shown in FIG. 3-4 and discussed below. Treatment direct effects and interactions among symptom correspond to weighted connections (arrows, 320) in FIG. 3-3. The bi-directional arrows 310 in FIG. 3-3 represent two separate weighted connections. The overall latency of the response to treatment corresponds to the parameter (Æt) of the delay node transfer function (the rectangle 330 labeled Æt).

Figures 3, 4:
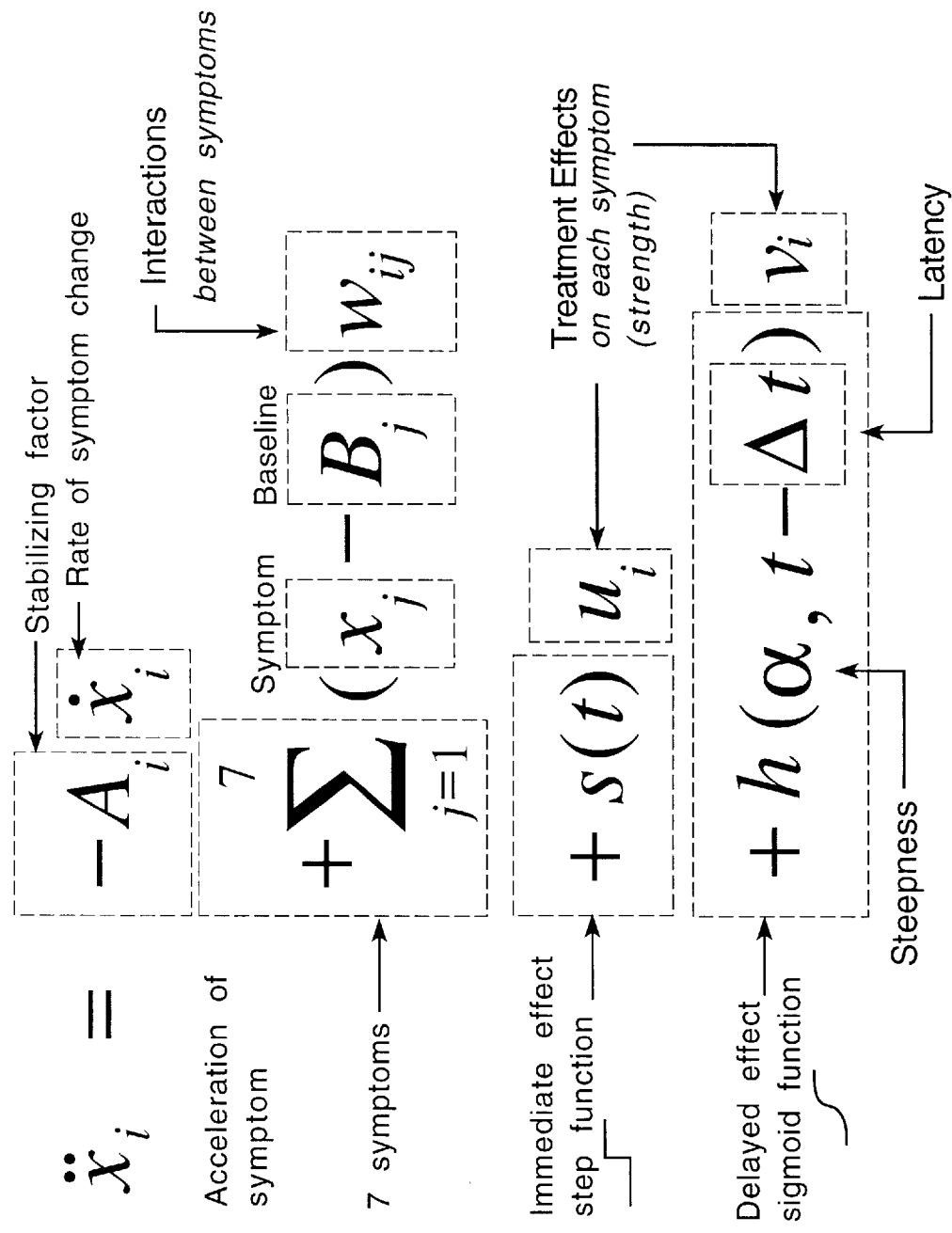

Looking now at FIG. 3-4, an annotated second order differential equation used to model the pattern of recovery is illustrated. The acceleration of symptom is equal to the summation of a stabilizing factor times the rate of symptom change plug the summation of the interactions between symptoms and the treatment effects, both immediate effects which are represented by a step function and delayed effects which are represented by a sigmoid function. The connection weights (coefficients in the equations) in the architecture represent the strength of the direct treatment intervention effects ($u_I$ for immediate effect, $v_I$ for latent effect) and the strength of the interactions between pairs of symptoms ($w_{ij}$). As in FIG. 3-3, the overall latency of the response to treatment corresponds to the parameter ($\Delta t$) of the delay node transfer function which in turn corresponds to the delay node function h ($\delta$, t–$\Delta t$) in FIG. 3-4.

Treatment Effect

The direct effects of the treatment on the symptoms are called the treatment effects. The intensity of the effect corresponds to the value of the coefficient of the link from a treatment to a symptom factor. A direct effect is inferred for symptoms whose recovery is strongly effected by the treatment intervention.

In the second order model, it is assumed that the immediate direct effect of treatment, represented by a step function, correlates linearly with the acceleration (either by an increase or reduction) of factors through immediate treatment effect coefficients. It is also assumed that the latent direct effect of treatment, represented by a sigmoid function of time, correlates linearly with the acceleration of the factors through the latent treatment effect coefficients.

Latency

Figures 3, 4, 5:
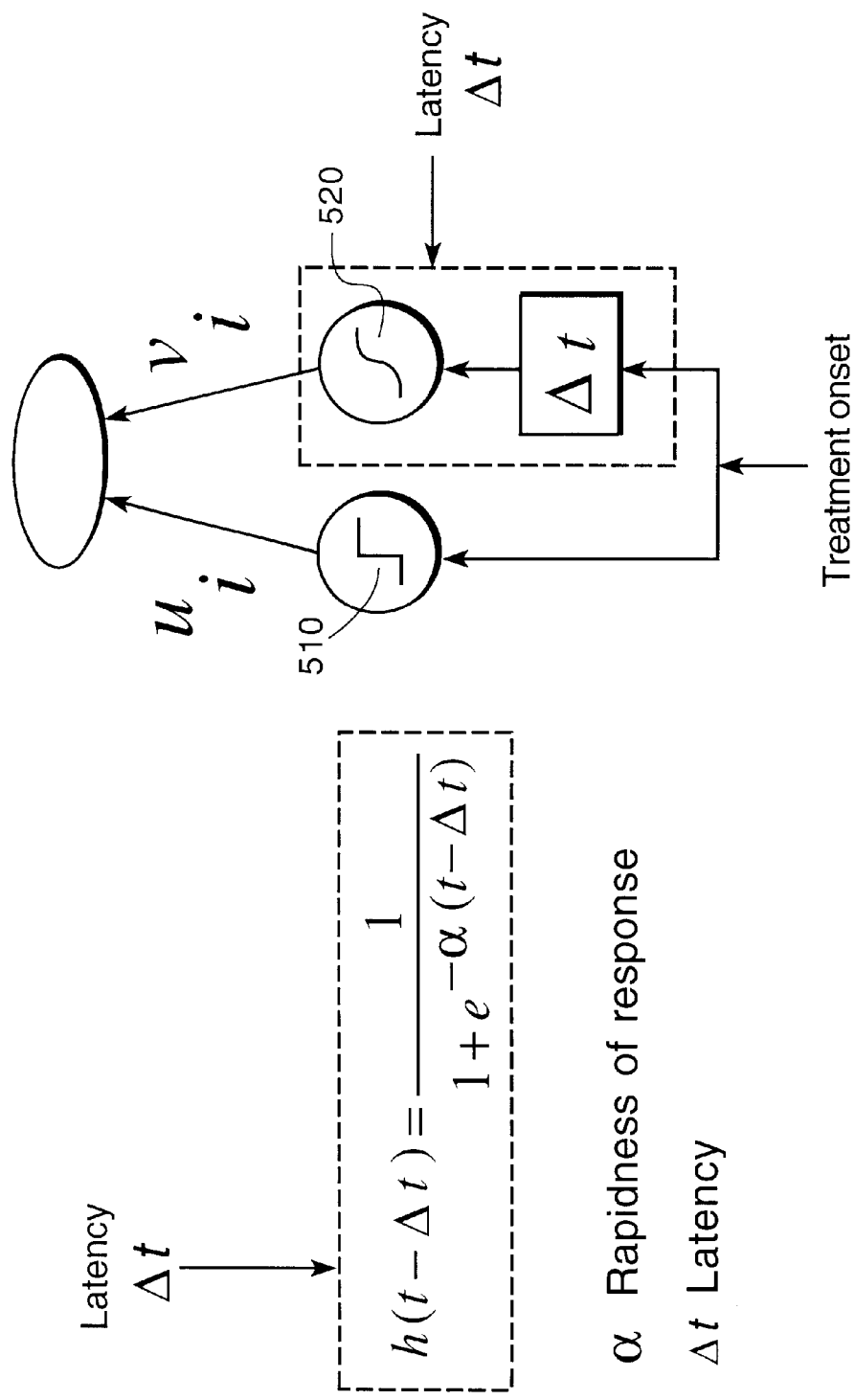
Figures 3, 4, 5, 6:
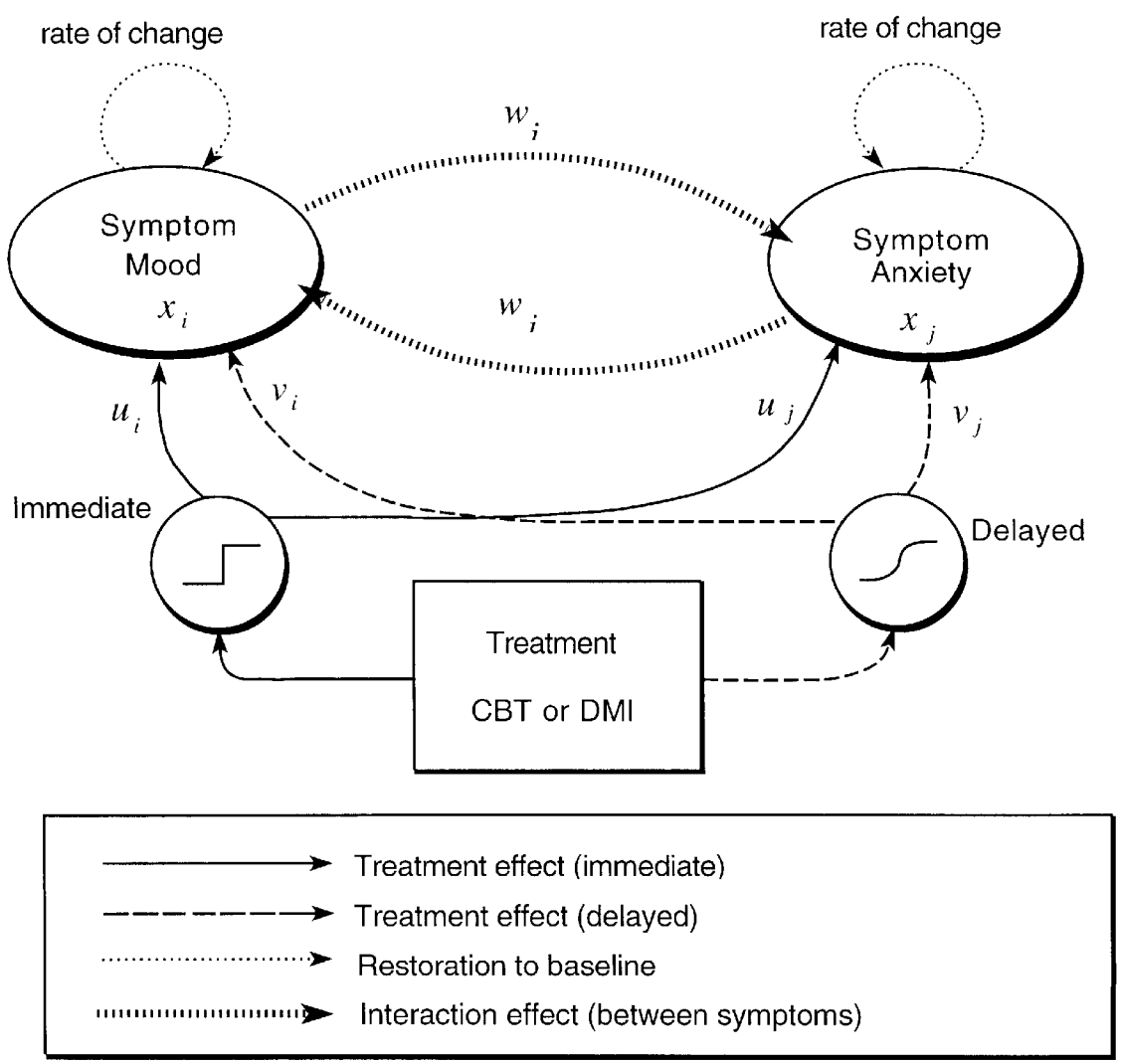
Figures 3, 4, 5, 6, 7:
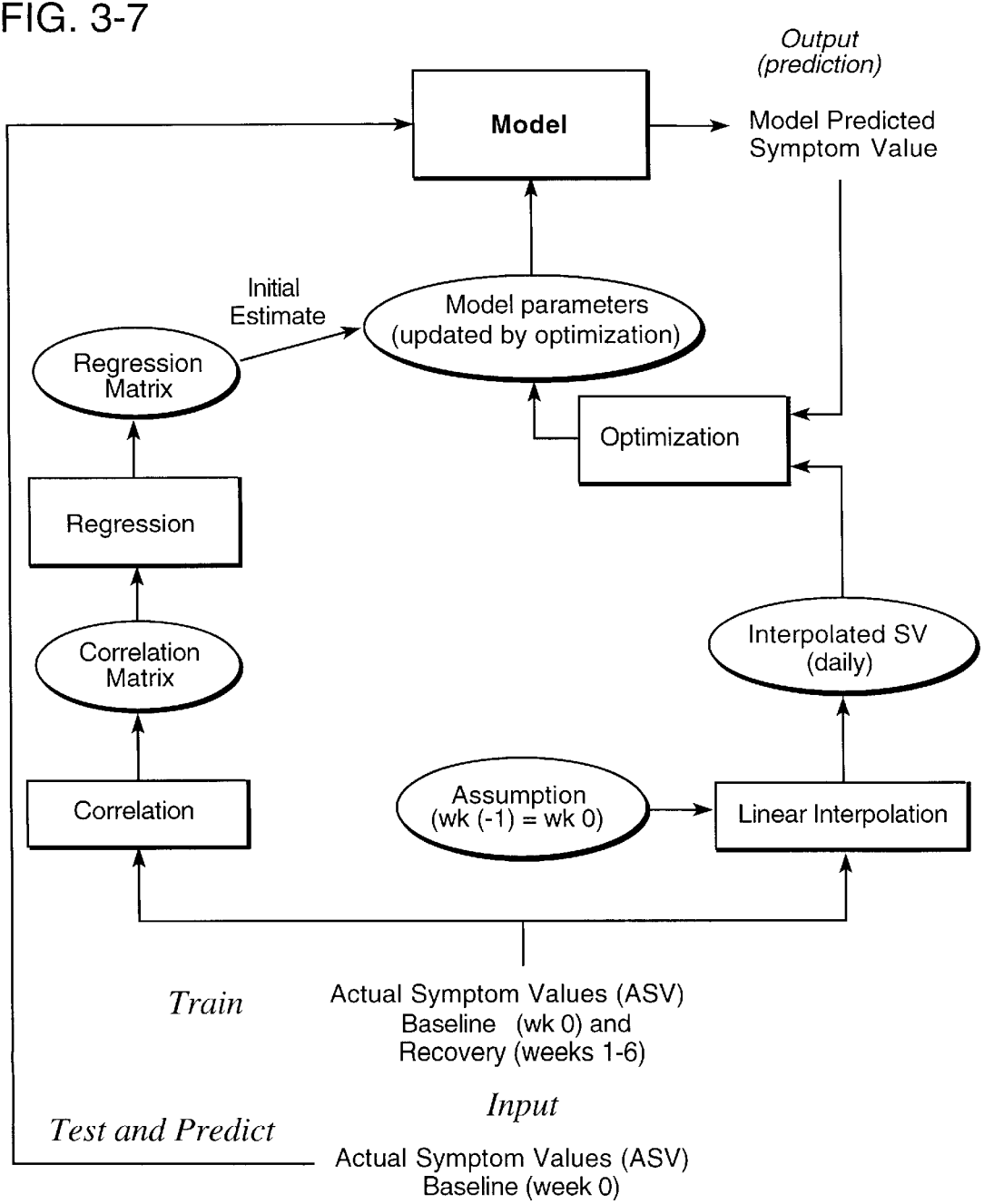
Figures 3, 4, 5, 6, 7, 8, 9, 9A:
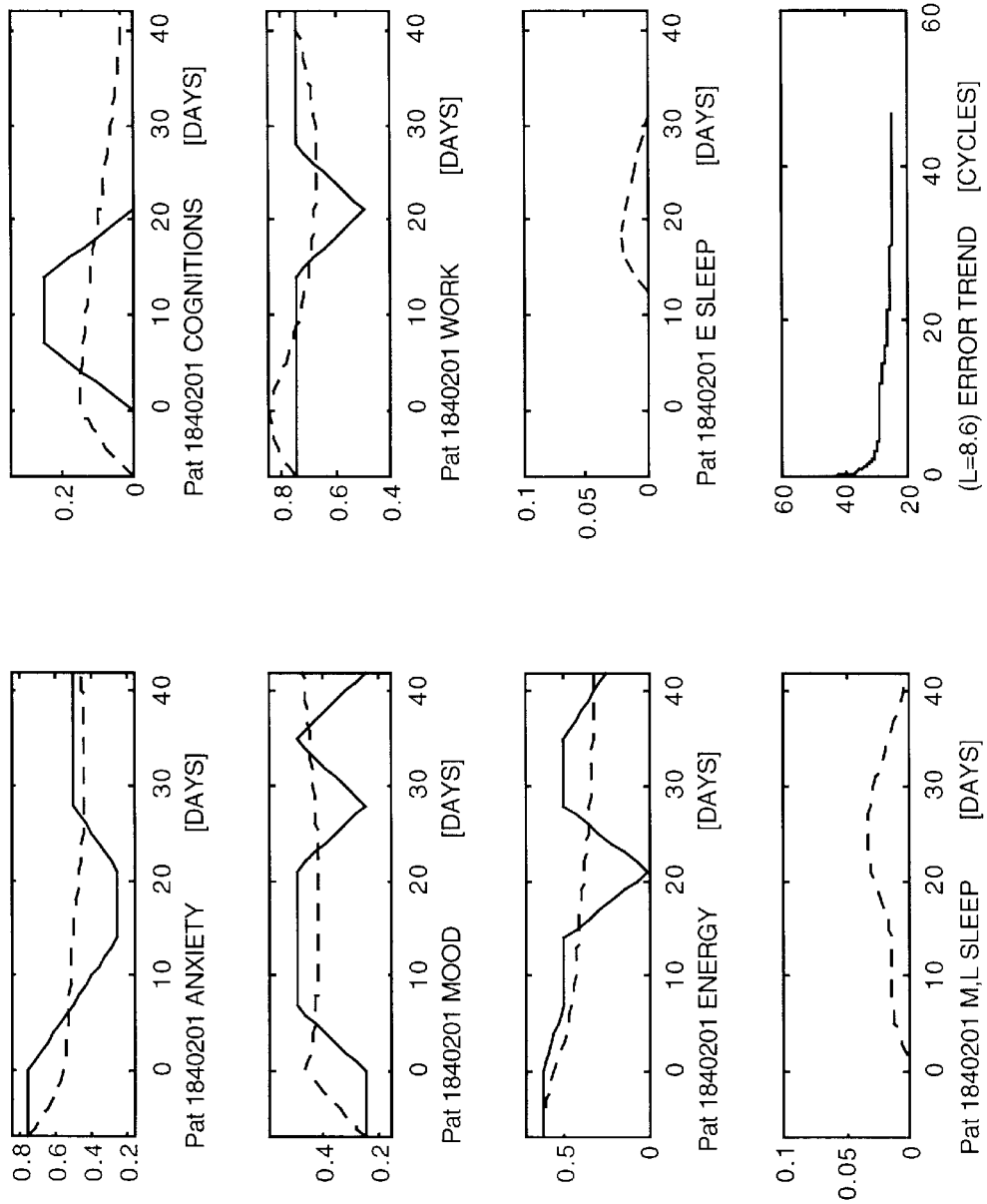
Figures 3, 4, 5, 6, 7, 8, 9, 9B:
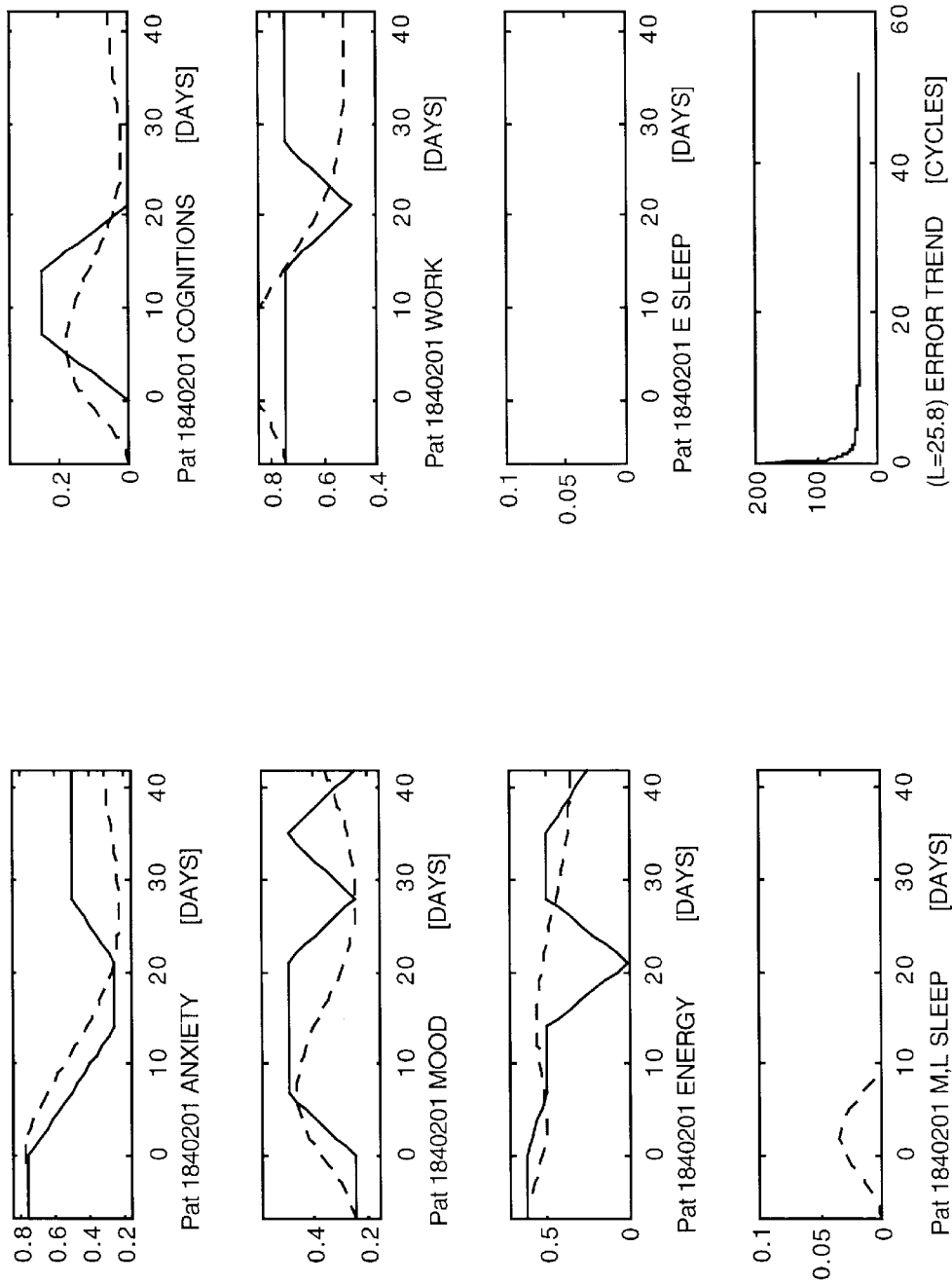
Figures 3, 4, 5, 6, 7, 8, 9, 10, 10A:
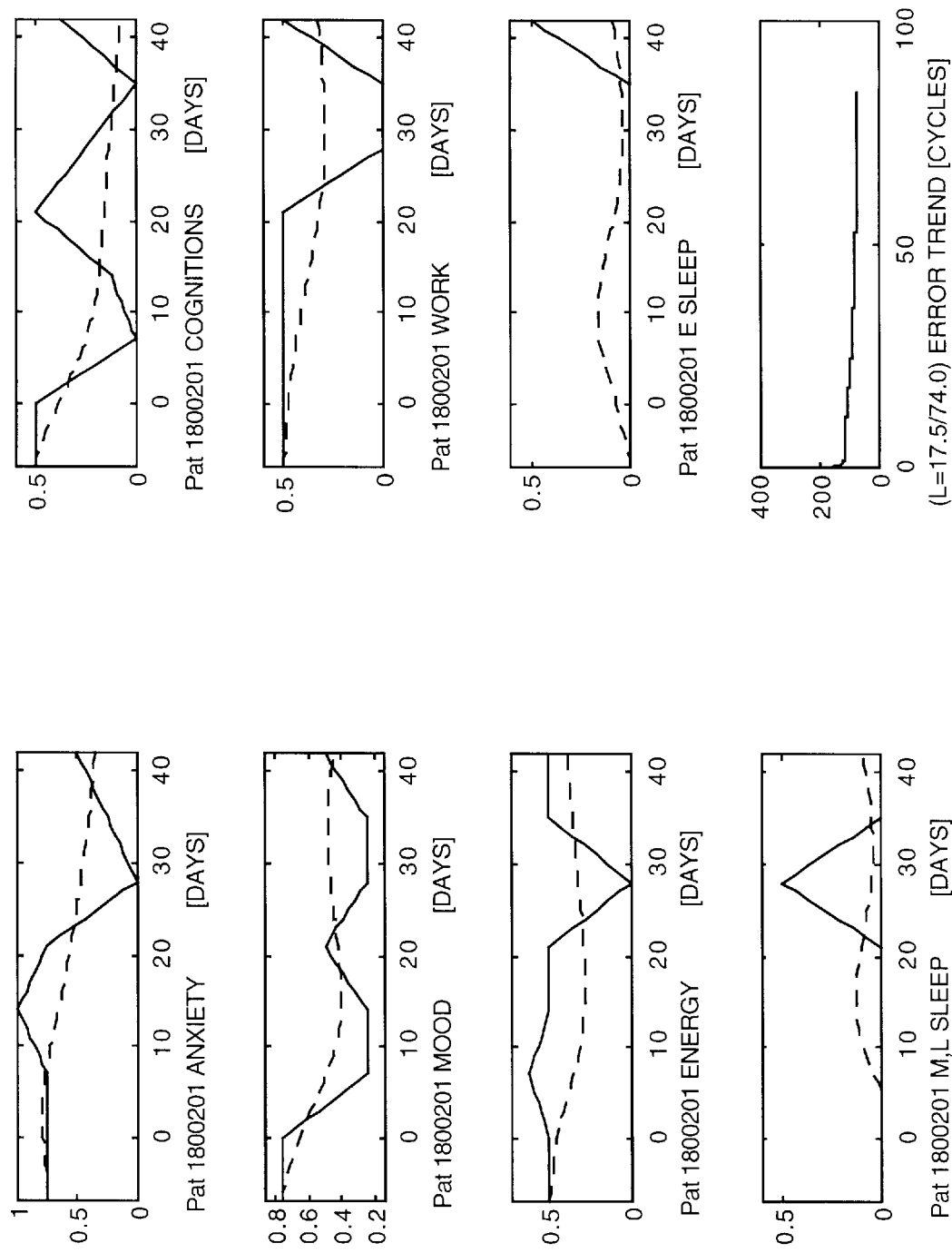
Figures 3, 4, 5, 6, 7, 8, 9, 10, 10B:
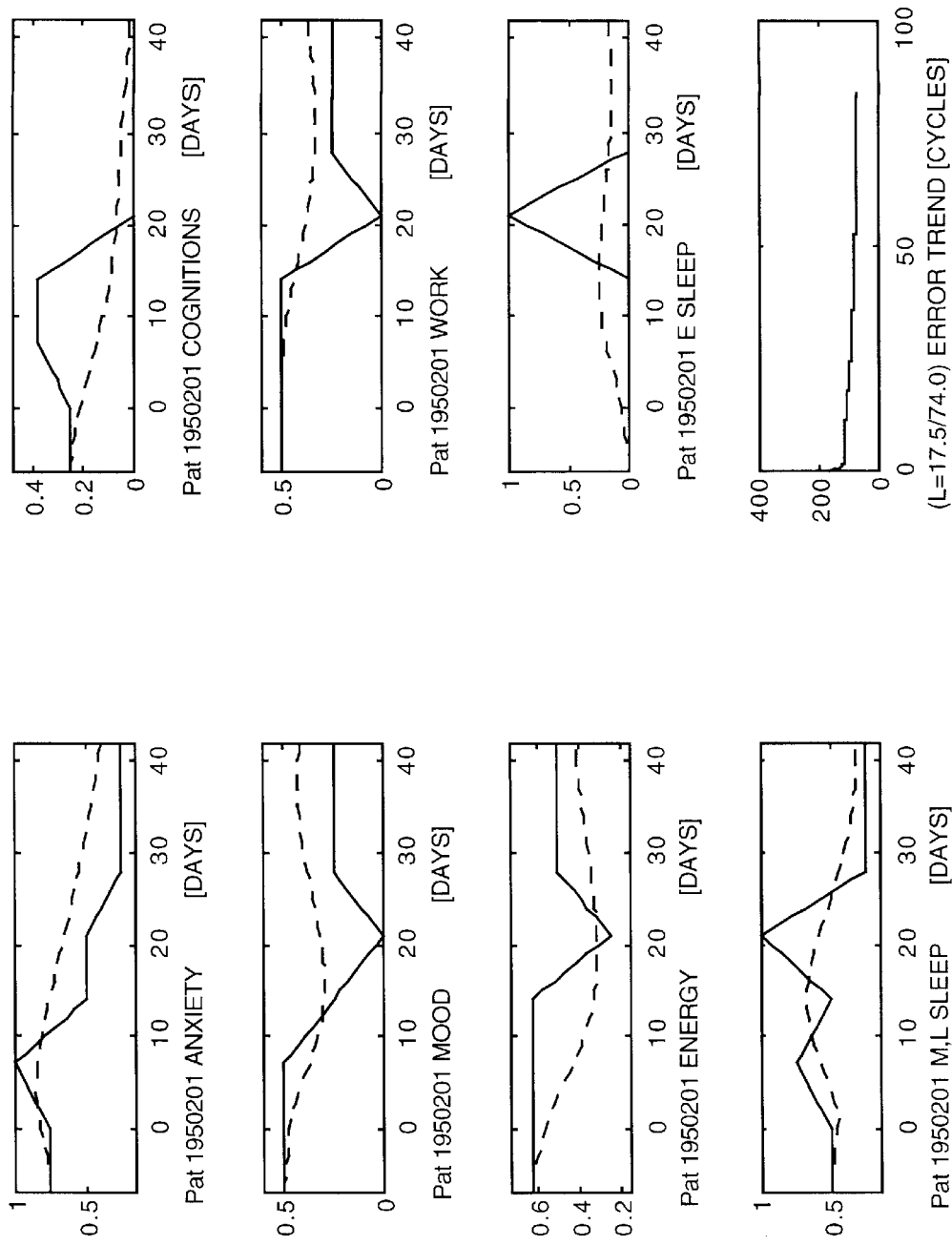
Figures 3, 4, 5, 6, 7, 8, 9, 10, 10C:
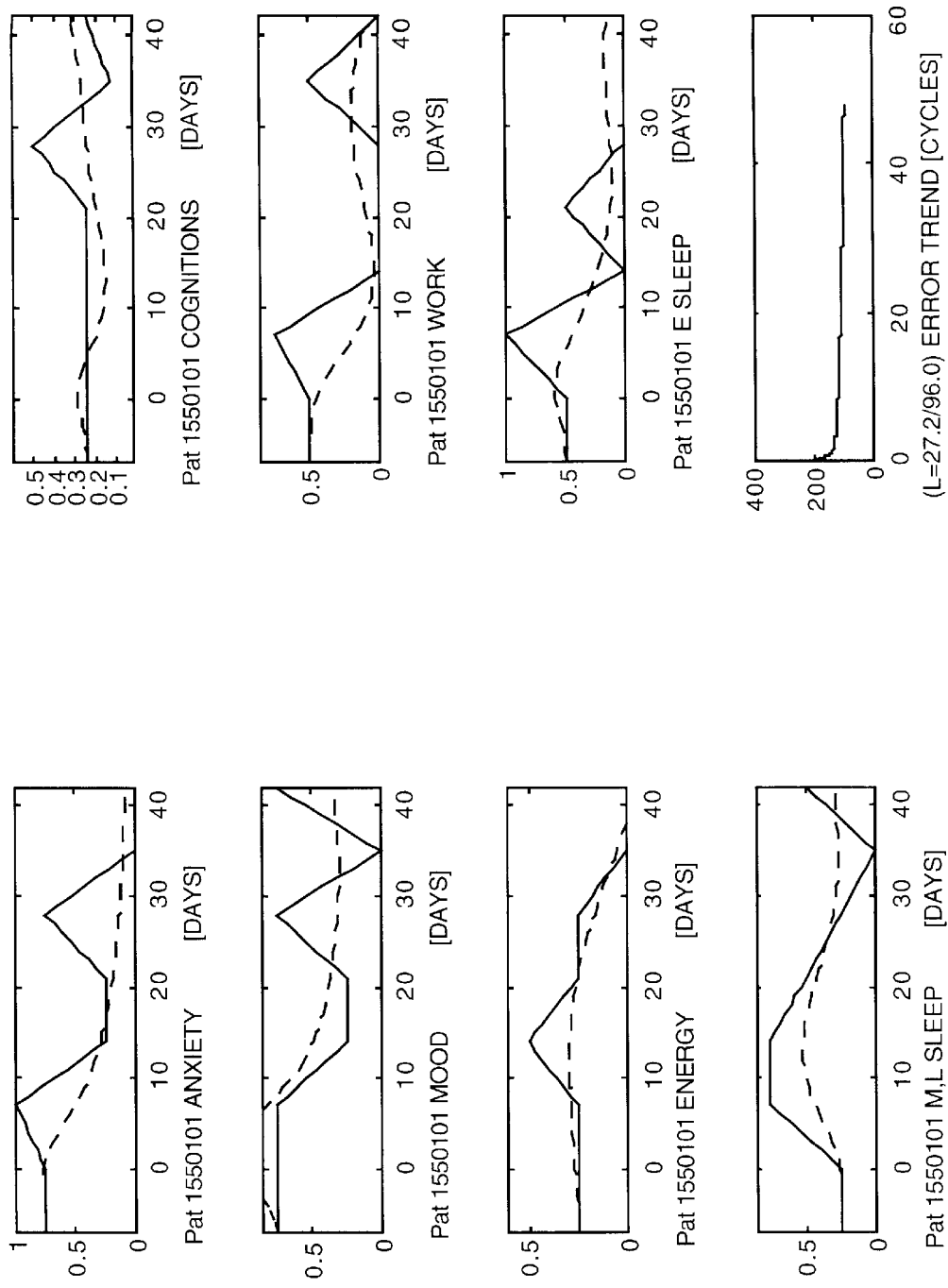
Figures 3, 4, 5, 6, 7, 8, 9, 10, 10D:
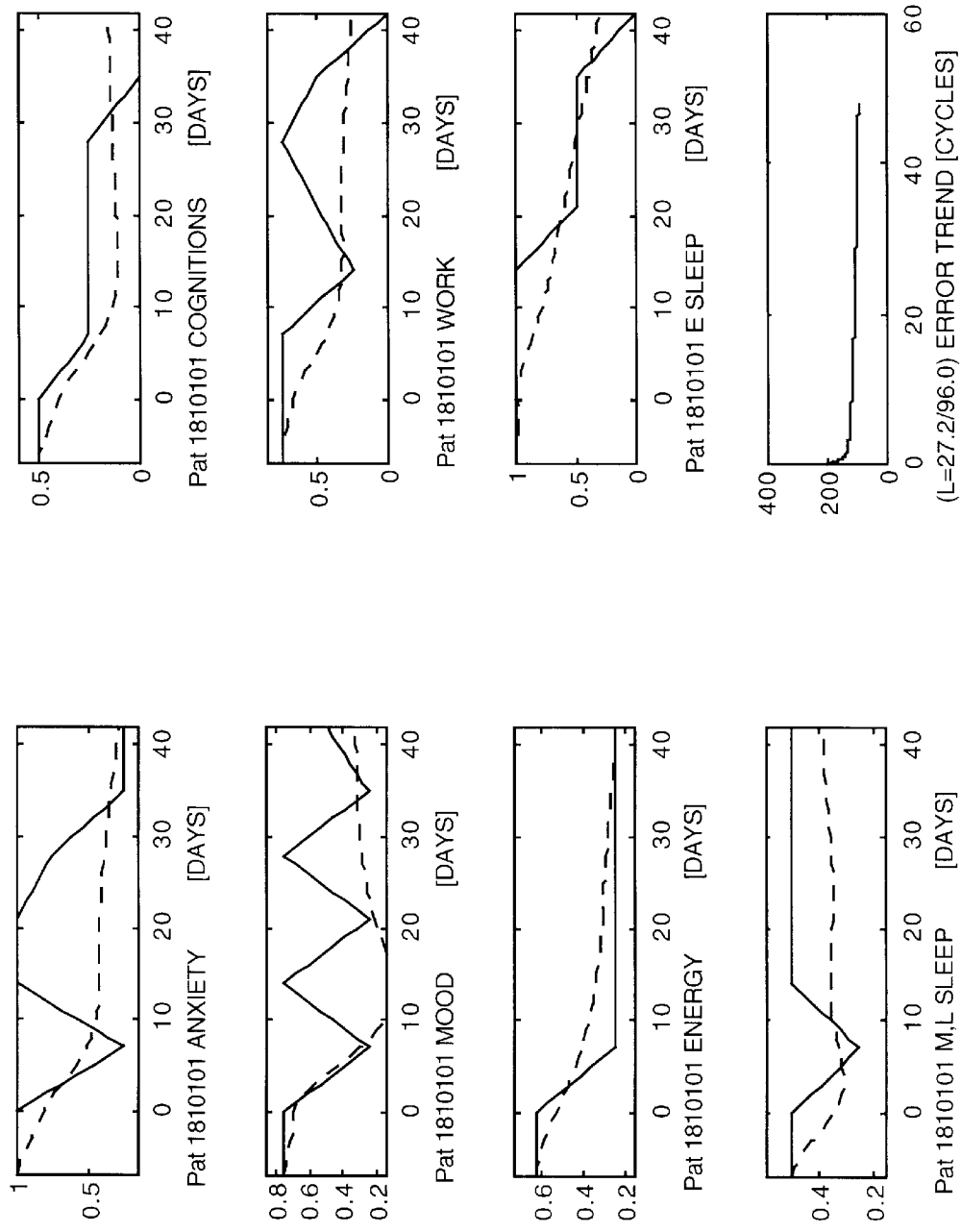
Figures 3, 4, 5, 6, 7, 8, 9, 10, 11, 11A:
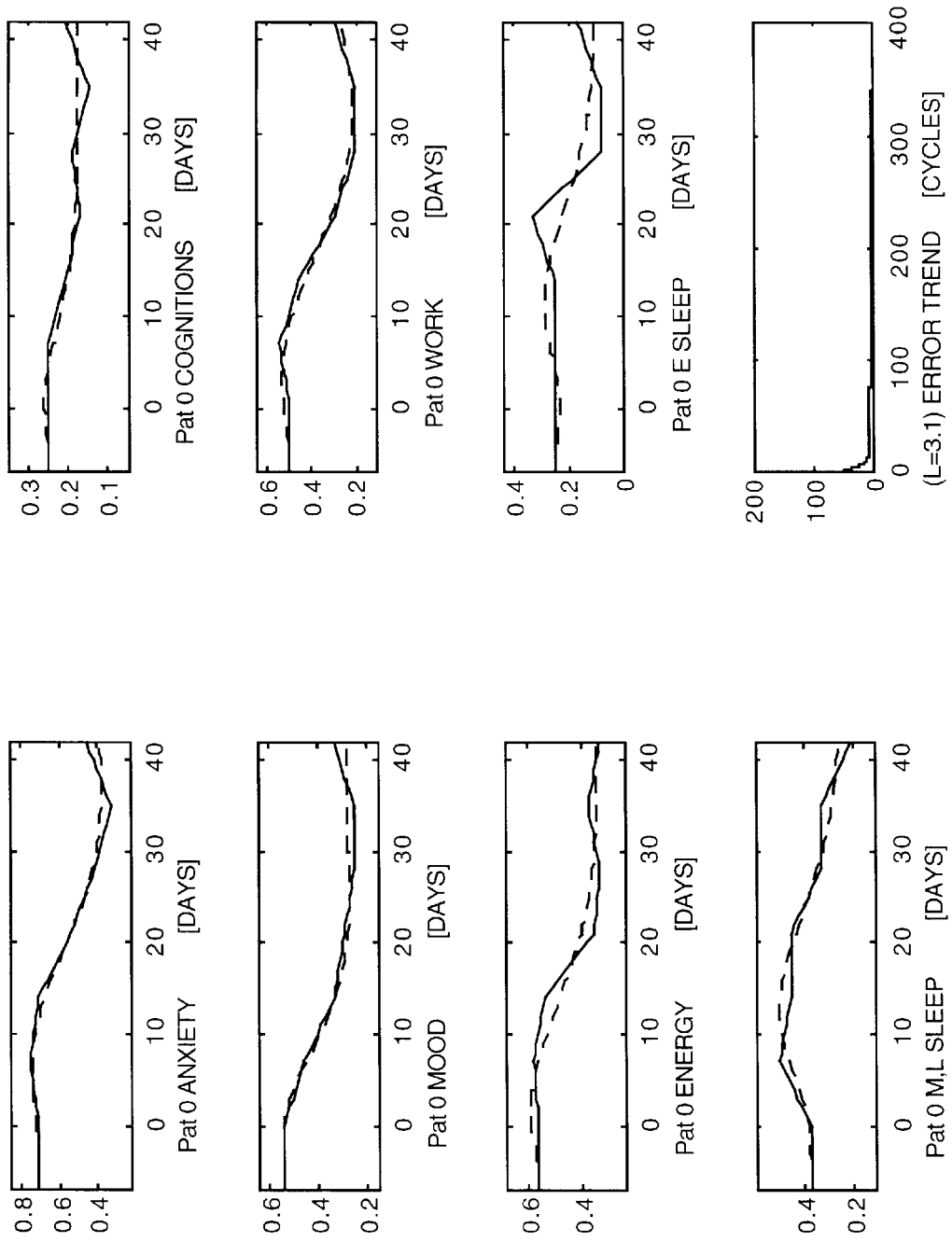
Figures 3, 4, 5, 6, 7, 8, 9, 10, 11, 11B:
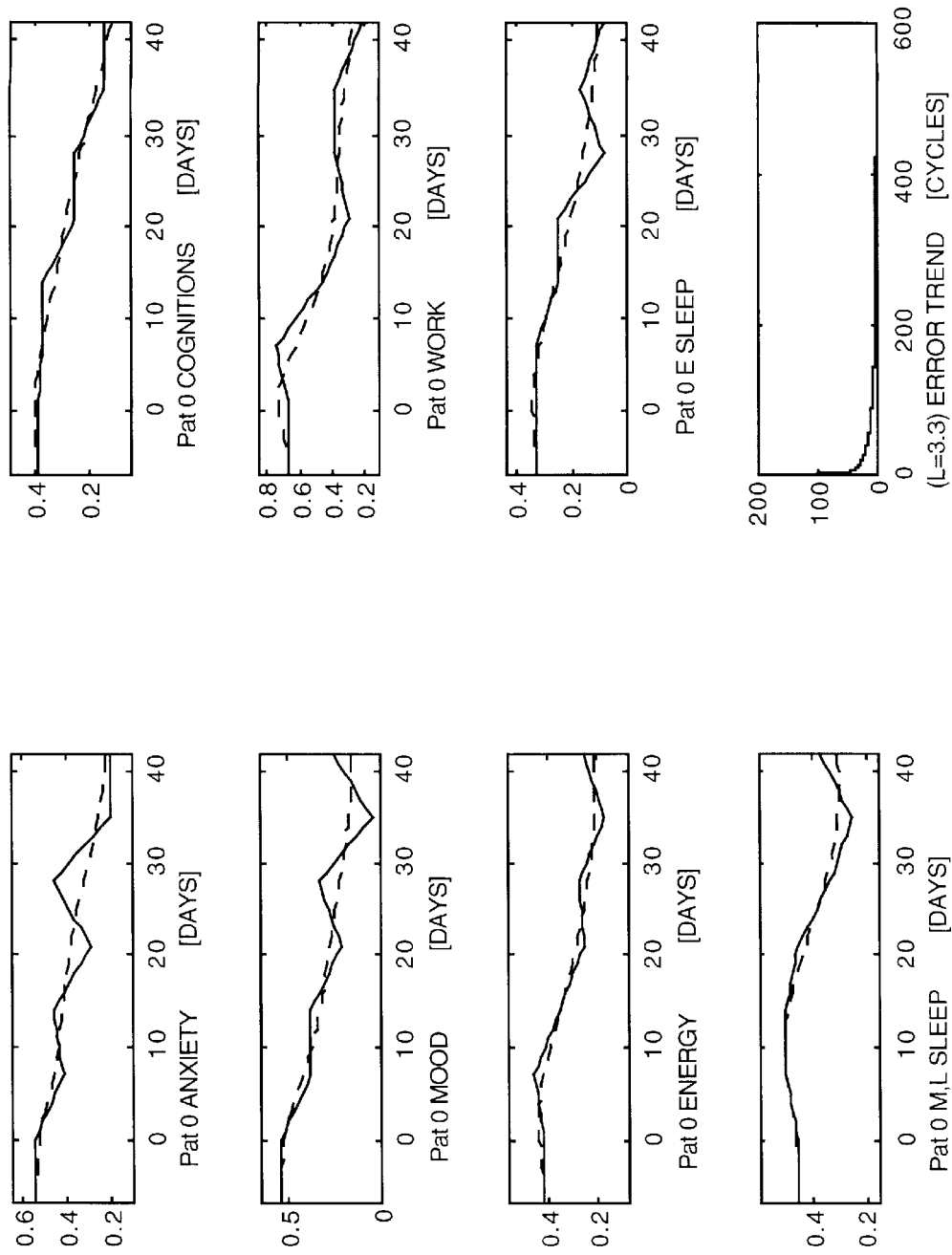
Figures 3, 4, 5, 6, 7, 8, 9, 10, 11, 12:
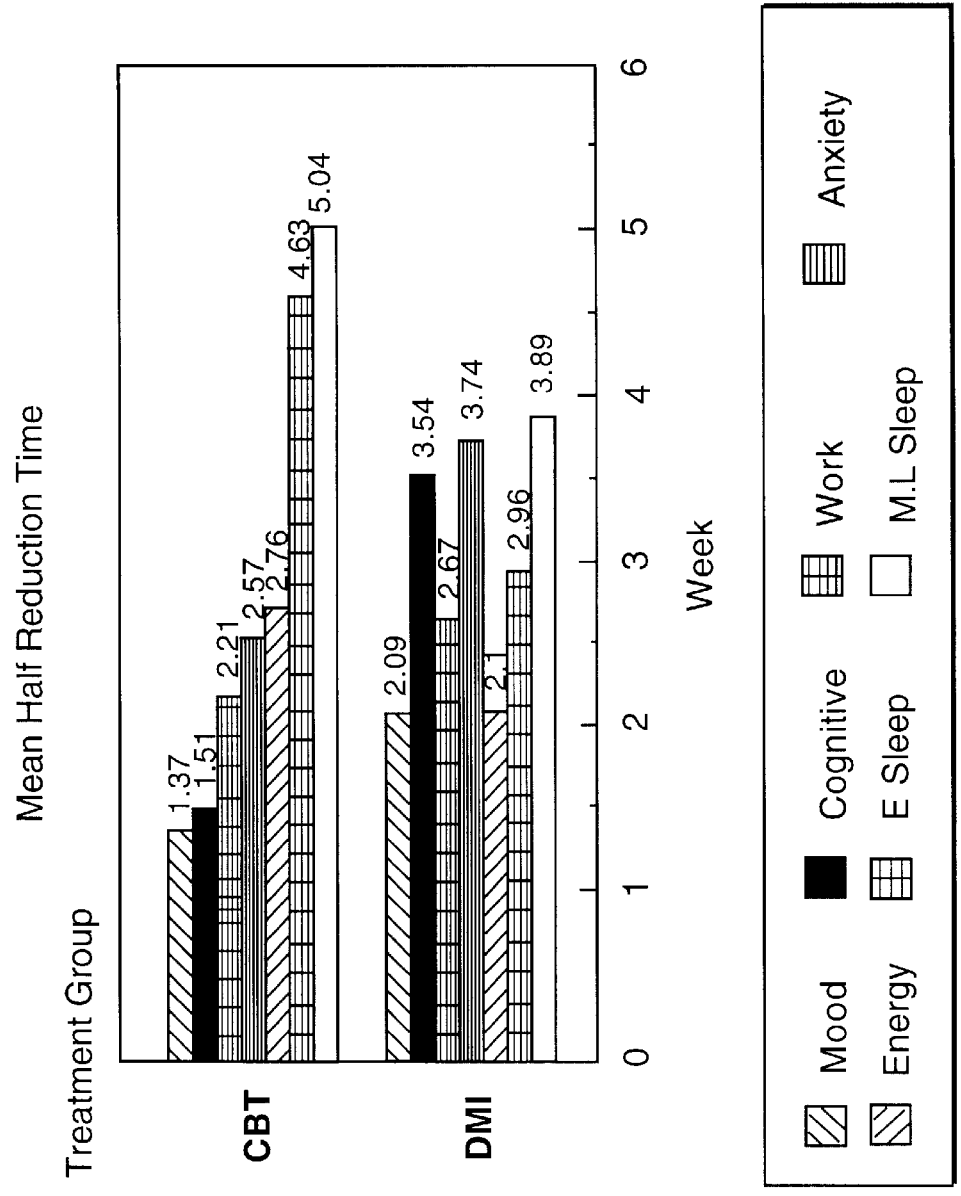
Figures 3, 4, 5, 6, 7, 8, 9, 10, 11, 12, 13:
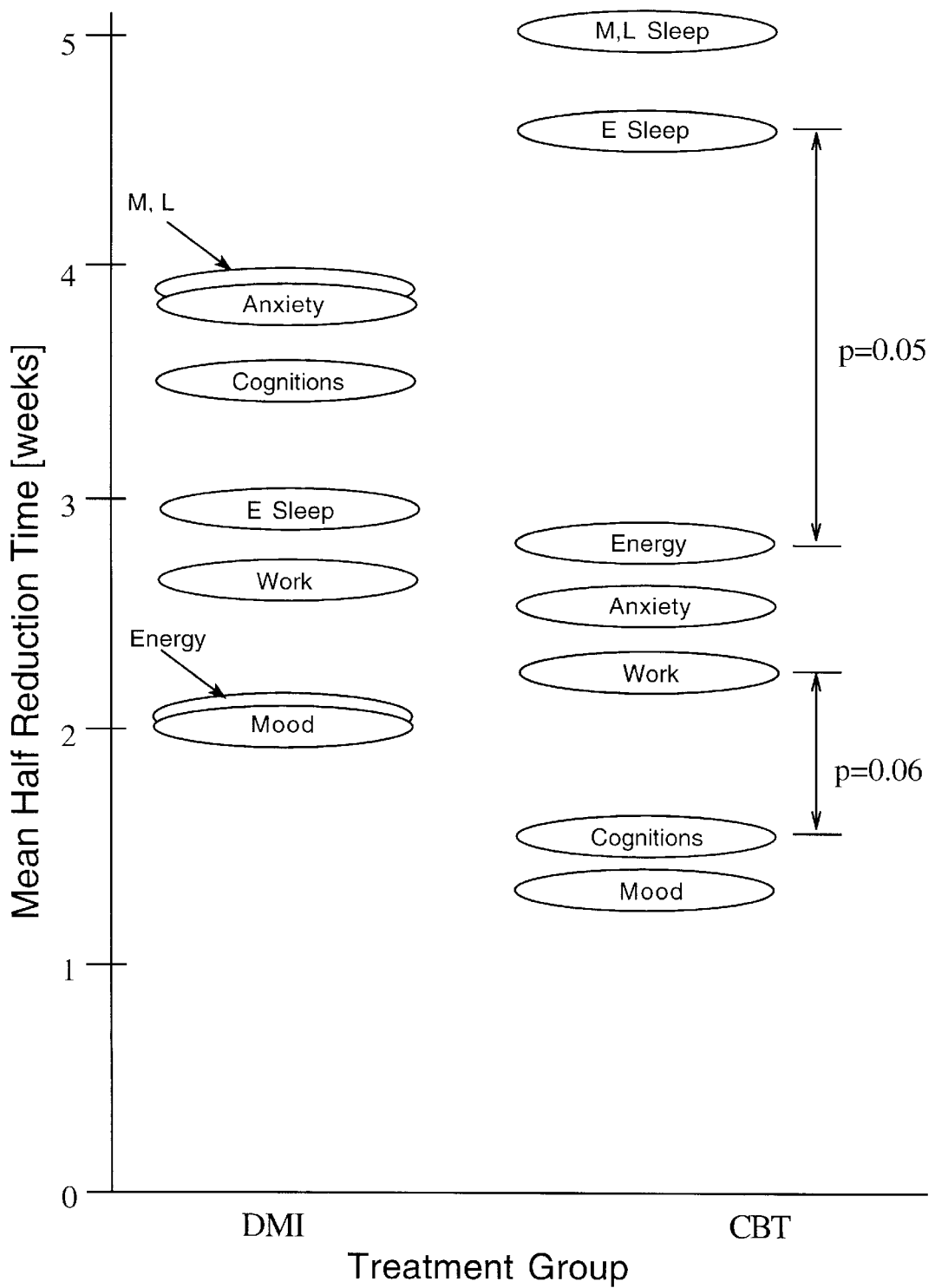
Figures 3, 4, 5, 6, 7, 8, 9, 10, 11, 12, 13, 14, 14A:
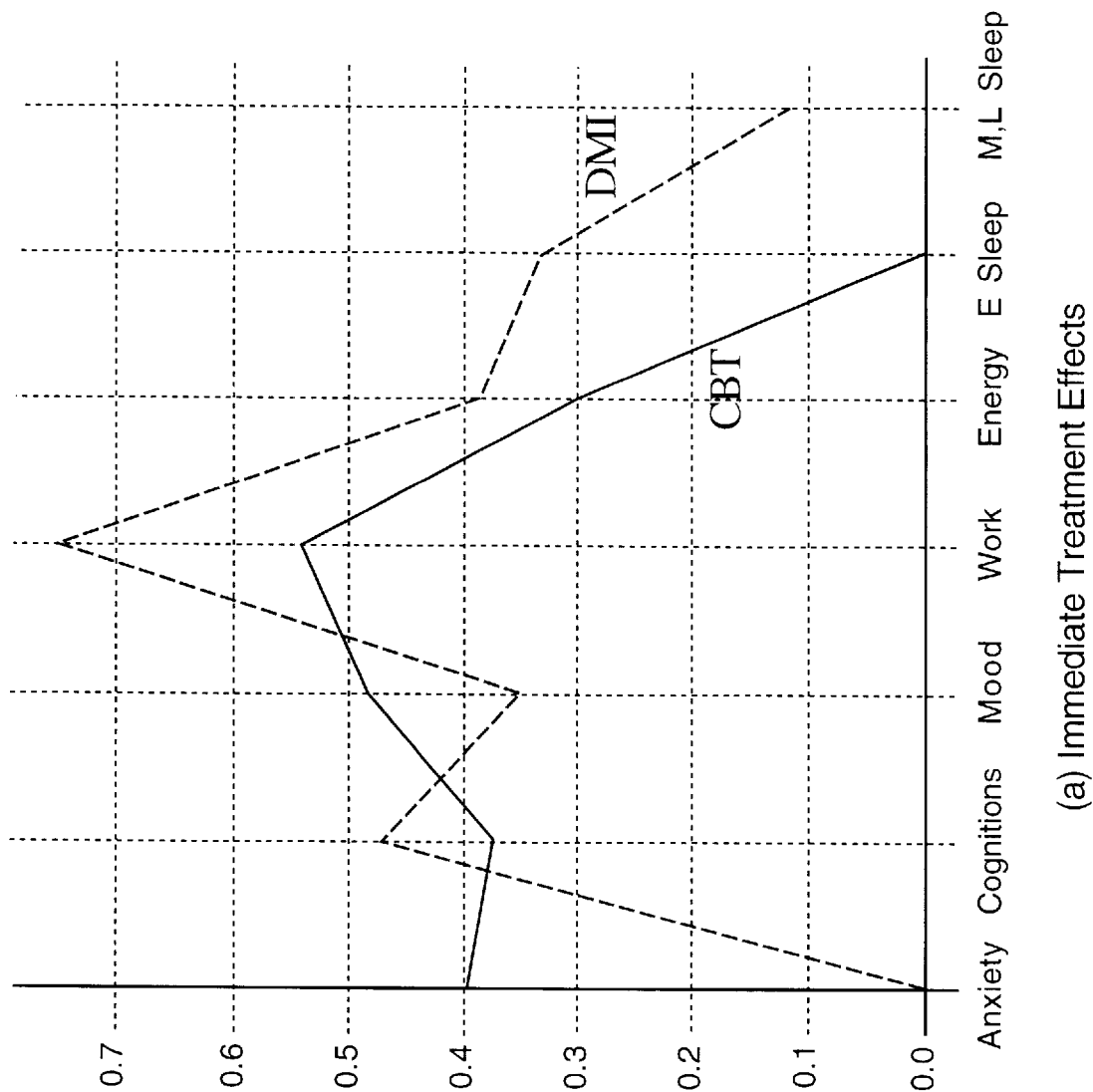
Figures 3, 4, 5, 6, 7, 8, 9, 10, 11, 12, 13, 14, 14B:
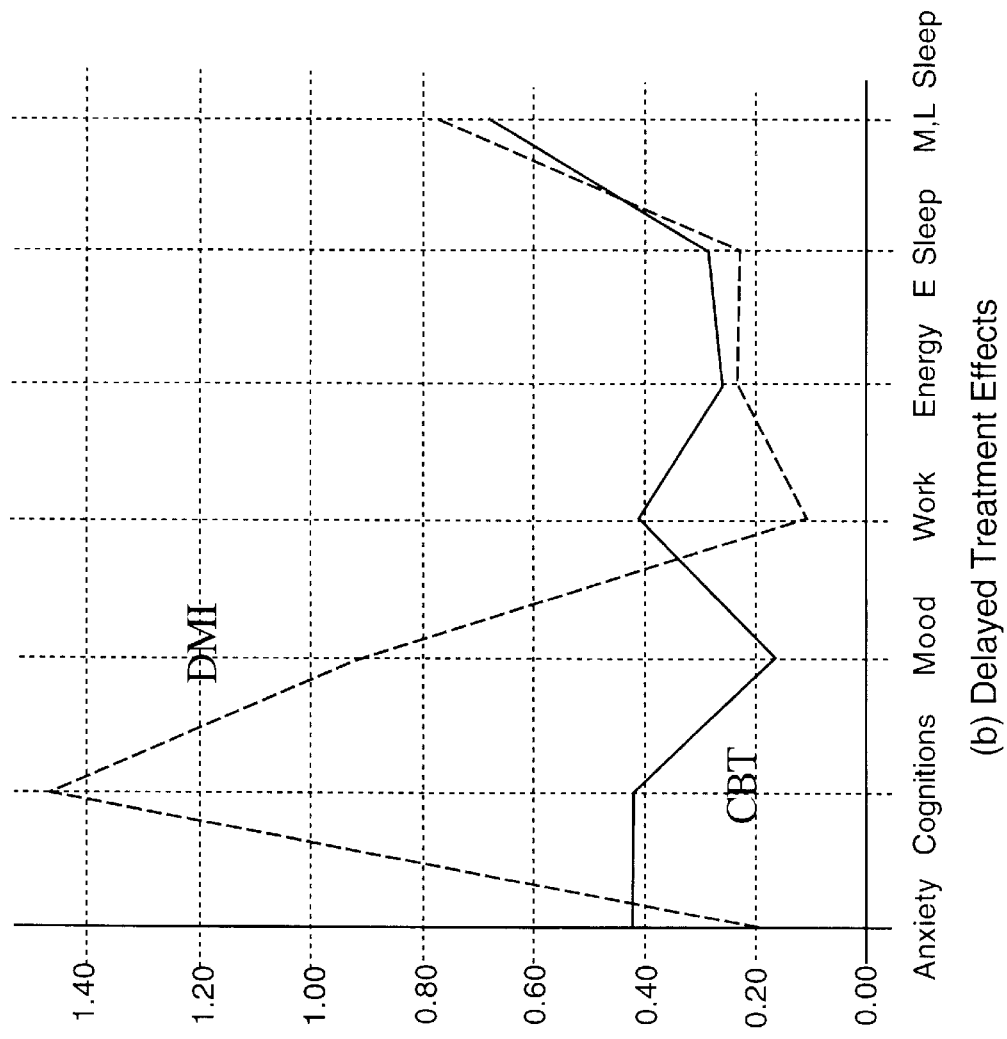
Figures 3, 4, 5, 6, 7, 8, 9, 10, 11, 12, 13, 14, 15:
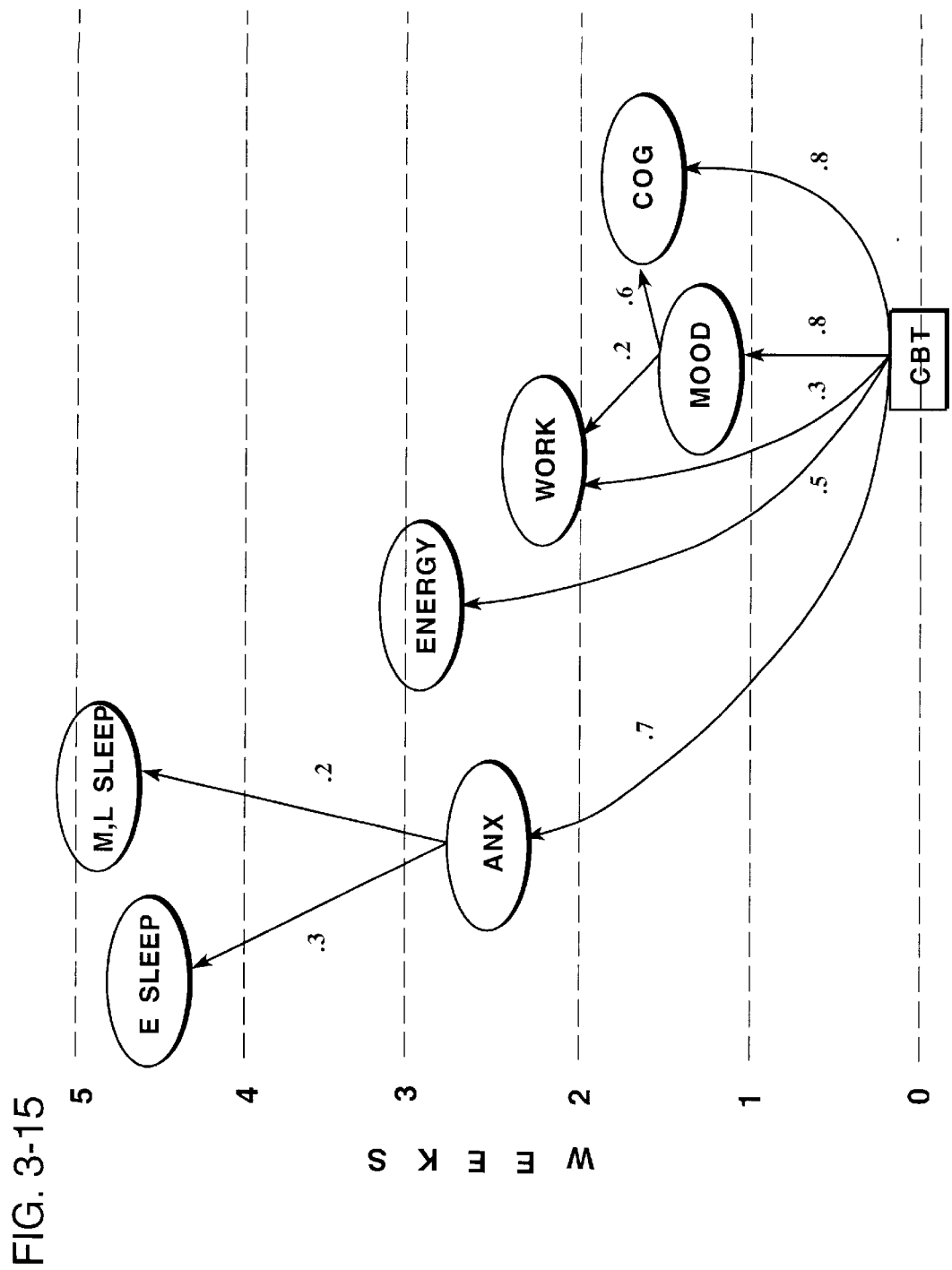
Figures 3, 4, 5, 6, 7, 8, 9, 10, 11, 12, 13, 14, 15, 16:
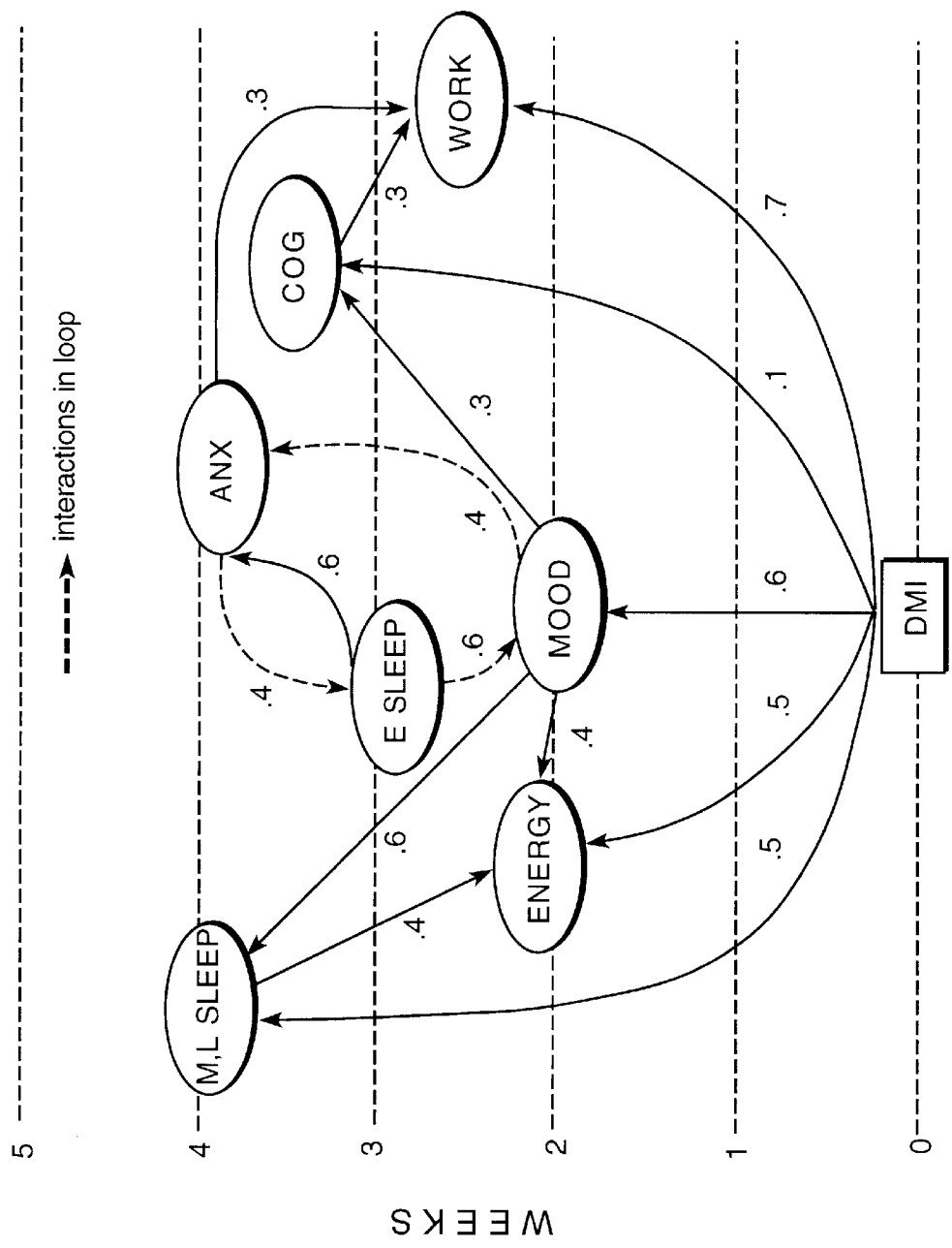
Figures 3, 4, 5, 6, 7, 8, 9, 10, 11, 12, 13, 14, 15, 16, 17:
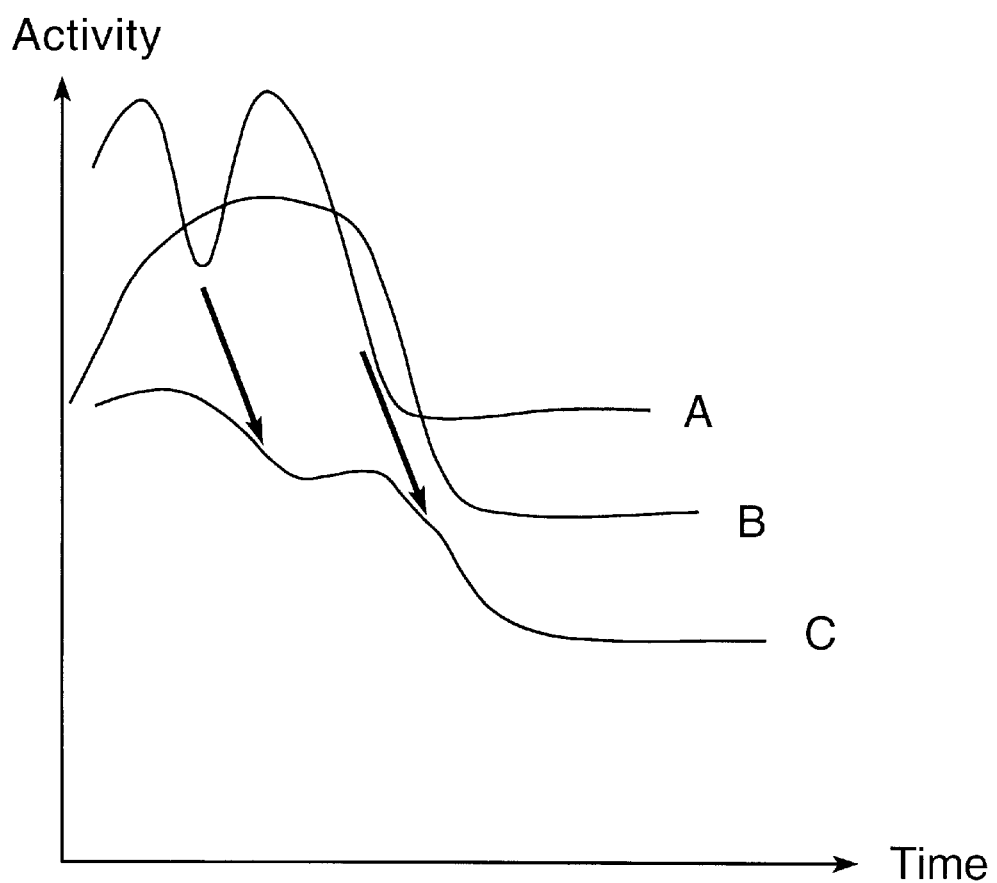
Figures 2, 4:
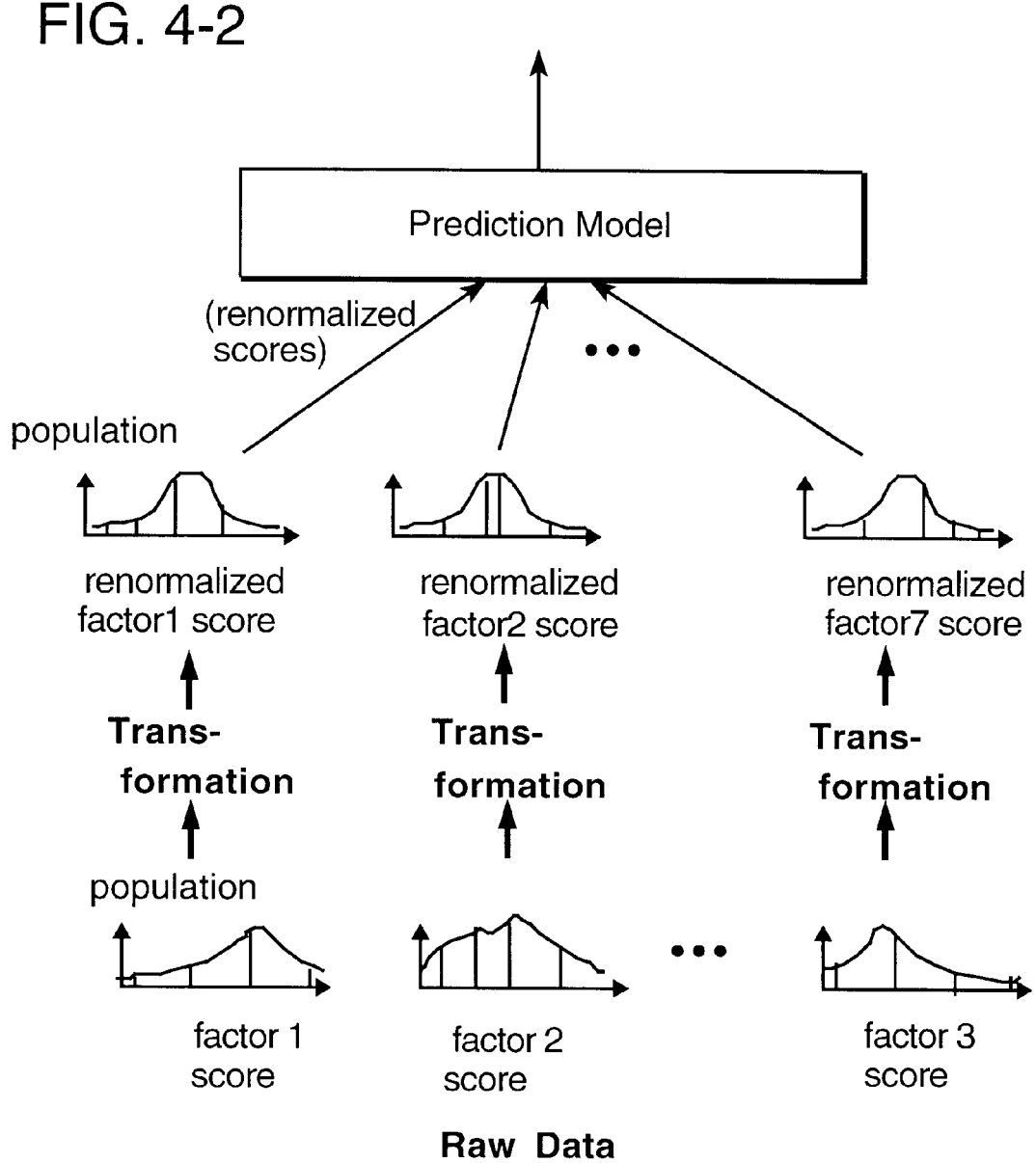

Referring now to FIG. 3-5 modeling of latency is illustrated. The direct effects of treatment are either immediate 510 (step function) or delayed 520 (sigmoid function). Delays are estimated by treatment from the patient data, using an optimization procedure.

Clinically, latency is defined as the response time of a symptom to a treatment. For example, it is well established that antidepressant drug treatments can take up to 4 weeks before the patient responds. In the recovery model, latency ($\Delta t$) is defined as the time from the beginning of treatment to when the effect of the treatment achieved half of its full accumulated effect on the symptom.

The recovery model's direct effects can occur through two treatment pathways: one with latency, and one without latency. To separate and thus capture the immediate and the delayed effects of treatment, two nodes were added and trained on the data. As shown in FIG. 3-5, the pathway with latency is represented by a delay node that is a sigmoid function with two parameters: delay and steepness of The onset of the delayed effect. The pathway without latency is represented by a step function fixed to coincide with the onset of the treatment. (Note: The simulated time-course begins one week before the onset of treatment.) All parameters were estimated by a training algorithm.

Interactions

Symptoms may affect each other. For example, increased energy may increase productivity at work. The effect is modeled by a link froma source symptom to a target symptom as is illustrated in FIG. 3-6, recovery model detail. Direct effects and interactions in the recovery model wherein $u_i$ represents the strength of the immediate effect of treatment on symptom node i, $v_i$ represents the strength of the delayed effect of treatment on symptom i; and $w_{ij}$ and $w_{ji}$ represent the interaction between the symptoms: the strength of the effect of symptom i on symptom j and the strength of the effect of symptom j on symptom i, respectively.

The second order model assumes that a source symptom's deviation from intensity correlates with the acceleration of target symptoms through interaction coefficients.

Derived Measures

Accumulated Interaction Strength

The calculation for the accumulated interaction strength of symptoms utilizes the fact that the symptom factors were normalized by shifting and scaling the data to have mean values equal to 0.0 and variance values equal to 1.0, and that the maximum values of the step function and sigmoid function are 1.0. This measure is a rough approximation valid for the center of the range for the second order model. Measures of interactions among symptoms were derived from the second order equation 3.6 by ignoring indirectly propagated influence (for instance, influence of factor j on factor i via factor k). Variables and parameters that appear in these equations are defined in Table 3.1

$$W_{ij} = -\frac{2}{T^2} \int\int w_{ij}(x_j - B_j) d^2 t \qquad (3.2)$$
$$\simeq -w_{ij} B_j$$

$$U_i = -\frac{2}{T^2} \int\int \{w_{ii}(x_i - B_i) + u_i s(t) + v_i h(t)\} d^2 t \qquad (3.3)$$
$$\simeq -w_{ii} B_i - u_i - v_i \left(1 - \frac{\Delta t}{T}\right)^2$$

where T is the entire treatment period (six weeks), $W_{ij}$ is the measure of total influence of symptom factor j on symptom factor i, when $x_i$ is small, and $U_i$ is the measure of total influence of the treatment intervention on the symptom factor T when $x_I$ is small.

Latency of Each Factor: Half Reduction Time

To compare the patterns of response to treatments we needed to construct the temporal structure of a patient's response. This meant that we needed a way to determine when each symptom responded to treatment. Based on the optimized model's prediction of a symptom's response trajectory, a measurement was made of the time it takes for the modeled symptom's intensity to decrease halfway from its initial intensity to its intensity after six weeks of treatment. This measurement is called the half reduction time (hrt). The hrt value is a prediction by the model after it has been trained on patient data, initialized with the baseline symptom values of a single patient, and allowed to evolve in accordance with the parameterized differential equations.

The half reduction time (response time) of a symptom i ($hrt_i$ P) for a given patient P is formally defined, when it exists, as follows:

$$hrt_i^P = \{k | (k \in B_i) \ \& \ \forall k'(k' \in B_i \rightarrow k \leq k')\} \qquad (3.4)$$

$$B_i = \left\{t \middle| (x_i(0) > x_i(T)) \ \& \left(x_i(t) \leq \frac{x_i(0) + x_i(T)}{2}\right)\right\} \qquad (3.5)$$

where $x_i$ (t) is the predicted symptom factor value of a patient on the $t_{th}$ day after the beginning of treatment, and T is the end of the 6 weeks of treatment (thus T=6*7=42). This represents the shortest time by which a symptom has fallen to the average of its beginning and final value. Predicted symptom patterns that did not decrease were excluded from the calculation of the half reduction time mean.

Range Score: Temporal Duration of Treatment Response

In addition to the response time, we were interested in examining the temporal duration of the response. To address this aspect of the recovery pattern, we constructed the range score, defined as the time [number of days] between the day the first symptom reaches its half reduction time to the day the last symptom reaches its half reduction time. This score is based upon the half reduction times predicted by the model.

For individual patient trajectories, it is possible for the model to predict that some symptom will simply not improve the therefore, the half reduction time is not defined. The model did so in four (DMI) to five (CBT) cases out of a total of 42 possible half reduction times. To fill in missing data, two approaches were considered. One approach omits the patient's data for that symptom from the analysis, the other approach replaces the missing value with a hypothetical minimum or maximum depending on what occurred in the actual data of that patient.

The two approaches for filling in data where the half reduction time was undefined are:

1. If the symptom was not present (and therefore could not improve)then use the value zero days for the half reduction time for that symptom.
2. If the symptom was present, and either stayed at the same level throughout the six weeks or worsened, then use the value equivalent to the maximum possible value, i.e. 42 days (six weeks) for the half reduction time for that symptom.

The more conservative approach, which omits the symptom from the calculation was adopted. This approach is more conservative because it reduces the number of data points available for statistical analyses and thus makes it harder to achieve statistical significance. For this measure in particular, the omission of a symptom, depending on the symptom, can have a large impact on the range score. Thus, if the symptom is one whose mean reduction time is on one of the extremes (either very short or very long) then its omission will shorten the range score for that symptom and make it harder to show significant differences in the response patterns of different treatments.

Most of the statistical tests and discussion are based on derived measures, in particular, the model-dependent half reduction times. There are two reasons for this approach. First, Tables 3.3 and 3.4 show the fits of the model to the data are highly significant. The highly significant results suggest that the model captures aspects of the data and it is therefore appropriate to study the model's behavior. Subsequent section "Use of the Predicted Half Reduction Time Derived Measure" show that when predicted and actual half reduction times both are defined, they are highly correlated. Section "Results: Statistical Inferences" is devoted to the elucidation of the differing patterns that resulted from training on two different treatment groups. There, the computed half reduction times were used to quantify the results obtained from model predictions based on individual initial conditions.

Model Considered

First and Second Order Systems

One of the two classes of models used in this study was a system of linear second order differential equations. The second order model is presented in detail because it was the model ultimately chosen. The equations can be understood by their analogy to equations familiar from kinematics. Variables $x_i$, $x_I$, and $x_I$ can be thought of as acceleration, velocity, and displacement, respectively. Each symptom of each patient is assigned a baseline value$B_I$, reflecting its pre-treatment value. A deviation of intensity of a symptom value $x_I$ from its baseline value $B_I$, gives rise to two kinds of forces. The restoration force, a product of the deviation and the coefficient $w_{ij}$, tends to return the system to its baseline value $B_I$, (and therefore is $w_{ij}$ constrained to be negative). An interaction force, a product of the deviation and $w_{ij}$ links the strength of the symptom to the acceleration of other symptoms and thereby cause the other symptoms to covary. (The sign of coefficient indicates whether improvement in the symptom will improve or impede improvement in another covarying symptom.)

Second Order Model System $$\ddot{x}_i = -A_i \dot{x}_i + \sum_{j=1}^{N}(x_j - B_j)w_{ij} + s(t)u_i + h(\alpha, t - \Delta t)v_i \quad (3.6)$$

$$s(t) = \begin{cases} 0 & t < 0 \\ 1 & \text{otherwise} \end{cases} \quad (3.7)$$

$$h(\alpha, t - \Delta t) = \frac{1}{1 + e^{-\alpha(t-\Delta t)}} \quad (3.8)$$

The meaning of each term in equation 3.6 is labeled in FIG. 3.4 and Table 3.1. The value of variables $x_i$, where $i=1,2,\ldots,N$ and $N=7$ is the number of symptoms under study, the predicted HDRS score of symptom I. Parameters are defined as follows: $A_I$ is a damping First Order (Shunting) Model Another model class that was explored in the current research was a first order shunting model (Grossberg, 1982) of the following form:

$$\dot{x}_i = -A_i(x_i - D_i) + \quad (3.9)$$

$$(B_i - x_i)\left(\sum_{j=1}^{N} w_{ij}^+ x_j + u_i^+ s(t) + v_i^+ h(\alpha, t - \Delta t)\right) -$$

$$(C_i + x_i)\left(\sum_{j=1}^{N} w_{ij}^- x_j + u_i^- s(t) + v_i^- h(\alpha, t - \Delta t)\right)$$

where $A_i$ is a decay constant, $B_i$ is an upper limit of a factor, $C_i$ is a lower limit, $D_i$ is a baseline, $w_{ij}^+$ is an excitatory interaction coefficient, $w_{ij}^-$ is an inhibitory interaction coefficient, $u_i^+$ is an excitatory immediate direct effect coefficient, $u_i^-$ is an inhibitory immediate direct effect coefficient, $v_i^+$ is an excitatory latent direct effect coefficient, and $u_i^-$ is an inhibitory latent direct effect coefficient, $\alpha$ is the steepness of latent onset of treatment effect, and $\Delta_t$ is the latency for the treatment effect.

In a clinical sense, $A_i$ corresponds to the quickness of the symptom to go to the baseline value if effects of treatments and other symptoms were removed. $B_i$ and $C_i$ correspond to upper and lower limits of the symptom, in the sense that when the symptom value approaches to one of these limits the change slows down. $w_{ij}^+$ is the interaction coefficient between symptoms when a high value of symptom j tends to coincide with an increase of i, and a low value of symptom j tends to coincide with a decrease of i. $w_{ij}^-$ is the interaction coefficient between symptoms when the sign of correlation is the opposite. Thus, at most one of $w_{ij}^+$ and $w_{ij}^-$ is non-zero for a given (i,j). coefficient which acts to slow down the rate of change of a symptom. $B_I$ i=1,2, . . . , N, is the baseline (pre-treatment) value of symptom factor $x_I$. $W_{ij}$ is the coefficient of the interaction from symptomj to symptomi. Treatment intervention effects are represented by the outputs of two functions. The immediate effect is represented by a step function s(t), with onset set to the beginning of treatment intervention. The latent effect is represented by a sigmoid function h (alpha, t–$\Delta$t), representing the delayed effects of treatment intervention. The sigmoid function uses two parameters to model the delayed onset of response: (1) latency ($\Delta$t [week]) i.e. the delay and (2) steepness (alpha) the abruptness of the response onset. Though estimated form the data, latency was constrained to be the same for all factors, but the intensity of the direct treatment intervention effect to a specific symptom factor i was determined independently by coefficientsu$_I$ (immediate) and v$_I$ (latent).

TABLE 3.1

Recovery model parameters.

| Variable Name | Description |
|---|---|
| $\chi_i$ | Activity of symptom factor i |
| $A_i$ | Damping factor |
| $B_i$ | Baseline (pre-treatment factor) value |
| $w_{ij}$ | Interaction coefficient from factor j to factor i |
| $u_i$ | Treatment Intervention (immediate) to factor i |
| $v_i$ | Treatment Intervention (latent) to factor i |
| $\alpha$ | Steepness of latent onset of treatment effect |
| $\Delta t$ | Latency [weeks] for treatment effect |

Training Procedure

The parameters which yield good fits to the data were obtained through learning. This section describes processes and data that were involved in learning. Referring now to FIG. 3-7 which provides a flow chart of the training process, parameters were initialized with a regression matrix which was calculated from actual symptom values (ASV) by correlation and regression analyses. The model used these initial parameters to predict symptom values (model symptom values, MSV) of each patient from baseline. The optimization process iteratively modified parameters to minimize the discrepancy between MSV and ASV.

MSV are daily symptom factor values starting from one week prior to the onset of treatment, whereas ASV are weekly data starting from the onset of treatment. Prior to the optimization process, ASV were transformed into the same format as MSV. This was done by extending the ASV by one week (from week 0 to week −1). It was assumed that the symptom factor values before the beginning of treatment were constant and equal to the baseline. A linear interpolation was used to extend the data. The extension was necessary because the model had to learn from the data the premise that the symptom factor values stay constant without treatment. The reason the data were interpolated to be daily rather than weekly was that the theories of differential equations and optimal control are continuous, and thus require finer time resolution than was available in weekly data from a six week study. The learning (training) algorithm was adapted from optimal control theory (Bryson, A. E. and Ho, Y.-C.; (1975) *Applied Optimal Control*, Hemisphere Publishing Co., New York) and is described in detail for the second order model only. Parameters for the Shunting Model may be found in Luciano, U.S. Provisional Application Ser. No. 60/041,287 filed on Mar. 20, 1997, the disclosure of which is incorporated herein by reference.

The goal of the training procedure is to find the best model parameters. The method is to reduce the discrepancy between the prediction of the model and the actual data. To do this, model parameters are incrementally changed so that the discrepancy between the actual and simulated time series is gradually decreased. The discrepancy L (FIG. 3-8), also called the Lagrangian, was defined as an integral of the squared difference between the predicted and actual symptom values through time. Later the Lagrange multiplier u which represents a constraint that the differential equation must hold is introduced, and will serve to simplify calculation of the gradient.

Referring now to FIG. 3-8, a schematic description of the cost function L is illustrated. The formula inside the integration has two terms 810 and 820 respectively. By minimizing the first term 810, discrepancies between estimated and actual patterns of recovery are minimized. The second term 820 is a constraint term which states that the differential equation must hold.

Estimating initial values of model parameters

Vector auto regression analysis was applied to obtain the initial estimates of the model's parameters. The coefficient matrix in the first order differential equation 3.13 is analogous to an auto regression matrix when the equation is approximated by a difference equation. Therefore, a first order regression matrix was computed, and a part of the matrix was used to calculate initial values of the parameters of differential equations.

Second order equations for x (Equation 3.6) were first decomposed into a set of first order differential equations.

$$\dot{x}_i = y_i \tag{3.10}$$

$$\dot{y} = -A_i y_i + \Sigma w_{ij}(x_j - B_j) + u_i s(t) + v_i h(t) \tag{3.11}$$

Or, in a matrix form, where P is the set of parameters in this equation ($w_{ij}$, $A_i$, $B_i$, $u_i$, $v_i$). Initial values of the parameters were estimated using regression analysis, and then optimized through a training procedure (Bryson, A. E. and Ho, Y.-C.; (1975) *Applied Optimal Control*, Hemisphere Publishing Co., New York).

The auto regression matrix was calculated for a vector $[X_i']$ which includes the symptom variables $x_i$, their derivatives $y_i$, and immediate intervention effect s(t).

$$X' = [x_1 \ldots x_n \; s(t) \; y_1 \ldots y_n \; s'(t)]^T \tag{3.14}$$

In this initial estimation process, the immediate intervention effect from s(t) was treated as another variable, and the latent intervention effect from h(t) was ignored. Although s^(0) is undefined, it is assumed to be 1.0, the difference of s(0)−s(−1). With these preparations, the calculation of the auto regression matrix and extraction of the initial parameters of the differential equations from the auto regression matrix were carried out as follows:

Step 1: Compute a regression matrix

Covariance matrices of X with two different time intervals Lambda(1) and Lambda(2) were calculated, the results of which were used to calculate an auto regression matrix. First order regression on a time series vector X'(t) was defined as follows.

$$X'(t+1) = \Phi_1 X'(t) + r(t) \tag{3.15}$$

where $\text{Phi}_1$ is the first order regression matrix, and r(t) is a disturbance (white noise) vector. $\text{Phi}_1$ is calculated from correlation matrices.

$$\Phi_1 = \Lambda(1)\Lambda^{-1}(0) \tag{3.16}$$

wherein Lambda(k) is the $k_{th}$ covariance matrix. A covariance matrix is calculated from the actual time series data X'', as an average of covariance over time t and over patients.

$$\Lambda(k)_{ij} = E(X_i'(t)X_j'(t-k))) \tag{3.17}$$

Derivatives $y_i$ in X' are approximated by the first Difference $x_i - x_{I-1}$. The unit of time is weeks because the HDRS symptom measurements were obtained weekly.

Step 2: Compute the Transition Matrix

This step estimates P', a transition matrix of symptoms from which initial parameters will be extracted. The transition matrix is a parameter in the state space difference equation that approximates the differential equation.

$$\Delta X'(t) = P'X'(t) \tag{3.18}$$

P' is calculated based on $\text{Phi}_1$, the auto-regression matrix calculated in Step 1. From equations 3.15 and 3.18, $$X'(t+1) - X'(t) = P'X'(t) \tag{3.19}$$

$$X'(t+1) = X'(t) + P'X'(t) \tag{3.20}$$

$$= (I + P')X'(t) \tag{3.21}$$

$$P' = \Phi_1 - I \tag{3.22}$$

where 1 is an identity matrix.

Step 3: Extract Initial Parameter

An examination of the inner structure of P in equation 3.13 showed that it was appropriate to initialize the parameters as follows.

$$A_i^0 = 1 - P'_{i'i'} \tag{3.23}$$

$$w_{ij}^0 = P'_{i'j} \tag{3.24}$$

$$u_i^0 = P'_{i',N+1} \tag{3.25}$$

Where i'=i+n=l+N+1. N is the number of symptom factors and N+1 is the index corresponding to the intervention variable s(t).

$$B_i^0 = 0 \tag{3.26}$$

$$\alpha^0 = \frac{i_{max}}{2} \tag{3.27}$$

$$\Delta t^0 = 0 \tag{3.28}$$

$$v_i^0 = 0 \tag{3.29}$$

Optimization

The goal of the optimization process was to find the best parameters, i.e. those parameter values that yield the best fit to the data. This was accomplished through minimizing L, the squared error integrated over time. Each term is described in FIG. 3-8.

$$L(P) = \frac{1}{2} \int_0^T \|R(O(t) - X(P, t))\|^2 dt + \frac{1}{2} K \|P\|^2 \tag{3.30}$$

where $$R_{ij} = \begin{cases} 0 & \text{if } i \neq j \\ 1 & \text{if } i = j \leq N \\ \lambda & \text{if } i = j > N \end{cases} \tag{3.31}$$

Where P is the set of parameters, O(t) is training data (pre-processed as described above in Patient Data and X(P,t) is the value of system equation 3.11 at time t. Diagonal elements of R (equation 3.31) determined the relative importance of minimizing the error (equation 3.30) for each element in X. If lambda=0 then the optimization is insensitive to errors in the derivatives. If lambda=1 then the optimization evaluates, with the same importance, the errors in the derivative and the errors in the variables. When our objective was to compare the shunting and second order systems, we ran the simulations with lambda set to zero so that the same error function would be used for the comparison (see Table 3.3). The term $K\|P\|^2$ is used to keep the magnitude of the parameters from being large. X is the concatenated vector of factors $x_i$ and their derivatives $y_i$. It is similar to X' except it does not include treatment intervention variables. The value of K was chosen empirically (Optimization Procedure).

$$X = [x_1 \ldots x_n \ldots, y_1 \ldots y_n \ldots]^T \tag{3.32}$$

Integration was carried out using fourth order Runge-Kutta method with a time step of 1 [day]. Because the initial data were weekly, the data were linearly interpolated to daily data to get the non-derivative part of R. The derivative part of R was approximated by daily differences.

The gradient descent technique requires partial derivatives of L with respect to the components of P. To simplify the form of partial derivatives, a coefficient called the Lagrange multiplier (mu(t)) was introduced. The optimization process aims to minimize the quantity L, the Lagrangian. The term multiplying mu(t) is defined to be zero, as is explained below. This allows the meaning of L(P) to remain unchanged from the error function, equation 3.30 while allowing the form of L(P) to be amenable to the computation of the gradients with respect to parameters, $$L(P) = \frac{1}{2} \int_0^T \left\{ \|R(O(t) - X(P, t))\|^2 + \mu(t)(\dot{X}(t) - f(P, X(P, t))) \right\} dt + \tag{3.33}$$

$$\frac{1}{2} K \|P\|^2$$

In this equation, f(P,X) is the right hand side of the original differential equation 3.13, satisfying $$\dot{X}(P,t) = f(P, \hat{X}(P,t), t). \tag{3.34}$$

Thus the term with mu(t) in the cost function, equation 3.33 is always zero at the local minima, and therefore mu(t) can be determined arbitrarily to make the form of partial derivative simple, i.e. not explicitly dependent on the parameters.

The partial derivative of L with respect to parameter $P_j$ is $$\frac{\partial L}{\partial P_j} = \int_0^T \sum_i \left\{ R_{ii}(X_i - O_i) \frac{\partial X_i}{\partial P_j} + \right. \tag{3.35}$$

$$\mu_i \left( \frac{\partial \dot{X}_i}{\partial P_j} - \sum_{k'} \frac{\partial f_i}{\partial X_{k'}} \frac{\partial X_{k'}}{\partial P_j} - \frac{\partial f_i}{\partial P_j} \right) \right\} dt + K P_j$$

$$= \int_0^T \sum_i \left\{ \left( R_{ii}(X_i - O_i) - \sum_k \mu_k \frac{\partial f_k}{\partial X_i} \right) \frac{\partial X_i}{\partial P_j} \right\} dt +$$

$$\int_0^T \sum_i \mu_i \frac{\partial \dot{X}_i}{\partial P_j} dt - \int_0^T \sum_i \mu_i \frac{\partial f_i}{\partial P_j} dt + K P_j$$

$$= \int_0^T \sum_i \left\{ \left( R_{ii}(X_i - O_i) - \sum_k \mu_k \frac{\partial f_k}{\partial X_i} - \dot{\mu}_i \right) \frac{\partial X_i}{\partial P_j} \right\}$$

$$dt + \sum_i \left[ \mu_i \frac{\partial X_i}{\partial P_j} \right]_0^T - \int_0^T \sum_i \mu_i \frac{\partial f_i}{\partial P_j} + K P_j$$

Integration by parts was used in the derivation from the second to the third line above.

$$\mu_i \int_0^T \frac{\partial \dot{X}_i}{\partial P_j} dt = \left[ \mu_i \frac{\partial X_i}{\partial P_j} \right]_0^T - \int_0^T \dot{\mu}_i \frac{\partial X_i}{\partial P_j} dt \tag{3.36}$$

Because $X_i$ is defined as an explicit function of $P_i$, it is difficult to calculate $\partial X_i/\partial P_i$ which is contained in the first term of equation 3.35. The necessity to calculate $\partial X_i/\partial P_j$ was eliminated by constraining the term multiplying it to be zero. This is accomplished by setting $$\mu_i = R_{ii}(X_i - O_i) - \sum_k \mu_k \frac{\partial f_k}{\partial X_i} \quad (3.37)$$

If it is assumed that $$\begin{cases} X(0) \text{ is given and therefore } \left.\frac{\partial X_i}{\partial P_j}\right|_{i=0} = 0 \\ \mu_i(T) = 0 \end{cases}$$

Then $$\left[\mu_i \frac{\partial X_i}{\partial P_j}\right]_0^T = 0 \quad (3.38)$$

From equations 3.35, 3.36, and 3.38

$$\frac{\partial L}{\partial P_j} = -\int_0^T \sum_i \mu_i \frac{\partial f_i}{\partial P_j} dt + KP_j \quad (3.39)$$

Thus we got a simpler form of gradient under the condition of satisfying equation 3.37. This condition is met by solving equation 3.37 for $mu_i$.

Optimization Procedure

The steps in the optimization procedure are as follows:

(0) Get first patient's data.
(1) Solve the differential equation 3.11 for symptom factors.
(2) Solve the differential equation 3.37 for Lagrange multipliers.
(3) Calculate the partial derivatives and update the parameters.
(4) Calculate the cost function L given in equation 3.33.
(5) Unless one of the following holds, Stop and terminate the optimization.

The average of the absolute value of L for the 4 most recent cycles decreased from the preceding 4 cycles by more than 0.01%.

Fewer than 300 cycles have been processed.

(6) Get next patient's data. If there are no more patients, then start over with the first patient's data. Go to (1).

Differential equations were solved using the fourth order Runge-Kutta method with a step size of 1.0 [day]. The explanation for each step follows.

Solve the differential equation for symptom factors

To predict the time course of symptom factors, integrate [forward] equations 3.10 and 3.11. The notation in equation 3.13 is changed here to separate the variable vector into non-derivative $x_i$ and derivative $y_i$ parts.

$$\begin{bmatrix} x_i \\ y_i \end{bmatrix} = \int \begin{bmatrix} f_{xi}(X) \\ f_{yi}(X) \end{bmatrix} dt \quad (3.40)$$

Solve the differential equation for Lagrange multipliers

To solve for the Lagrange multipliers, integrate Equation 3.37 backwards i.e. from t=T to t=0).

$$\mu_{xi} = (x_i - O_{xi}) - \sum_k \mu_{xk} \frac{\partial f_{xk}}{\partial x_i} - \sum_k \mu_{yk} \frac{\partial f_{yk}}{\partial x_i} \quad (3.41)$$

$$= (x_i - O_{xi}) - \sum_k \mu_{yk} \frac{\partial}{\partial x_i} \sum_j w_{kj} x_j$$

$$= (x_i - O_{xi}) - \sum_k \mu_{yk} w_{ki}$$

$$\mu_{yi} = \lambda(y_i - O_{yi}) - \sum_k \mu_{xk} \frac{\partial f_{xk}}{\partial y_i} - \sum_k \mu_{yk} \frac{\partial f_{yk}}{\partial y_i} \quad (3.42)$$

$$= \lambda(y_i - O_{yi}) - \mu_{xi} + \mu_{yi} A_i$$

$$\mu_{xi}(t) = \mu_{xi}(T) + \int_0^{T-t} (-\dot\mu_{xi}(T-u)) du \quad (3.43)$$

$$\mu_{yi}(t) = \mu_{yi}(T) + \int_0^{T-t} (-\dot\mu_{yi}(T-u)) du \quad (3.44)$$

Where $mu_i$ (T)=0 is the boundary condition.

Calculate partial derivatives and update parameters where $P_j$ is a general term for the parameters $A_j$, $B_j$, $w_{ij}$, $u_j$, $v_j$, alpha, and $\Delta t$. The correspondence can be, for instance, $P_1=A_1$, $P_2=A_2$, ... $P_N=A_N$, $P_{N+1}=B_1$, $P_{N+2}=B_2$ and so on. Learning constant varepsilon was set to 0.0001 and parameter magnitude constraint coefficient K was set to 0.0001.

$$\Delta P_j = -\varepsilon \frac{\partial L}{\partial P_j} \quad (3.45)$$

$$= \varepsilon\left(\int_0^T \sum_i \left(\mu_{xi} \frac{\partial f_{xi}}{\partial P_j} + \mu_{yi} \frac{\partial f_{yi}}{\partial P_j}\right) dt - KP_j\right)$$

$$= \varepsilon\left(\int_0^T \sum_i \mu_{yi} \frac{\partial f_{yi}}{\partial P_j} dt - KP_j\right)$$

$$\Delta A_j = \varepsilon\left(\int_0^T \sum_i \mu_{yi} \frac{\partial f_{yi}}{\partial A_j} dt - KA_j\right) \quad (3.46)$$

$$= \varepsilon\left(\int_0^T -\mu_{yj} A_j dt - KA_j\right)$$

$$\Delta B_j = \varepsilon\left(\int_0^T \sum_i \mu_{yi} \frac{\partial f_{yi}}{\partial B_j} dt - KB_j\right) \quad (3.47)$$

$$= \varepsilon \int_0^T \left(-\left(\sum_i \mu_{yi} w_{ij}\right) - KB_j\right) dt$$

$$\Delta w_{jk} = \varepsilon\left(\int_0^T \sum_i \mu_{yi} \frac{\partial f_{yi}}{\partial w_{jk}} dt - Kw_{jk}\right) \quad (3.48)$$

$$= \varepsilon\left(\int_0^T \sum_i \mu_{yi} \frac{\partial}{\partial w_{jk}} \left(\sum_l w_{il}(x_l - B_l)\right) dt - Kw_{jk}\right)$$

$$= \varepsilon\left(\int_0^T -\mu_{yj}(x_k - B_k) dt - Kw_{jk}\right)$$

$$\Delta u_j = \varepsilon\left(\int_0^T \sum_i \mu_{yi} \frac{\partial f_{yi}}{\partial u_j} st - Ku_j\right) \quad (3.49)$$

$$= \varepsilon\left(\int_0^T \mu_{yj} s(t) dt - Ku_j\right)$$

$$\Delta v_j = \varepsilon\left(\int_0^T \sum_i \mu_{yi} \frac{\partial f_{yi}}{\partial v_j} dt - Kv_j\right) \quad (3.50)$$

$$= \varepsilon\left(\int_0^T \mu_{yj} v(t) dt - Kv_j\right)$$

-continued $$\Delta \alpha = \varepsilon \left( \int_0^T \sum_i \mu_{yi} \frac{\partial f_{yi}}{\partial \alpha} dt - K\alpha \right) \quad (3.51)$$

$$= \varepsilon \left( \int_0^T (t - \Delta t) e^{-\alpha(t-\Delta t)} H^2(\alpha, \Delta t, t) \sum_i \mu_{yi} v_i dt - K\alpha \right)$$

$$\Delta(\Delta t) = \varepsilon \left( \int_0^T \sum_i \mu_{yi} \frac{\partial f_{yi}}{\partial \Delta t} dt - K\Delta t \right) \quad (3.52)$$

$$= \varepsilon \left( \int_0^T \alpha e^{-\alpha(t-\Delta t)} (-H^2(\alpha, \Delta t, t)) \sum_i \mu_{yi} v_i dt - K\Delta t \right)$$

$$\quad (3.53)$$

where $$H(\alpha, \Delta t, t) = h(\alpha, \Delta t, t) + 0.5 \quad (3.54)$$

$$= \frac{1}{1 + e^{-\alpha(t-\Delta t)}} \quad (3.55)$$

Similar equations adapted from optimal control theory were used to find parameters for the shunting model shown in Luciano, U.S. Provisional Application Ser. No. 60/041,287 filed on Mar. 20, 1997, the disclosure of which is incorporated herein by reference.

Results: Introduction and Rationale

This section and the following three sections present the results of the optimization procedure on linearly interpolated weekly data that was used to estimate parameters of a single model for each treatment group. Each patient's week zero data were used as the initial conditions for a patient-specific run of the treatment group parameterized model to see the patient-specific predicted evolution of the symptom factors. The symptom half reduction times predicted by the group-parameterized, but individually-initialized runs were then computed and the resulting numbers used in the Mann-Whitney analyses of these data. Unless otherwise noted, quantitative references to symptoms, symptom factors, or modeled symptom values (MSV) are references to model predictions and not original data.

Below in "Quantitative Fit of Model to Data" shows the correlation between the model's predicted recovery patterns and the actual recovery patterns and justifies the relevance of the Mann-Whitney U tests presented in subsequent sections. "Results: Model Choice" presents the goodness of fit statistics that justified the choice of the linear second order system over the first order (shunting) system to model the recovery pattern. "Results: Statistical Inferences" presents the differences in the treatment models obtained through statistical analysis of the half reduction times predicted by the second order model. "Results: Parameter Choice" presents the parameters obtained for the two treatment models. These treatment group optimized parameters capture the essence of the different characteristics found in the patterns of recovery for the two treatments.

Quantitative Fit of Model to Data

The second order model (discussed below) predicts aspects of the actual recovery patterns that it was not trained on, i.e., the correlation with the half reduction time. This is evidence that the model has captured some of the underlying dynamics of the individual symptoms.

The statistic for the goodness of fit of the second order model to the data was presented above, in Table 3.3. The F-statistic reported values were meant to be rough indicators of the goodness of fit and were to be taken with caution for the following three reasons: (1) the assumption of data independence is violated (because the target data were time series data and therefore not independent); (2) the data were not partitioned into disjoint training and test sets; and (3) about half of the raw data was eliminated because the half reduction time was not defined in the actual data or the model predicted symptom trajectory. As additional patient data is added to the model, the F-statistic values should gain value as indicators of goodness of fit, thus increasing the predictive value of the model.

However, notwithstanding the statistical reliability questions raised by the violation of the assumptions, the level of significance obtained was high ($p<1\times10^{-5}$) that it was enough to justify further study of the predicted recovery patterns. Below it is demonstrated that the model predictions for the value of symptom half reduction times, to which the model was blind during training (and is therefore an independent measure), is highly correlated with the half reduction times of the actual data. Therefore, in "Results: Statistics" the statistical study of half reduction times is provided.

Use of the Predicted Half Reduction Time Derived Measure

In "Results: Statistics" the half reduction time measure is used to quantify predicted aspects of the treatment dependent models. This is justified for the following two reasons. First, the fit to the data of the second order model is highly significant (shown in Table 3.3 and discussed below). Second, the half reduction times computed from the model's predictions were regressed against the half reduction times computed from the raw data to determine the relationship between them and the results indicated that they were highly correlated overall (shown in Table 3.2. Furthermore, the CBT model predicted half reduction time values versus the actual data half reduction time values are highly significant. However, the model fit to the data is not as good for DMI (see Table 3.3). In this case, the correlation of a half-reduction time and significance for DMI (shown in Table 3.2) is not significant. This suggests that the comparisons of the half reduction times between CBT and DMI, and within the DMI group, may not be directly reflected in the raw data, however, this cannot be determined without further data from recovering patients. More data is needed because in the data utilized, there were many cases where the half reduction time was not defined either because a symptom was not present or did not improve in either the raw data or the model predictions. In these cases, the half reduction time could not be used in the calculation of the correlation reported in Table 3.2.

TABLE 3.2

Predicted and Actual Symptom Half Reduction Time Statistics. Statistics were calculated between actual half reduction times from data linearly interpolated and model predicted half reduction time data. r is Pearson's correlation coefficient, $r^2$ is the proportion of variance, t is an Student's t-statistic, and p is the probability for the null hypothesis to hold.
Half Reduction Time Correlation Results

| Group | N | $r^2$ | t | p |
|---|---|---|---|---|
| CBT + DMI | 44 | 0.1955 | 3.1943 | <0.01 |
| CBT | 21 | 0.5852 | 5.1776 | <0.001 |
| DMI | 23 | 0.0515 | 1.0681 | ns |

Results: Model Choice

Qualitative Reasons for Choice of Second Order System

Referring now to FIGS. 3-9A and 3-9B, predicted patterns of recovery produced using FIG. 3-9A) the shunting and (FIG. 3-9B) the second order equations wherein the solid lines show actual patterns derived from patient clinical data and doted lines show predicted patterns. Numbers shown at the vertical axis are scaled such that the possible maximum symptom factor value yields 1.0. The plot at the bottom right in both (FIG. 3-9A) and (FIG. 3-9B) shows the error L on the ordinate axis plotted against number of training cycles on the abscissa. Note that the absolute values of the error measure L cannot be compared between shunting and second order equations, because the latter includes errors in the derivatives of L. As can be seen in FIG. 3-9A (CBT patient 1840201 MOOD) oscillatory patterns were discovered in the data.

Referring now to FIGS. 3-10A, 3-10B, 3-10C, and 3-10D which illustrates plots of individual recovery patterns with time in response to either CBT treatment or DMI treatment. Plots show patterns of recovery by symptom such as for example in FIG. 3-10A, a1 "anxiety", a2 "cognitions", a3 "mood", a4 "work", a5 "energy", a6 "early sleep", and a7 "middle and late sleep", monitored in four patients a, b, c, and d, except for a8, b8, c8, and d8 which show the error trend for each patient monitored. A solid line represents the actual pattern of recovery exhibited by a patient in response to treatment. A dotted line represents the predicted pattern of recovery. Numbers shown at the vertical axis are scaled such that possible maximum symptom factor value yields 1.0. Plots a8, b8, c8, and d8 show the error L on the ordinate axis plotted against the number of training cycles shown on the abscissa.

Plotting the patterns of recovery for individual patients who responded to either of two treatments (CBT or DMI, it was discovered that some of the recovery patterns seem to have oscillatory components. In FIG. 3-10D (DMI patient 1810101 MOOD), and (CBT patient 1800201 COGNITIONS), illustrate this. Oscillatory components can be captured naturally by second order or higher order equations. First order equations can model oscillations only by interactions among variables. Therefore, if there is an oscillation observed in one symptom factor in a first order system, there has to be another symptom factor or some covert factor, oscillating at the same rate. This type of coupled oscillation was not observed in the overt factor data.

Another observation was that a characteristic profile of activations over time in a first order shunting equation was an abrupt initial change that slowed as it approaches equilibrium, similar to an exponential decay. This was not commonly observed in clinical data. For example, mood and work factors in FIGS. 3-9A and 3-9B show exponential increase from pre-treatment to the start of treatment and exponential decrease after the start of treatment.

These qualitative observations, which are later quantitatively confirmed, resulted in the choice of a second order system. FIGS. 3-10A, 3-10B, 3-10C, and 3-10D show some examples of individual patient recovery patterns as predicted by the model using the optimized parameters. A solid line corresponds to raw weekly data. A dashed line corresponds to a prediction from the pre-treatment symptom factors and the optimized parameters. While these individual fits are rough, they captured the overall trends of the recovery patterns.

It can be seen from the graphs of patient data in FIGS. 3-10A, 3-10B, 3-10C, and 3-10D that each individual's time course of response differed greatly from another's. This made it difficult to visually evaluate the optimization process, simply by looking at the results of the parameter optimization on the individual data. As an aid in the visual assessment of the optimization, and to ensure consistency, the optimization process was also performed on the mean of the six treatment responders for each treatment group. FIGS. 3-11A and 3-11B show the time course illustrating the results of the optimization performed on CBT mean data and DMI mean data. The optimization on the mean data yielded correlation coefficients of 0.89 and 0.84 between the estimated mean symptom values and the mean data values in the CBT and DMI groups, respectively.

Statistical Reasons for Choice of Second Order System

The second order model provided a better fit to the data. The number of data points fit were 252: 6 patients times 7 symptoms times 6 weeks (6×7×6). Table 3.3 shows the F-statistics for the fits to the data for the two models. The second order model fit the data better than the first order (shunting) model for the CBT data, but the fit was roughly the same for the DMI data, with only a slight improvement with the second order model. The fits of the data were tested to determine if the fit was significantly better using the second order model by performing an R to Z transformation and then testing the difference in the z-scores obtained. The results of these tests are shown in Table 3.4, where it can be observed that in the case of the CBT data, the goodness of fit for the second order model was significantly better than the first order model. For the DMI data, the difference was not significant between the two models.

It can also be seen from the table that the second order equations showed higher correlations for CBT and approximately the same correlation for DMI data. In a separately conducted simulation which used splined data (accomplished using the cubic spline interpolation of deBoor (deBoor, C.; (1978) *A practical guide to splines*, Springer-Verlag) correlation and $L_0$ were higher for both treatments. Although not shown in the table, the pattern of statistical significance was the same. Specifically, the fit of the second order model was significantly better on the CBT data than on the DMI data, where there were no significant differences.

The second order model provides a better description of the data for both qualitative and quantitative reasons, as discussed above. Detailed results of the second order system are presented.

TABLE 3.3

F-statistic of First and Second Order Models.
F-statistic results for first order and second order systems (79 parameters). Statistics were calculated between actual data linearly interpolated and predicted data by the model. r is Pearson's correlation coefficient, $r^2$ is the proportion of variance, F is an F-statistic, and p is the probability for the null hypothesis to hold. For the calculation of the F-statistic, degrees of freedom were $(N_1, N_2) = (252, 79)$ where $N_1$ is the number of predicted weekly data and $N_2$ is the number of free parameters. $L_0$ is the sum of squares of difference between the actual data after linearly interpolation and the predicted data accumulated on a daily basis. For the simulations underlying these calculations, lambda was set to zero for the second order. This ignores errors in the first derivative allowing direct comparison of the two models

| System | F | p | $r^2$ | r | $L_0$ |
|---|---|---|---|---|---|
| Cognitive Behavioral Therapy | | | | | |
| First Order | 3.05 | $<1 \times 10^{-5}$ | 0.530 | 0.728 | 27.0 |
| Second Order | 5.36 | $<1 \times 10^{-5}$ | 0.664 | 0.815 | 17.5 |
| Desipramine | | | | | |
| First Order | 1.78 | 0.00058 | 0.397 | 0.630 | 27.2 |
| Second Order | 1.90 | 0.00016 | 0.412 | 0.642 | 24.7 |

TABLE 3.4

Result of R to Z transformation and comparison of significance of differences of the goodness of fit for the first order versus the second order systems. Subscript 1 indicates (shunting) first order system, subscript 2 indicates second order system. p is the significance as a normal deviate.
Significance of Difference of First and Second Order Models

| Treatment | N | $r_1$ | $r_2$ | $z_1$ | $z_2$ | $z_{diff}$ | statistic | p |
|---|---|---|---|---|---|---|---|---|
| CBT | 252 | 0.728 | 0.815 | 0.924 | 1.124 | 0.217 | −2.424 | 0.0152 |
| DMI | 252 | 0.630 | 0.642 | 0.741 | 0.762 | −0.020 | −0.225 | 0.8218 |

Results: Statistical Inferences
Timing of Symptom Improvement

In this section, results are presented from the studies that address timing aspects of the response patterns as predicted by the treatment models. The timing aspects are based on the derived measure half reduction time. Table 3.5 gives the mean half reduction time for each symptom by treatment. FIG. 3-12 provides graphs of these data. The half reduction times for symptoms subject to cognitive behavioral therapy (CBT) are shown in the upper portion of the figure and those for desipramine (DMI) are shown in the lower portion of the figure. The aspects that were studied were (1) a comparison of when symptoms were predicted to improve between the two treatments; (2) comparison of when symptoms were predicted improve relative to each other within a given treatment, and (3) a comparison of the temporal duration of the predicted symptom response times between the two treatments.

TABLE 3.5

Reduction Time [weeks] statistics computed from patterns generated by the optimized model.

|  | CBT | | | DMI | | |
|---|---|---|---|---|---|---|
| Symptom | mean | std | N | mean | std | N |
| Mood | 1.37 | 1.36 | 5 | 2.09 | 0.57 | 6 |
| Cognitions | 1.51 | 1.37 | 3 | 3.54 | 0.93 | 5 |
| Work | 2.21 | 0.49 | 5 | 2.67 | 1.95 | 5 |
| Anxiety | 2.57 | 0.80 | 6 | 3.74 | 3.24 | 6 |
| Energy | 2.76 | 1.06 | 6 | 2.10 | 1.48 | 6 |
| E Sleep | 4.63 | 1.32 | 3 | 2.96 | 1.82 | 5 |
| M,L Sleep | 5.04 | 1.33 | 3 | 3.89 | 1.15 | 2 |

Comparison of Response Times Between Treatments

The response times of symptoms between the two treatments were compared. A Mann-Whitney U test on half reduction times of symptoms (as predicted by the model) was performed. The results presented in Table 3.6 indicate significant differences in the response times of the mood and cognitions (sad mood, thoughts of guilt or suicide, and anxious mood) between the two treatments. For these symptoms only, the half reduction times were shorter in the patients who responded to cognitive behavioral therapy (CBT) than they were for the patients who responded to desipramine (DMI). Furthermore, as shown in Table 3.6 in CBT the mood and cognitions (sad mood, thoughts of guilt or suicide, and anxious mood) were the first symptoms to respond. There was no significant difference in the response time of the overall (50% decrease in) severity of the depressive episode for the two treatments (p=0.294).

TABLE 3.6

Mann-Whitney U Tests (two-tailed) for significant difference in symptom half reduction times of predicted patient trajectories as derived from group parameterized models. The distribution was derived by running the same treatment group model from individual-specific conditions. Half reduction times for CBT and DMI are given in days. Significance values p (two-tailed). Half reduction time [days] differences between mean CBT and DMI patients

| Symptom | Mann-Whitney U | $N_1$ | $N_2$ | p | DMI | CBT |
|---|---|---|---|---|---|---|
| Cognitions | 1 | 5 | 6 | .008 | 25 | 12 |
| Mood | 1 | 5 | 5 | .016 | 15 | 11 |
| Anxiety | 4 | 6 | 6 | .026 | 21 | 19 |
| Energy | 7 | 6 | 6 | .094 | 16 | 20 |
| Middle, Late Sleep | 4 | 4 | 5 | .190 | 28 | 36 |
| Early Sleep | 3 | 4 | 5 | .212 | 22 | 32 |
| Severity | 14 | 6 | 6 | .294 | 22 | 20[1] |
| Work | 12 | 6 | 6 | .394 | 20 | 16 |

[1]indicates that the mean was computed over all symptoms and over all patients.

These data indicate that Cognitive Behavioral Therapy acts first on mood and cognitions (sad mood, thoughts of guilt or suicide, and anxious mood). Moreover, this effect occurs significantly earlier in patients treated with CBT than in patients treated with DMI. This early response may be a result of interactions between the patient and therapist, whereby distorted cognitions, ways of thinking or interpreting events in the world, are identified, discussed, and treated. The hypothesis that desipramine may act directly and initially on the physiological factors energy/retardation is supported in the data by a trend (p<0.1).

Sequence of Symptom Improvement Within A Treatment Group

The sequence, or order in which symptoms improved, was determined by using the half reduction times that were computed for each symptom. The ascending order by CBT half reduction times for both CBT and DMI are given in Table 3.5 and shown graphically in FIG. 3-12. From FIG. 3-12 it can be seen that the order in which symptoms respond, i.e. the sequence of half reduction times are different between the two treatment groups. Significant differences in these sequences are presented in two parts. The first part (discussed above) shows that some symptoms (cognitions, mood, anxiety) improve significantly earlier in CBT than in DMI. The second part (discussed below) shows that within treatment groups there may be significant differences in the half reduction times of individual symptom factors.

In patients who responded to CBT, the symptoms improved in the following order: Mood, Cognitions, Work, Anxiety, Energy, Early Sleep, and finally, Middle and Late Sleep. By comparison, in patients who responded to DMI, the order in which symptoms was: Mood, Energy, Work, Early Sleep, Cognitions, Anxiety, Middle and Late Sleep. In both treatment patient groups, Mood was the first symptom to improve and Middle and Late Sleep was the last. The initial improvement in Mood may be due to a non-specific treatment effect, perhaps resulting from the patient participating in a research study, which could have given rise to a more hopeful outlook.

Overlap of Symptom Improvement

Referring now to FIG. 3-12, predicted mean half reduction time in weeks for seven symptoms in response to two treatments ((CBT=a) and (DMI=b)) are shown graphically. Mean half response time is shown for mood 1210 a, b; cognitive symptoms 1220 a, b; work 1230 a, b; anxiety 1240 a, b; energy 1250 a, b; early sleep 1260 a, b; and middle to late sleep 1270 a, b for each treatment respectively. The numbers at the end of each bar indicate the time in weeks predicted to be required to observe a mean half reduction time.

The time sequence of symptom improvement was studied, in order to understand whether the symptoms improved at the same time (concurrently) or one after another (sequentially). The mean half reduction time for each symptom (Table 3.5 and FIG. 3-12) is the time from the beginning of treatment until the symptom decreases to half its initial value. This was used to compare the order of symptom improvement between and within each treatment group (Table 3.7 (CBT) and Table 3.8 (DMI)).

Statistics were calculated for both the CBT and DMI groups separately. Symptom data that were not predicted to improve over the initial six week treatment period were omitted, as indicated by the fact that the number of data points N are less than the number of responders (6) in Table 3.5. Results are schematically shown in FIG. 3-13.

Results presented in Tables 3.7 and 3.8, and depicted in FIG. 3-13 are conservative. To determine the sequence of recovery, symptoms were first ordered by latency and then examined for significant differences in latency between each symptom and its nearest neighbor. Where latency differed by p<0.05 a decrease was defined. In the CBT group, there is a significant difference (p=0.052) between the half reduction time for the Energy symptom factor and the Early Sleep symptom factor, thus suggesting two distinct phases of symptom improvement. Moreover, there was also a trend (p=0.063) for another split between Cognitions (thoughts of guilt and suicide) and Work (work and interests). No significant differences were found between nearest neighbors in the DMI half reduction time sequence of symptom improvement, suggesting a concurrent improvement of symptom factors.

half reduction times of energy and early sleep disturbance. There is a trend (p<0.10 after rounding) for a split between cognitions and work in CBT responders. In DMI there were no significant differences (or trends) in the sequence.

This result suggests that the order and timing in which symptoms improve, one aspect of the recovery pattern, is different for those patients who responded CBT from the order observed in those patients who responded to DMI. This could represent a different population, or it could represent a different method of successful therapy.

The difference in recovery patterns between CBT and DMI reflect possible differences in the method of action of the different therapies. The two main differences are (1) it is

TABLE 3.7

Within group (CBT) comparison of individual patient's half reduction times as predicted by the model after training. Mann-Whitney $U$ Test was used to find significance values (p). P values reported are two tailed, (with the direction indicated in each case). If the model predicted non-improvement in the severity of a symptom, then the value was obtained by omitting these cases from the calculation and thereby reducingN to n, the reduced number of cases.
CBT Within Group Comparison of individual patient's half times.

| Symptom | Anxiety n = 6 | Cognitions n = 6 | Mood n = 5 | Work n = 6 | Energy n = 6 | E Sleep n = 4 | ML Sleep n = 5 |
|---|---|---|---|---|---|---|---|
| Anxiety | — | C < A | M < A | .588 | .394 | .126 | A < MLS |
| $N_1 = n, N_2 = n$ | | .082 | .008 | | | | .020 |
| Cognitions | | — | C < W | C < E | C < ES | C < MLS | |
| $N_1 = n, N_2 = n$ | | | .310 | .063 | .082 | .016 | .016 |
| Mood | | | — | M < W | M < E | M < ES | M < MLS |
| $N_1 = n, N_2 = n$ | | | | .004 | .004 | .018 | .016 |
| Work | | | | — | W < E | W < ES | W < MLS |
| $N_1 = n, N_2 = n$ | | | | | .064 | .018 | .010 |
| Energy | | | | | — | E < ES | E < MLS |
| $N_1 = n, N_2 = n$ | | | | | | .052 | .010 |
| E Sleep | | | | | | — | .804 |
| $N_1 = n, N_2 = n$ | | | | | | | |

TABLE 3.8

Within group (DMI) comparison of individual patient's half reduction times as predicted by the model after training. Mann-Whitney U Test was used to find significance values (p). p values reported are two tailed, (with the direction indicated in each case). If the model predicted non-improvement in the severity of a symptom, then the value was obtained by omitting these cases from the calculation and thereby reducingN to n, the reduced number of cases.
DMI Within Group Comparison of individual patient's half times.

| Symptom | Anxiety n = 6 | Cognitions n = 6 | Mood n = 5 | Work n = 6 | Energy n = 6 | E Sleep n = 4 | ML Sleep n = 5 |
|---|---|---|---|---|---|---|---|
| Anxiety | — | .310 | M < A | W < A | E < A | .172 | .930 |
| $N_1 = n, N_2 = n$ | | | .008 | .042 | .004 | | |
| Cognitions | | — | M < C | .180 | E < C | .114 | .930 |
| $N_1 = n, N_2 = n$ | | | .030 | | .042 | | |
| Mood | | | — | .330 | .792 | .190 | M < MLS |
| $N_1 = n, N_2 = n$ | | | | | | | .016 |
| Work | | | | — | .394 | .762 | .126 |
| $N_1 = n, N_2 = n$ | | | | | | | |
| Energy | | | | | — | .352 | E < MLS |
| $N_1 = n, N_2 = n$ | | | | | | | .018 |
| E Sleep | | | | | | — | .412 |
| $N_1 = n, N_2 = n$ | | | | | | | |

FIG. 3-13 diagrams the time sequence of symptom improvement. The vertical axis shows the mean half reduction time in weeks; the horizontal axis has no meaning. Symptom names are enclosed by small white ellipses and placed vertically at their mean half reduction time. Symptom names are placed vertically at their mean half reduction time. Significant difference (p<0.05 after rounding) between harder to distinguish separate groupings for DMI than for CBT, arguing for concurrent effects in DMI and sequential effects in CBT, and (2) Improvement in the cognitive symptoms (guilt and suicide) and mood tended to drive the response in the patients who responded to CBT, whereas mood improvement, energy and psychomotor retardation tended to drive the response in the DMI responsive patients. This suggests different modes of action of the two treatments.

DMI Symptom Half Reduction Times by Patient

Table 3.9 shows the average and the individual patient's half reduction times for each symptom factor as predicted by the model. Note that n is the number of symptoms the model predicts will improve by six weeks of treatment. A "---" indicates that the model predicts the symptom will not improve within the first six weeks.

TABLE 3.9

DMI Half reduction time [days] as predicted by the model. Number (n) is the number of symptoms that the model predicts will improve over the six week course, and "—" indicates a symptom that the model predicts will not improve within the first six weeks of treatment.

| Patient | Anx | Cog | Mood | Work | Energy | E Sle | ML Sle | Severity |
|---|---|---|---|---|---|---|---|---|
| 155 | 23 | 32 | 21 | 11 | 21 | 16 | 37 | 23 |
| 157 | 25 | 25 | 13 | 31 | 15 | — | 20 | 18 |
| 165 | 33 | 23 | 17 | 15 | 17 | — | 27 | 21 |
| 167 | 34 | 31 | — | 22 | 13 | 33 | 31 | 31 |
| 175 | 23 | 22 | 12 | 19 | 14 | 13 | 21 | 18 |
| 181 | 19 | 12 | 10 | 14 | 8 | 21 | — | 12 |
| Mean | 27 | 25 | 15 | 20 | 16 | 22 | 28 | 20[1] |
| Number (n) | 6 | 6 | 5 | 6 | 6 | 4 | 5 | 6 |

[1]mean computed over all symptoms and over all patients.

CBT Symptom Half Reduction Times by Patient

Table 3.10 shows the average and individual patient's half reduction times for each symptom factor as predicted by the model. Note that n is the number of symptoms the model predicts will improve by six weeks of treatment. A "---" indicates that the model predicts the symptom will not improve within the first six weeks.

TABLE 3.10

CBT Half reduction time [days] as predicted by the model. Number (n) is the number of symptoms that the model predicts will improve over the six week course, and "—" indicates a symptom that the model predicts will not improve within the first six weeks of treatment.

| Patient | Anx | Cog | Mood | Work | Energy | E Sle | ML Sle | Severity |
|---|---|---|---|---|---|---|---|---|
| 180 | 19 | 5 | 10 | 13 | 21 | 40 | — | 18 |
| 183 | 18 | 9 | 10 | 17 | 20 | 39 | 42 | 20 |
| 184 | 11 | 22 | — | 18 | 16 | 38 | 35 | 16 |
| 191 | 30 | 7 | 12 | 19 | 24 | 28 | 37 | 25 |
| 193 | 18 | — | 8 | 12 | 19 | 17 | 27 | 15 |
| 195 | 12 | 10 | 8 | 14 | 16 | — | — | 19 |
| Mean | 19 | 12 | 11 | 16 | 20 | 32 | 36 | 20[1] |
| Number (n) | 6 | 5 | 5 | 6 | 6 | 5 | 4 | 6 |

[1]mean computed over all symptoms and over all patients.

Range Score: Temporal Duration of Treatment Response

Table 3.11 shows the range scores for each patient in each studied. The range score for a patient is the interval [in days] between the half reduction time of the first symptom to improve and the half reduction time of the last symptom to improve. To determine whether the range scores were significantly different for the two treatment groups, a Mann-Whitney U test was performed. The test results are shown in Table 3.12, and indicate that the range scores were not significantly different.

Although these samples are very small there is supporting evidence to warrant further consideration. Recall that some symptoms were not predicted to have a half reduction time for some initial data. In those cases, the symptoms were omitted from the calculation. If however, instead of omitting the symptom, the missing value is substituted by the mean value over all responders from that study is substituted, the results were significant (p=0.016). Because the sample is so small, we cannot tell whether or not the two-tailed significance value of 0.132 would be significant in larger sample size and thus show the range of response times to be significantly different. While the data do suggest at least two phases in the action of CBT and only one phase in the action of DMI, no further conclusions can be drawn at present with this sample.

TABLE 3.11

CBT and DMI range scores for twelve patients who responded to CBT or DMI. Values given are the number of days between the first and last symptoms to reach their half reduction time as predicted by the model after training. Three range scores are given whose value differs only where the model predicted that a symptom would not improve. The first omits these cases from the range score and the second uses the mean.

Range Scores

| | DMI | | | CBT | |
|---|---|---|---|---|---|
| Patient | Range (omit) | Range (mean) | Patient | Range (omit) | Range (mean) |
| 155 | 26 | 26 | 180 | 35 | 35 |
| 157 | 12 | 12 | 183 | 33 | 33 |
| 165 | 18 | 18 | 184 | 27 | 27 |
| 167 | 21 | 21 | 193 | 30 | 30 |
| 175 | 11 | 11 | 193 | 19 | 19 |
| 181 | 13 | 20 | 195 | 8 | 28 |

TABLE 3.12

CBT vs DMI range scores differences. The Mann-Whitney U Test for significant difference was applied to individual patient's range scores. Significance values (p) are two tailed, (direction indicated in Response column). The difference in significance is because using the mean as a substitute for a missing half reduction value does not changeN whereas the omission of those symptoms reducesN.

CBT vs DMI Range Score Comparison

| Mann-Whitney U | $N_1$ | $N_2$ | p | Response |
|---|---|---|---|---|
| 3 | 6 | 6 | .016 | DMI < CBT (mean) |
| 8 | 6 | 6 | .132 | DMI < CBT (omitted) |

Results: Parameter Choice

This section presents the parameters obtained from the two treatment models. These parameters reveal differences in the patterns of recovery for the two treatments. Using the optimized parameters and the pre-treatment symptom factors for each patient, differences in parametric choice are discussed.

Latency and Steepness Parameters

Latency and steepness ($\Delta t$ and alpha, respectively) were optimized over all symptoms over all patients. Optimization of the second order network's latency parameter $\Delta t$ indicated a 1.2 week latency for treatment with cognitive behavioral therapy (CBT) and a 3.4 week latency for treatment with the tircyclic antidepressant drug desipramine (DMI) as shown in Table 3.13.

Steepness of onset of the delayed treatment effect (the parameter alpha in the sigmoid function) were very close to 3.0 for both CBT and DMI (Table 3.13).

TABLE 3.13

Latency [week] and steepness [week$^{-1}$] of the latent effect of treatment as predicted by the model.

| Parameter | CBT | DMI |
|---|---|---|
| Latency | 1.22 | 3.42 |
| Steepness | 3.00 | 3.01 |

The result of the optimization of the model showed that latency parameter for CBT was very small (1.2 weeks), whereas the latency parameter for DMI was much larger, 3.4 weeks. This is consistent with the well established observation {Quitkin:84, Nierenberg:91, Quitkin:93}that antidepressant drug treatments can take up to 4 weeks before they become effective. The goodness of fit was relatively insensitive to the steepness of the sigmoid function and there was little change from the initial choice of the parameter.

Treatment Intervention Parameters

The direct effects of CBT and DMI treatment interventions are shown in Tables 3.16 and 3.17, respectively. To see if the raw data suggests a significant difference in treatment effects between the two treatment groups, the improvement rates in severity (Table 3.15, ANOVA results, Table 3.14, (t-test results) after six weeks of treatment were compared. Although the rates were different for mean overall improvement in severity (39% for CBT and 57% for DMI), the difference was not statistically significant between the two treatment groups.

TABLE 3.14

Symptom factor reduction rates after six weeks of treatment for raw data. N = the number patients in which the symptom improved. If the symptom was not present, did not improve, or worsened, it was excluded from the calculations. sd = standard deviation.

| Symptom Factor | CBT | | | DMI | | | Significance level of difference (p) |
|---|---|---|---|---|---|---|---|
| | mean | sd | N | mean | sd | N | |
| Anxiety | 0.26 | 0.46 | 6 | 0.46 | 0.51 | 6 | 0.504228 |
| Cognitions | 0.51 | 0.55 | 5 | 0.57 | 0.34 | 6 | 0.151835 |
| Mood | 0.31 | 0.51 | 6 | 0.47 | 0.51 | 5 | 0.613145 |
| Work | 0.50 | 0.50 | 5 | 0.75 | 0.42 | 6 | 0.389283 |
| Energy | 0.40 | 0.24 | 6 | 0.43 | 0.50 | 6 | 0.885714 |
| E Sleep | 0.50 | 0.71 | 2 | 0.67 | 0.58 | 3 | 0.788780 |
| M. L Sleep | 0.44 | 0.10 | 3 | 0.06 | 0.65 | 6 | 0.349958 |

TABLE 3-15

Severity reduction rates after six weeks of treatment and results of ANOVA on raw data

| CBT | | DMI | |
|---|---|---|---|
| Patient # | Reduction Rate (week 6) | Patient # | Reduction Rate (week 6) |
| 180 | 0.00 | 155 | 0.50 |
| 183 | 0.59 | 157 | 0.56 |
| 184 | 0.56 | 165 | 0.52 |
| 191 | 0.04 | 167 | 0.72 |
| 193 | 0.48 | 175 | 0.52 |
| 195 | 0.68 | 181 | 0.59 |
| mean | 0.39 | mean | 0.57 |
| sd | 0.30 | sd | 0.08 |

TABLE 3-15-continued

Severity reduction rates after six weeks of treatment and results of ANOVA on raw data

| Source | SS | df | MS | F(p) |
|---|---|---|---|---|
| Treatments | 0.0963 | 1 | 0.09363 | 1.998 (0.1878) |
| Error | 0.4686 | 10 | 0.04686 | |
| Total | 0.5622 | 11 | | |

The rest of this section focuses on the differences in direct effects of treatment on symptoms observed in the optimized model parameters.

The second order weight coefficients corresponding to immediate and delayed direct effects are shown in FIG. 3–14. Immediate effects are presented at the left, delayed effects are presented at the right. In CBT, the delay itself is very small (1.2 weeks) whereas for DMI, the delay is much larger (3.4 weeks).

There are two points that should be made. First for CBT there is not much difference between direct and delayed effects on symptoms except for insomnia, whereas for DMI delayed effects are dominant for cognitions and mood. Moreover, delay for CBT is small (1.2 weeks) compared to that of DMI (3.4 weeks). This indicates that DMI works on cognition and mood at later time than CBT does. Second, effects of CBT are undifferentiated among symptoms except insomnia. Even the difference between insomnia and others disappears after 1.2 weeks. In contrast, the immediate effect of DMI is greatest on Work, and the delayed effect of DMI is greatest on Cognitions and Mood. A zero indicates that the model predicted the symptom would worsen initially.

Referring now to FIG. 3.14 which provides a graphical comparison of model's predicted (a) immediate and (b) delayed (latent) direct effects of treatment on symptoms for Cognitive Behavioral Therapy and Desipramine. A solid line represents CBT coefficient values, a dashed line represents DMI coefficient values. Symptom are represented along the x-axis. The coefficient values the parameter optimization procedure indicate the strength of the effect on the symptom at the time the effect takes place, and are placed on the y-axis. For example, the delayed effect of cognitions for desipramine occurs at 3.4 weeks with a magnitude of almost 1.5, whereas the delayed effect of cognitions of CBT takes place at 1.2 weeks and has a magnitude of about 4.2. A zero indicates that the model predicted the symptom would worsen initially.

TABLE 3.16

Coefficients of immediate and latent effects from treatment to symptoms (CBT).

| Symptom Factor | Immediate | Latent |
|---|---|---|
| Anxiety | −0.396 | −0.428 |
| Cognitions | −0.374 | −0.424 |
| Mood | −0.480 | −0.171 |
| Work | −0.538 | −0.406 |
| Energy | −0.309 | −0.262 |
| E Sleep | 0.292 | −0.289 |
| M,L Sleep | 0.273 | −0.684 |

TABLE 3.17

Coefficients of immediate and latent effects to symptoms (DMI)

| Symptom Factor | Immediate | Latent |
|---|---|---|
| Anxiety | 0.243 | −0.159 |
| Cognitions | −0.471 | −1.469 |
| Mood | −0.351 | −0.916 |
| Work | −0.752 | −0.116 |
| Energy | −0.386 | −0.236 |
| E Sleep | −0.334 | −0.229 |
| M,L Sleep | −0.115 | −0.784 |

Interaction Parameters

In analyzing the symptom interaction coefficients (see Tables 3.18 and 3.19), the first noticeable difference was in the patterns and magnitudes of the DMI interaction coefficients between the second order model and the shunting model. The second order model found stronger interactions for DMI treatment than the shunting model. This suggests that the second order system attributed simultaneous improvement to the interaction loops among symptoms.

FIGS. 3-15 and 3-16, show interactions among symptoms, together with the sequence with which the symptoms improved. In these diagrams, the weights associated with links between nodes represent the approximated total amount of change at the destination node that was directly preceded by change at the source node. These values were calculated by integrating the influence of the source value (an intervention effect or a factor) to the target value.

TABLE 3.18

Interaction coefficients among symptoms (CBT). See text for description.

| To/From | Anxiety | Cognitions | Mood | Work | Energy | E Sleep | M,L Sleep |
|---|---|---|---|---|---|---|---|
| Anxiety | −0.650 | −0.337 | 0.315 | −0.472 | 0.003 | 0.255 | −0.151 |
| Cognitions | 0.823 | −0.535 | −1.498 | −0.900 | 0.722 | 0.569 | −0.693 |
| Mood | 0.379 | −0.535 | −0.636 | −0.451 | −0.397 | −0.135 | −0.199 |
| Work | 0.179 | −0.363 | −0.580 | −0.622 | 0.112 | 0.094 | −0.286 |
| Energy | 0.416 | −0.343 | 0.635 | 0.126 | −1.613 | −0.214 | 0.101 |
| E Sleep | −0.715 | 0.341 | 0.501 | 0.063 | 0.864 | −1.023 | 0.480 |
| M,L Sleep | −1.135 | 0.318 | 0.129 | −0.402 | 1.821 | −0.048 | −0.010 |

TABLE 3.19

Interaction coefficients among symptoms (DMI). See text for description.}}

| To/From | Anxiety | Cognitions | Mood | Work | Energy | E Sleep | M,L Sleep |
|---|---|---|---|---|---|---|---|
| Anxiety | −2.980 | −0.206 | 0.931 | 0.750 | 0.276 | 1.059 | 0.336 |
| Cognitions | −0.508 | −1.095 | 0.742 | 0.129 | −0.104 | −0.445 | −0.146 |
| Mood | −1.022 | −0.048 | −0.541 | −0.373 | −0.607 | 1.030 | 0.649 |
| Work | 1.163 | 0.450 | −1.358 | −1.474 | −0.327 | 0.221 | 1.030 |
| Energy | −0.526 | −0.762 | 0.929 | 0.621 | −0.551 | −0.523 | −0.481 |
| E Sleep | 1.094 | −0.222 | −0.667 | −0.038 | 0.153 | −0.746 | −0.114 |
| M,L Sleep | −1.658 | −1.047 | 1.520 | 1.119 | −0.383 | 0.161 | −0.339 |

Tables 3.18 and 3.19 show the model's coefficients for the interactions among the symptom factors. Each column heading identifies a source symptom which acts upon a target symptom (identified by the heading of the row). The values of these tables reflect the optimized coefficients and represent the strength of the interactions among the symptoms. Negative values indicate a positive source symptom acts to improve the target symptom (by reducing it's intensity) provided that the baseline of the source symptom is negative, whereas positive values of coefficients indicate the opposite. For example, in the case of the patients who underwent DMI treatment (Table 3.19 ), the results indicate that improvement in mood tends to move in the opposite direction from the work symptom factor because of the negative sign (−). Improvement in mood also preceded improvement in work. The strength of this interaction, represented by its coefficient, was (31 1.358).

The vertical axis shown in FIGS. 3-15 and 3-16} correspond to the half reduction time [weeks]. Supra-threshold values (i.e. above 0.15) for $W_{ij}$ and $U_i$, connections among symptom factors and connecting the treatment (CBT or DMI) to each of the symptom factors, are shown in the sequence diagrams, FIGS. 3-15 and 3-16, respectively.

Cognitive Behavioral Therapy

The two main symptoms that improved during recovery in response to CBT treatment were (1) depressed mood and (2) cognitions. Anxiety and energy were also improved by the direct effects of the intervention. Improved mood was followed by an improvement in work and a further improvement in cognitions. Improvements in sleep disturbances followed the improvement (reduction) in anxiety. This is shown graphically in FIG. 3-15, where supra-threshold $W_{ij}$ and $U_i$ are shown.

Referring now to FIG. 3-15, a graphic representation of the sequence of symptom factors in recovery with Cognitive Behavioral Therapy treatment for the second order system. Vertical positions of the symptoms represent half-way-reduction time, arrows represent strong impacts and interactions, and corresponding numbers indicate the strength of the impact or interaction.

Desipramine

The weight patterns captured the covariance of the symptom improvements. For example, the weight pattern of anxiety showed that it is affected by the mood and early sleep symptom factors. Early sleep in turn receives its main input from anxiety. This implies a circular connection, or interaction between the symptom factors.

As shown in in FIG. 3-16, depressed mood, work and interests, and energy were the first symptoms to improve after the latency. Improvement in mood was followed by improvements in cognitions, middle and late sleep, and anxiety. An analysis of the coefficients in the DMI recovery model revealed more "double links" and recurrent connections than for CBT. When there are recurrent connections, as soon as one or more symptoms begin to reduce, there will be a large feedback causing the symptoms inside the loop to reduce concurrently. In the current case, anxiety and early sleep were doubly linked, and were also in a loop with depressed mood.

Referring now to FIG. 3–16, a graphic representation of the sequence of symptom factors in recovery with Desipramine treatment for the second order model is illustrated. Vertical positions of the symptoms represent halfway-reduction time, arrows represent strong impacts and interactions, and corresponding numbers indicate the strength of the impact or interaction. Dotted arrows show the interactions that operate in loops.

Additional Treatment Effects Due to Model Parameters

The damping factor (parameter $A_j$ in equation 3.6 reflects the model's tendency to slow down the speed of change of the symptom factor value. Optimized values for cognitive behavioral therapy and desipramine treatment are shown in Table 3.20. A clear finding in the baseline and the decay rate and latency parameters of the model was that the symptom factor "work" improves strongly in response to CBT treatment. This improvement was ascribed to a large immediate effect at the onset of the treatment (large negative value (−0.752) in Table 3.17. There was also a large negative self-interaction value which tends to drive the symptom to improve. The baseline (parameter $B_j$ in equation 3.6) reflects pre-treatment symptom factor values. Optimized values for cognitive behavioral therapy and desipramine treatment are shown in Table 3.21.

TABLE 3.20

Damping Factors (units of week-1)

| Symptom Factor | CBT | DMI |
| --- | --- | --- |
| Anxiety | 1.33 | 2.89 |
| Cognitions | 1.91 | 2.00 |
| Mood | 1.21 | 1.70 |
| Work | 1.28 | 2.47 |
| Energy | 1.96 | 1.66 |
| E Sleep | 1.81 | 2.09 |
| M,L Sleep | 1.30 | 1.94 |

TABLE 3.21

Baseline (pre-treatment factor values)

| Symptom Factor | CBT | DMI |
| --- | --- | --- |
| Anxiety | 0.239 | −0.324 |
| Cognitions | 0.231 | −0.668 |
| Mood | 0.380 | −0.397 |
| Work | −0.730 | −0.062 |
| Energy | 0.062 | 0.016 |
| E Sleep | −0.242 | −0.542 |
| M,L Sleep | −0.149 | 0.807 |

Limitation of Half Reduction Time Measure

The mean half reduction times of the raw data were correlated with the mean half reduction times predicted by the model. The results of the correlation, presented in Table 3.2 show that the correlation between the raw data values and the model predicted values were significant for the combined CBT and DMI treatment groups ($p<0.01$), were highly significant for the CBT treatment group ($p<0.001$), and were not significant for the DMI treatment group. While these results pose problems in interpreting the model's predictions, there is sufficient justification for believing that the half reduction times predicted by the model reflect the actual patient data. For example, the goodness of fit of the models to the data overall, are highly significant, showing that the models have predictive power for both CBT and DMI treatments. In addition, the lack of a significant correlation for DMI may be the result of deficiencies with the half reduction time measure on this data set. The half reduction time is only defined when a symptom improves and is present. Any correlation between lack of improvement in predicted and actual response for example, would result in no defined half reduction times and thus would be excluded from the computed correlation coefficient. Other measures not restricted to time recovery would not suffer from this lack of robustness when recovery is not present.

Other Limitations

The current pilot study has many technical limitations. First, this model does not distinguish transient from permanent effects of treatment. Data subsequent to the termination of treatment were not available for either study (CBT or DMI). Second, the current method only partly distinguishes the order of the recovery from of the recovery. They are distinguished in the cases where a correlation method can distinguish them. For example, assume factors A, B, and C improved in this order. We cannot tell by just looking at the sequence whether A or B independently or jointly caused the C to improve. In an attempt to differentiate sequence and causality we examined our correlation coefficients coefficients using the following logic.

In the correlation coefficient reflecting the rate of change in the improvement rate of C indicated high correlation with a low value of A (as indicated by thick arrows) but not B, it suggests that only the improvement in A caused the improvement in C. In the second order system, this can be evaluated by looking at interaction coefficients $w_{ij}$ as follows: Consider a negative interaction coefficient with a large absolute value. During the time when the value of the source is lower than the mean, the second derivative of the target tends to be negative. That reduces the first derivative of the target factor, and eventually the target factor decreases. However, the causality and correlation cannot be distinguished when the patterns of recovery of A and B are nearly identical, or when the interactions do not manifest themselves in a second differential form. A more fundamental problem exists when there is an unmeasured factor D affecting A and after some time affecting C, thus creating a false correlation from A to C. This can be teased apart only by showing that fluctuation added at A affects B but fluctuation added at B does not affect A. This type of analysis is not incorporated in the current research. Third, the current method does not incorporate stochastic analyses, which are commonly done in standard time series analysis. Incorporation of such more powerful methods requires a larger number of data than were available for the current research, and could be undertaken in future research.

Referring now to FIG. 3–17, an illustration of sequence and causal relationships among patterns of recovery is shown. Three curves (A, B, and C) in the graph show examples of hypothetical recovery patterns. Thick arrows show sequential relationships that can be captured by the current method.

There was no difference seen in overall (severity) response times.

In both groups mood was the first symptom to improve and middle/late sleep was the last.

Symptom improvement sequence clustered differently in the two treatments. The cognitive and mood symptoms (sad mood, thoughts of guilt or suicide, and anxious mood) improved significantly earlier (p<0.05, two-tailed) in CBT than DMI.

The recovery pattern for cognitive behavioral therapy tends to group into two phases with a trend of a third phase, whereas for desipramine, the recovery pattern does not group into phases. The desipramine response also shows a significant delayed effect, not found in the cognitive behavioral therapy response.

The results presented demonstrate that models of clinical recovery derived from data on different treatments predict different recovery patterns. Patterns predicted from baseline values of patients treated with cognitive behavioral therapy showed early improvement in said mood, thoughts of guilt or suicide, and anxious mood when compared to the recovery patterns predicted from the initial data of patients treated with DMI. Given that the overall severity improved at the same rate in the two groups, but the cognitive factors did not, it may be beneficial to consider a combined treatment for patients who are at a high risk for suicide, as described below.

The analyses identified which symptoms are affected and when they are affected in response to two different treatment interventions. This information could be utilized during treatment to monitor deviations from the standard time course. In the case of CBT, it may help to determine whether it is necessary for a specific symptom factor to improve before another, to identify the various stages of the recovery process in CBT. For example, to recover in work and activities, the patient may first need to show improvement in mood and depressogenic cognitions.

Implications for the Treatment of Suicidal Patients

After the onset of treatment, the duration of time required to capture change in all of the symptom factors is shorter for DMI (3.9 weeks in half reduction time) than that of CBT (5.0 weeks). However, crucial factors for suicidal patients are the cognitions (guilt and suicidal thoughts) and mood (sadness), and these factors are improved by CBT earlier (1.5 and 1.4 weeks respectively in half reduction time) in the course of treatment than they are by DMI (3.5 and 2.1 weeks). Note that the cognitions factor responded much earlier in the sequence when treated with CBT than DMI, and the cognitive symptoms (anxiety, guilt/suicide, and mood) all responded more quickly to the CBT treatment (p<0.05). This suggests that patients who report hopelessness and suicidal thoughts may benefit from either CBT alone or a combined treatment of CBT and DMI. However, this interpretation is only made with respect to moderately depressed patients in a typical out-patient sample, and is not known for severe patients or hospitalized patients. No severely suicidal patients were included in the sample and those that were had suicidal symptoms assured that they would not act on their thoughts during the study. Thus, this suggestion is speculative and awaits confirmation by further study.

Prediction of Outcome From Baseline

Two nonlinear methods are shown to both perform significantly better than multiple linear regression. Multiple linear regression is shown to perform at chance levels, while both a nonlinear neural network model and a nonlinear quadratic regression model perform at significantly above chance levels. This suggests that (1) important non-linear relationships are present in the data, and (2) the particular nonlinear method employed is not as important as its ability to model complex relationships in the data. Since quadratic regression performs about as well as backpropagation, it appears to be the interaction among variables, i.e. The nonlinearities, that are responsible for the increase in predictive performance. Consequentially, clinical researchers can use their current regression methods to reanalyze their existing data exploiting this new knowledge.

A predictive relationship (mapping) between pre-treatment symptoms, either individually or collectively, and treatment outcome was investigated. One clinical data set was utilized under each of multiple linear regression, neural network modeling, and quadratic regression to determine the predictive value of each of the aforementioned methods.

Three subproblems arose. First, the methods use different numbers of parameters and thus there was an inequity in the comparison. Second, the nonlinear methods required more parameters than the linear methods. This created problems of over-fitting in cases of sparse data. Finally, the data contained irregularities resulting from limitations of the instrument from which they were obtained.

Related Research

Problems with previous methods of analysis included: (1) the findings on outcome prediction from baseline clinical symptoms are inconclusive and sometimes inconsistent among different researchers; (2) the majority of findings resulted from analyses using only linear methods, and (3) evidence exists for nonlinear relationships between clinical variables and outcome.

The studies used to arrive at the above problems had to (1) use HDRS symptoms or severity as a potential predictor and none of the following outcome measures to have comparable dependent variables: (a) final HDRS, (b) improvement in HDRS score (c) improvement ratio in HDRS or (d) a categorical measure based on these continuous measures; and (4) use one of the following treatments to have comparable independent variables: (a) cognitive behavioral therapy; (b) desipramine; or (c) fluoxetine; (2) use short term placebo controls to show clear effects; and (3) be evenly distributed demographically (age, sex, etc.) to reduce bias in the comparison sample.

Summary of Findings

Table 4.1 summarizes reports (1986–1994) of attempts to predict outcome from baseline clinical variables. The clinical variables considered here as potential predictors of outcome were either (a) one or more of the 21 baseline HDRS individual item severity scores or (b) the baseline HDRS total severity score (overall depression severity). These clinical variables are listed in the first column of Table 4.1 under the heading Symptoms. The remainder of the columns identify the treatment administered as part of the various research studies. Each entry in Table 4.1 is an index into Table 4.2, which gives the reference. When a clinical variable was reported to be predictive of outcome (p<0.05), the number identifying the study is underline. When the clinical variable was found to be not-significant in predicting outcome, it is not underlined. A blank entry indicates that the predictive power of the clinical symptom was not reported.

Of 19 accounts in which the predictive value of severity was evaluated, 11 found it to be predictive with statistical significance. (For the purpose of maintaining readability, citations are not included in this subsection. To find references, consult Table 4.1 and Table 4.2. As for individual symptoms, 3 of 13 findings reported found depressed mood to be a predictor, 2 of 2 for late insomnia, 2 of 8 for somatic-gastrointestinal, 1 of 11 for work and interests, 2 of 14 for retardation, 2 of 12 for middle insomnia, 1 of 13 for weight change, 1 of 7 for insight, 1 of 10 for hypochondriasis, and 1 of 14 for agitation. No other independent symptoms were found to be significant predictors in the literature considered here.

Focusing on each treatment, it can be seen that: amitriptyline (Ami) increased overall severity (1 of 1), depressed mood (1 of 2), middle insomnia (1 of 1), somatic-gastrointestinal (1 of 1) and hypochondriasis (1 of 1) predicted better response; for imipramine (IMI) greater overall severity (3 of 4) predicted both better response (2 of 3) and poorer response (1 of 3), greater depressed mood (1 of 2) predicted poorer response, greater late insomnia (1 of 2), and greater retardation (1 of 3) predicted better response; for tranylcypromine (Tran) greater depressed mood, greater retardation, and greater weight change predicted better response, while greater middle insomnia and greater late insomnia predicted poorer response, (1 of 1 each, from the same paper); for electroconvulsive therapy (ECT) greater overall severity (1 of 1), greater depressed mood (1 and 1), greater work and interests (1 of 2), greater agitation (1 of 2), and greater somatic-gastrointestinal (1 of 1) predicted poorer response; for interpersonal therapy (IPT), greater overall severity predicted poorer response (1 of 1)-individual symptoms were not reported; and for maprotiline (Map) greater overall severity predicted both better and poor response (1 of 2 each), individual symptoms not reported; and for levoprotiline (Lev) greater overall severity predicted poorer response; individual symptoms were not reported (1 of 1).

Overall severity at baseline was found to be predictive throughout many treatment studies. At least one study for each treatment found overall severity at baseline to be significant except desipramine (0 of 2), clomipramine (0 of 2), fluoxetine (0 of 1), and cognitive behavioral therapy (0 of 1). However, baseline severity was not a consistent predictor of outcome, being confirmed only by 11 of 19 accounts (from thirteen studies). Much less predictive reliability at baseline was found in individual symptoms.

Severity as a Predictor

Baseline HDRS severity alone was found to be inconclusive as a predictor of general response to treatment because it was found both to be a significant predictor of response and also to not be a significant predictor of response. Examples from the literature follow.

Of thirteen studies, nineteen accounts of tests for baseline HDRS severity as a predictor of outcome were reported, eleven accounts (in seven of the studies) found baseline severity to be statistically significant Katz, M., et.al.; (1987) *Psychological Medicine* 17: 297–309; Pande, A., et.al. (1988) *Biological Psychiatry* 24: 91–93; Sotsky,S. M., et. al. (1991) *American Journal of Psychiatry*, 148: 997–1009; Vallejo, J., et. Al. (1991) *Journal of Affective Disorders*, 21: 151–162; Filip, V., et. Al, (1993). *British Journal of Psychiatry*, 163: 35–38; Hoencamp, E., et. al.; (1994) *Journal of Affective Disorders*, 31:235–246; Katon, W., et. al. (1994) *Journal of Affective Disorders*, 31: 81–90) and eight accounts (in six studies) (Kocsis, J. H., et.al. (1989) *Journal of Affective Disorders* 17: 225–260, Nagayama, H., et.al. (1991) Prediction of efficacy of antidepressants by 1-week test therapy in depression. *Journal of Affective Disorders*, 23: 213–216, Bowden, C., et.al.; (1993). *Journal of Clinical Psychopharmacology* 13: 305–311, Hinrichsen, G., et. Al. (1993) *American Journal of Psychiatry*, 150: 1820–1825, Johnson, S. L., et. Al. (1994) *Journal of Affective Disorders*, 31: 97–109, Joyce, P. R., et.al. (1994). *Journal of Afective Disorders* 30: 35–46) did not.

Of the eleven accounts that found overall severity to predict response, five found greater severity to predict better response and six found greater severity to predict poor response to treatment. Vallejo et al. (Vallejo, J., et.al. (1991) *Journal of Affective Disorders*, 21: 151–162) found the more severe the depression (baseline HDRS total), the better the outcome (percent reduction in HDRS) in a study of 116 out-patients treated with imipramine (N=89) or phenelzine (N=27), evaluated at outcome, 6 weeks (r=0.22, p=0.015) and also at a 6 month follow-up (r=0.20, p=0.029). Higher baseline HDRS severity was also found to indicate increased chance of recovery by Hoencamp et.al. (Hoencamp, E., et. al.; (1994) *Journal of Affective Disorders*, 31:235–246) in a three-phase sequential medication study (maprotiline (N=119), lithium augmentation/brofaromine (N=51), maprotiline and lithium (N=22)), (B=0.31, p<0.001).

In contrast, severity was not found to be significant when the clinical efficacy of fluoxetine and desipramine was compared in a double blind parallel group study of major depressive disorder (including both in-patients and out-patients) (Bowden, C., et.al.; (1993), *Journal of Clinical Psychopharmacology* 13: 305–311). The clinical responses of severely ill patients (those with baseline HDRS scores of 24 or greater) were compared to moderately depressed patients (those with baseline HDRS scores less than 24). No significant differences were found between the drugs when compared across severity categories and no significant differences between the two drugs were found when compared within severity categories.

Baseline severity did not significantly correlate with percent improvement or final severity score in 104 patients who participated in a study designed to examine predictors of short-term response to desipramine and clomipramine (Joyce, P. R., et.al. (1994). *Journal of Afective Disorders* 30: 35–46), and baseline severity was not found to be a significant predictor of outcome at the 4-month follow-up in patients with major depression; antidepressant treatment was not specified (Katon, W., et. al. (1994) *Journal of Affective Disorders*, 31: 81–90).

This lack of clear predictive results for severity is not surprising because severity is nonspecific with respect to symptoms. Different syndromes of equal overall severity may respond to different treatments. For example, Elkin et al. (Elkin, I., et.al. (1989) National Institue of Mental Health treatment of depression collaborative, *Archives of General Psychiatry* 46: 971–983.) was only able to find significant differential treatment response to cognitive behavioral therapy, interpersonal therapy (IPT), imipramine with clinical management and placebo with clinical management in a secondary analysis. When the population was analyzed based on baseline severity, those patients who were less severely depressed (HDRS score totals less than 20) showed no significant difference in their response to treatment. The more severely depressed (HDRS score totals greater than or equal to 20) responded best to imipramine with clinical management and worst to placebo with clinical management. Responses to CBT and IPT were in between, but closer to imipramine with clinical management, with the response to IPT better than the response to CBT.

In addition, the lack of reliability in baseline severity as a predictor of outcome could also be due to different outcome measures (see below), differences that result from treatment-specific responses, population differences, such as demographics, as well as the independent variables chosen to be tested as predictors.

Individual Symptoms as Predictors of Outcome

None of the studies that met the criteria for comparison found individual symptoms to be predictive of outcome. On the other hand, four related studies found seven symptoms to be predictive (White, K. and White, J. (1986) *Journal of Clinical Psychiatry*, 47: 380–382; Katz, M., et.al.; (1987) *Psychological Medicine* 17: 297–309; Pane, A., et.al. (1988) *Biological Psychiatry* 24: 91–93; McGrath, P. J., et.al.

(1992) *Journal of Clinical Psychopharmacology* 12: 197–202). Of these, depressed mood was the most frequent and occurred in four of the findings; middle and late insomnia occurred each occurred twice; and gastro-intestinal-somatic, work and interests, retardation, agitation, hypochondriasis, weight loss, and insight each occurred one (see Table 4.1). In addition, individual symptoms were, however, predictive of outcome in an amitriptyline study of depression Sauer et al. (Sauer, H., et.al. (1986) *International Clinical Psychopharmacology* 1: 284–295) found moderate late insomnia (p=0.035), and poor insight (p=0.025) predicted a better response whereas severe middle insomnia (p=0.031), gastrointestinal symptoms (p=0.046) and hypochondriasis (p=0.017) predict poorer response (N=50).

For example, prediction of outcome from symptoms has demonstrated in atypical depression. Atypical depression is characterized by depressions where a group of symptoms (behaviors) are the opposite of what is commonly observed in typical depressions. Features of atypical depression are oversleeping, overeating, severe lack of energy, and pathologic rejection sensitivity. McGrath (McGrath, P. J., et.al. (1992) *Journal of Clinical Psychopharmacology* 12: 197–202) showed that atypical depression patients showed a clear and consistent pattern of poorer response to imipramine.

In addition, when over-sleeping and leaden paralysis were both present, the these two symptoms (in addition to the atypical symptoms) significantly predicted less improvement with imipramine. In this example, the symptoms of atypical depression predict poor response to imipramine. The dynamics of atypical depression seem to indicate nonlinearity. No one symptom accounted the poorer response to imipramine, severity in any one of the four atypical symptoms (oversleeping, overacting, severe anergy, and pathologic rejection sensitivity) produces the effect McGrath (1992; ibid). Furthermore, the presence of more than one symptom does not increase the differential effect.

Outcome Measure

Apparent inconsistencies may be due to the outcome measure used. The findings of Filip et al., (Filip, V., et. al. (1993) *British Journal of Psychiatry*, 163: 35–38) and Popescu et al. (Popescu, C., et.al. (1993). *Roman Journal of Neurology and Psychiatry*, 31: 117–134) provide an example of (a) a case, within one study, where results are significant using one outcome measure and not significant using a different outcome measure and (b) a case where using one outcome measure the results of two studies are consistent, but using a different outcome measure their results are inconsistent. They report that baseline HDRS is predictive of outcome, i.e., when outcome is defined as final HDRS score (either levoprotiline or maprotiline, N=55, r=0.51, p<0.0002; N=108, F=5.66, p<0.01), respectively. However, when outcome is defined as percent change in HDRS, their findings are inconsistent. Filip et al. found that baseline HDRS was not a significant predictor of outcome, Popescu et.al., found that the less severe patients (those with lower baseline HDRS scores) were more likely to respond to [an unspecified] tricyclic antidepressant treatment] (N=108, F=20.12, p<0.01). Although Filip et.al. argue that the final score is most consistent with the physicians judgment, in an attempt to prevent this potential inconsistency, the results were compared to only to those results that were obtained using the same outcome measure used in the data, i.e. percent change in HDRS for the purpose of review of significant findings reported in Table 4.1.

Evidence of Nonlinearities

The specific findings are reviewed that led to the belief nonlinear relationships may exist between clinical symptoms, treatment, and outcome and therefore should be explored in the attempt to predict outcome from baseline clinical symptoms. In particular, the studies reviewed in this section suggest the presence of two different types of nonlinear relationships which may help to explain the inconclusive and sometimes inconsistent results found in the literature. The first type of nonlinear relationship would be differences observed across different treatments, indicating treatment-specific responses for subsets of symptoms. The second type of nonlinear relationship would be nonlinear relationships observed within a given treatment. Evidence for both these types of nonlinearities exist in the data. If the relationships were linear, either within or across these treatment groups, a separate linear model would be needed for each one. Using a nonlinear model, it may be possible to capture relationships in a single model given some overlap of effects. Also, a nonlinear model would be able to capture curvilinear relationships between symptoms and outcome for a given treatment.

Nonlinearities Across Treatments

When one looks at symptoms (across a row) of Table 4.1, it appears that for any given symptom, symptoms in general, i.e., symptoms independent of the treatment administered, were not found to be significant predictors of outcome. In contrast, when one looks within a given treatment (down a column), it appears that treatments may have specific symptom profiles (combinations of symptoms) that when taken together are significant predictors of outcome for that treatment.

In a treatment-specific response relationship, the treatment acts as a switch, selecting for a set of symptoms which may be different from those symptoms that another treatment might select. In a response within a given treatment, the response may indicate effective ranges of symptom severity for which the treatment is effective.

For example, looking across symptoms, we see inconsistent findings for many of the symptoms. Increase severity of depressed mood, depending on treatment, was found to positively predict outcome for tranylcypromine, to negatively predict outcome for amitriptyline, imipramine, and electroconvulsive therapy, and to not be predictive of outcome for S-adenosyl methionine, imipramine, desipramine, clomipramine, fluoxetine, and cognitive behavioral therapy. Increased severity of middle insomnia predicted poor response for amitriptyline and tranylcypromine, but not predictive of response for any other treatment reported. Increased late insomnia predicted favorable response for imipramine, poor response for tranylcypromine, and did not predict response for all other treatments reported. Greater severity in the work and interests item predicted poor response for ECT only; increased severity of retardation predicted favorable response for both imipramine and tranylcypromine; increased severity in the somatic-gastrointestinal symptom predicted poor response for only amitriptyline and ECT; increased hypochondriasis predicted poor response for tranylcypromine, and lack of insight (increased severity of insight symptom) predicted positive response for amitriptyline only. In most of the findings reported, symptoms were not predictive of outcome. When symptoms were reported to predict outcome, most were not consistent across treatments in that the same symptom predicted opposite effects.

Reports of attempts to predict outcome from baseline HDRS symptoms were focused on. Therefore, other reports showing consistent results using other instruments which were excluded from review for reasons of comparability. Thus, the entries in the table under each treatment may not be representative of the entire literature and further treatment-specific consistent patterns might be apparent with a broader survey.

In Table 4.11, it will be shown that the interaction effects of severity and thoughts of guilt and suicide (Cog.Severity), severity and anxiety (Anxiety.Severity), and severity and early sleep disturbance (ESleep,Severity) seem to be highly significant for the prediction of outcome to a heterogeneous sample of patients treated with desipramine, fluoxetine, or cognitive behavioral therapy. Furthermore, nonlinear interaction effects yield the most significant results for these data. In addition, backpropagation with treatment included in the input variables gives the most highly significant result across these data. The treatment type may select for overlapping syndromes responsive to a particular drug or psychotherapy. The interaction terms suggest different syndromes such as learned helplessness or anxious depression. Crossing the nonspecific independent variable severity with a specific symptom factor may help to identify these syndromes. We did not have the data available to validate the results, but the reports reviewed in this chapter indicate that different symptoms may predict outcome to different treatments. For example, the combination of severity, late insomnia and retardation may predict response to imipramine; the combination of depressed mood, middle and late insomnia and change in weight may predict response to tranylcypromine; and the combination of severity depressed mood, work and interests, and somatic-gastrointestinal may predict response to electroconvulsive therapy.

Nonlinearities Within Treatment Response

Nonlinearities which are induced by U-shaped relationships between symptoms and treatment response are considered herein.

Joyce et al. (Joyce, P. R. and Paykel, E. (1989) *Archives of General Psychiatry* 46: 89–99) reported that those with an intermediate level of severity respond best to treatment with tricyclic antidepressants. Thus, those with either very mild depressions or very severe depressions do not respond well, suggesting a nonlinear relationship within the tricyclic antidepressant drug family.

Furthermore, endogenous depressions have been reported to respond better to tricyclic antidepressants than nonendogenous depressions (Joyce, P. R. and Paykel, E. (1989) *Archives of General Psychiatry* 46: 89–99; Paykel, E. S. (1972) *British Journal of Psychiatry* 120: 147–156; Raskin, A. and Crook, T. A. (1976) *Psychological Medicine* 6:59–70). There are conflicting findings (Joyce P. R. And Paykel, E. (1989) *Archives of General Psychiatry* 46: 89–99; Simpson, G. M., et.al. (1976) *Archives of General Psychiatry* 33:) which could be explained by curvilinear relationships between endogenous symptoms and amitriptyline response—(Joyce, P. R. and Paykel, E. (1989) *Archives of General Psychiatry* 46: 89–99; Aboul-Saleh, M. T. And Coppen, A. (1983) *British Journal of Psychiatry*, 143: 601–603).

Neurotransmitter metabolite data from blood, urine, or plasma was not included in this study. However, Samson et al. (Samson, J. A., et. al. (1994) *Psychiatry Research* 51:157–165) found both high and low urinary 3-methoxy-4-hydroxyphenylglycol (MHPG) levels to be characteristic of late insomnia, and postulated that this may indicate a nonlinear relationship between symptoms of depression and underlying biochemical abnormalities.

The aforementioned studies suggest that the statistical significance of severity is inconsistent through the literature reviewed, however, it appears that one or more of the following reasons may be contributing factors to this inconsistency: (1) statistical effects of different populations; (2) different outcome measures; (3) comparison across treatment groups which might be selective for subpopulations with different symptom profiles but the same overall baseline HDRS severity score; (4) curvilinear relationships between independent and dependent variables. Thus, inconsistencies in the predictive value of severity appear to be largely due to differences between studies. In addition, the data summarized above suggests a consistent response to different drugs. A broader review would be necessary to substantiate these results.

METHODS

There are three categories of methods presented in this section.

The procedure used in the comparison of linear and nonlinear methods was as follows: First independent (input) was selected and dependent output) variables. These were the same seven symptom factors and severity that were used in discussed above. There were two reasons for this choice: (a) to maintain consistency with Study 1 above, which would facilitate integration of these results; and (b) the data available were too few for each of the HDRS items to be allocated separate independent variable without over-fitting the data. Next the best population distribution to assume was selected. The backpropagation algorithm and multiple linear regression was applied to the original data and to data that were rescaled based on normal, exponential, and gamma distributions. Finally, seven data sets were created, three from the individual treatment groups (CBT, DMI, and FLU), and four combinations: drug only (DMI and FLU) and all treatments (CBT, DMI, and FLU), both with and without an independent variable to indicate treatment. Also described below are the methods used to address the three subproblems mentioned above, i.e., different numbers of parameters in the models, dependent on sample size, and irregularities in the data.

The Models

Three mathematical models: neural network; multiple linear regression and quadratic regression were investigated.

Backpropagation

To evaluate the ability of a nonlinear neural network method to predict response to treatment from a set of symptoms and treatment, a network algorithm called backpropagation was chosen (Bryson, A. E. and Ho, Y.-C. (1969) *Applied Optimal Control*. Blaisdell, N.Y.; Werbos, P. J. (1974) *Beyond Regressions: New Tools for Prediction and Analysis in the Behavoiral Sciences*. Ph.D. Thesis, Harvard University; Rumelhart, D. E., et.al. (1986) *Nature* 323: 533–536). The backpropagation algorithm is based on gradient descent, which changes the weights of the network to learn a mapping between input and output vectors. A backpropagation network was chosen for the following reasons: it is a widely used and accepted neural network architecture; the software is readily available from multiple sources; and it is simple to use and relatively easy to interpret. Standard and accepted techniques were utilized in order to make the analyses easily reproducible by others.

A three layer backpropagation network model with two hidden units was used in this study. The input layer had one of four configurations (i.e. number of input nodes) dependent the data set. For all data sets without inclusion of the treatment as one of the inputs, the number of input nodes were eight. These were for the seven symptom factors and the severity of symptoms. When treatment information was included, each treatment was allocated an individual input node which would be set to either zero or one, for patient received the treatment or patient did not receive the treatment, respectively. No patient received more than one treatment in any of the three studies. Thus for the data set that combined the two drug studies, the number of input nodes were ten. The seven symptom factors, the severity, and the two additional nodes allocated to flag the treatment the patient received. The study that combined all three treatment groups had eleven input nodes. The output layer had one node, representing the response of the patient. The transformation function at the output layer was chosen to be linear, as that gave the best results. In a few instances, where noted, a logistic function was used on output. The logistic output function, being the exception, is noted when presented, and therefore, unless specified, the linear function can be assumed. The input and output representations are described in Section: Data Representation.

The threshold at the output node was set to 0.5. Activation above threshold was interpreted as predicting a responder, and activation below as predicting a non-responder. The prediction was then compared with the calculated category from the data to determine whether the network's prediction was correct.

Referring now to FIG. 4-1 nonlinear mapping of backpropagation, each hidden node finds a direction in the input space (illustrated by an arrow perpendicular to a small square piece) to which the output is sensitive to. The output of each hidden node goes through a nonlinear output function before being weighted and summed at the output node.

In the nonlinear backpropagation neural network model, the backpropagation algorithm was expected to find any subset of inputs that were predictive of the outcome and modify its connection weights in order to map their values to the predicted outcome, even when the relationship between them is nonlinear. In a backpropagation network, this is made possible in the following manner. Hidden nodes in a backpropagation network find important subspaces which are determined by input weight patterns. Output values of hidden nodes are transformed by a nonlinear function, and the degree of nonlinearity depends on the magnitude of the input weights and the size of the bias input to each hidden node. These inputs are weighted and summed at the output node, where another nonlinear output function is applied.

Regression coefficients were calculated by a standard procedure: LU decomposition with Gaussian elimination using partial pivots.

Backpropagation Training Procedure

Training a backpropagation network model involves two steps. The first adjusts model parameters which determine the behavior of the training algorithm. The second specifies the criteria for termination of training. Based on preliminary tests, the following parameter settings were chosen for all trials: the learning rates of the weight modification rules were set to 0.01 (i.e., for both input to hidden and hidden to output); the momentum, which determines the effect of the previous weight change on the current weight change, was set to 0.9; the squashing function at the output node was set to be linear; the temperature for the squashing function was set to 1; and training was terminated after 10,000 epochs. See (Hertz, J., et. al. (1991) *Introduction to the Theory of Neural Computation,* volume Lecture Notes Vol. 1 of *Sante Fe Institute Studies in the Sciences of Complexity,* Addison Wesley) for definitions of these terms within the backpropagation framework.

Linear and Quadratic Regression

The linear regression and quadratic regression analyses were carried out using the S-Plus statistical package (Statistical Sciences, 1993). The quadratic regression methods used the same regression algorithm, however, a backwards stepwise procedure, also part of the S-Plus package was used to adjust the number of parameters in the model. Quadratic regression included a new set of independent variables. The additional variables represented two-way interactions between symptoms. Then the backward stepwise regression was used to select the best model. The backwards stepwise regression procedure starts with the model that includes all variables (parameters) for each symptom and all two-way interactions. Then it systematically removes parameters that have the smallest affect on the performance of the model. This was repeated, in our case, until the model size was equal to the size of the comparison model (see below). In doing this, the linear model became nonlinear (quadratic), but the method (regression) remained unchanged.

Compensation for Different Numbers of Parameters

Different models have different numbers of parameters. This makes the comparison biased in favor of the model with more parameters; the model with more parameters will predict more of the variance in the data. To achieve equality across the different models tested we used three approaches. One approach constructed a measure of the proportion of variance explained by the model ($r^2$), proportion of variance, which was used to estimate the performance expected by chance. The second approach used the chi square and F statistics, goodness of fit statistic. These methods, explicitly and implicitly, take into account the number of free parameters in the models. The third approach used backward stepwise quadratic regression to systematically limit the number of predictive variables and thus ensure that both models had the same number of parameters for the comparison. When we compared the results to multiple linear regression, we chose a model of size 11, when compared to backpropagation, a model of size 21 was chosen. This provided an unbiased way to account for differences in performance.

Compensation for Sample Size

Another subproblem was that nonlinear methods require more data because typically they have more parameters to estimate the same predictive performance and power. More parameters mean more degree of freedom, which means more data is required to compensate for over-fitting. A combination of two approaches was used. One approach combined the data from three treatment studies, cognitive behavioral therapy (CBT), desipramine (DMI), and fluoxetine (FLU). This produced a larger data set, which typically increases the power of the model to predict outcome. The drawback of this approach is that the data are no longer homogeneous by treatment, which can obscure the results. The other approach treated each study separately. This yields more reliable results, but the smaller data sets decrease the predictive power of the model. For completeness, seven data sets of independent variables were created. Five of these consisted of treatment groups or combinations: One for each of the different treatments (CBT, DMI, FLU), one for a drug only (DMI+FLU), one for all treatments CBT+DMI+FLU). Two additional groups were created by adding a dummy variable (TxFlag) that indicated which treatment the patient received: drug with treatment flag (DMI+FLU+TxFlag) and all treatments with treatment flag (CBT+DMI+FLU+TxFlag).

Compensation for Irregularities in Data

Two different prediction algorithms, multiple regression and backpropagation were applied to each of the four sets of untransformed and transformed data on the combined data with treatment flags. This preliminary analysis indicated the exponential transformation yielded the best results for these data. Consequently, comparison of all three methods (multiple regression (MR), backpropagation (BP) and quadratic regression (QR) was completed using the exponentially transformed data. Table 4.3 shows the models and transformations.

TABLE 4.3

Three population distribution assumptions were analyzed. For each of these four data sets (one untransformed, three transformed), multivariate regression (MR) and backpropagation (BP) models were applied. The transformation that resulted in the best performance was chosen for subsequent analyses.

| Method | Transformation | | | |
|---|---|---|---|---|
| MR | Raw | Norm | Exp | Gam |
| BP | Raw | Norm | Exp | Gam |
| QR | | | Exp | |

Data Representation

This section describes the input and output data representation of the independent and dependent variables used in this study. The input data were seven symptom factors: Mood, Cognitions, Early Sleep Disturbance, Middle and Late Sleep Disturbance, Work and Interests, Energy and Retardation, and Anxiety. In addition, there was a variable for Severity, and in some instances, additional variables indicating the treatment received. In the case of the quadratic regression, input variables included some subset of those already discussed in addition to single variables representing the interaction of two symptoms.

In addition to the encoding of the data and any other transforms, such as the exponential transformation discussed in the previous section, z-score transformations were applied to both independent and dependent variables, as the last step of preprocessing.

The same symptom factors were utilized for two reasons. First, maintaining consistency with will facilitate integration of these findings later. Second, although ideally all 21 HDRS items and severity would have been analyzed, enough data ws not available to prevent over-fitting.

Input Representation

Table 4.4 identifies the input data (independent variables). It consisted of: (a) seven symptom factors derived from the twenty-one Hamilton item scores measured prior to treatment; (b) the total for the pre-treatment Hamilton scores and (c) the treatment the patient received (desipramine, fluoxetine, or cognitive behavioral therapy.)

TABLE 4.4

Independent Variables - Inputs to the models. The symptom factors and Hamilton Total are the raw (untransformed) values as represented on the HDRS scale. The values for the treatments represent binary flags indicating the treatment the patient received. Only one of the treatment flags can have the value of 1 for any given patient.

| Input Description | Raw Scale Value |
|---|---|
| Desipramine treatment | 0, 1 |
| Cognitive Behavioral Therapy Treatment | 0, 1 |
| Fluoxetine Treatment | 0, 1 |
| Symptom Factors [1 . . . 7] | 0, 1, 2, 3, 4 |
| Beginning Hamilton total | [0 . . . 65] |

Output Representation

The target output data to be predicted (the dependent variable) was the change in the severity of the symptoms after treatment. We chose the raw percent improvement (outcome) as the output since this measure is commonly reported. The computation for the outcome measure (percent change is in HDRS total) is given by $$\% \Delta HDRS = \frac{HDRS_{baseline} - HDRS_{final}}{HDRS_{baseline}} * 100 \quad (4.1)$$

where $\Delta$ HDRS is the response to treatment in terms of percent change. $HDRS_{baseline}$ is the baseline (pre-treatment) HDRS total score, and $HDRS_{final}$ is the ending (post-treatment) HDRS total score.

For DMI, the $HDRS_{final}$ value is week 6, for CBT it is week 16.

Selection of Population Distribution Function

Irregularities in the data arise from limitations of instruments of this type to account for underlying probability distribution information. The best of three normalization functions that were applied to the data were selected.

The Hamilton Depression Rating Scale, as other psychiatric scales of depression, is an ordinal scale. It consists of 21 different and independent ratings that are arbitrarily assigned a fixed numerical value (see Equation 4.1). The higher numbers on these scales represent more of a quantity; e.g., helplessness, energy, suicidal thoughts, etc. However, the numeric quantity to assign these scale values is not well defined. Typically, these numerical values are used in quantitative analysis of psychiatric data (Hamilton, M. (1960) *Journal of Neurological and Neurosurgical Psychiatry* 23: 56–62; Hamilton M. (1967) *British Journal of Social and Clinical Psychiatry* 8: 278–298; Filip, V., et. al. (1993) *British Journal of Psychiatry,* 163: 35–38). Only these values could have been used, however, a more conservative approach was taken. Statistics based on these data and assigned new scale values which are invariant with regard to the numbers assigned on the original scale were used. Such techniques are commonplace in the Statistical literature (Lehmann, E. L. (1986). *Testing statistical hypotheses.* Wiley Series in Probability and Mathematical Statistics, Wiley, New York) and have also been used by mathematical psychologists. This technique produces correct results independent of the numerical values of the HDRS items.

A derived scale was constructed from the cumulative population probability distribution of each of the HDRS items. This distribution is invariant to the underlying scale values because the cumulative population distribution for each of the items does not depend on the numbers assigned to an item. It measures the proportion of items in the population which have a score less than or equal to the given score. Functions of the distributional scores are the only invariants with regard to arbitrary monotone changes of the underlying scale (Luce, R. D., et. al. (1990) *Foundations of Measurement,* volume 1: Additive and polynomial representations. Academic Press, Inc., New York).

The cumulative distribution of each item represents a sample with a fixed distribution. Three distributions were chosen:

(1) exponential (Exp); (2) gamma (Gam); and (3) Gaussian (Norm). The parameters of the gamma and Gaussian distributions were chosen so that the means and variances coincided with the distribution of the data. The derived scale values were chosen to be the inverse of these constructed distribution functions at the HDRS item values. These derived scale values are the values of the hypothesized random variables which match the probabilities obtained from the population distribution function. This transformation removed the compression inherent near probability one of the population distribution function and constructs a theoretically motivated scale from ordinal data. The procedures used for these transformations are described in Appendix Transformations, Luciano, U.S. Prov. Pat. Applic. Ser. No. 60/041,287 filed on Mar. 20, 1997.

The original data of (N=99) input-output pairs (see Section Data Representation) were transformed to create four datasets. One remained untransformed (Raw) while three were transformed: exponential (Exp); gamma (Gam); and Gaussian (Norm). The same transformations were applied to individual scores for both pre- and post-treatment measurements. The total bb(severity) scores were calculated from the transformed values. Multiple linear regression and backpropagation were then applied to each of these four datasets. The dataset which yielded the best performance was then used in all subsequent analyses.

Preliminary analysis indicated better results with continuous outcome as the target of the prediction, i.e. (the percent change in the patient) than with predictions of categorical outcome, i.e. the patient recovered or did not recover. Most subsequent detailed analysis therefore used a continuous output measure, although some categorical results are presented below. Preliminary analysis also indicated that the exponential transformation yielded the best results for the neural network model. Consequently, the exponential transformation was used in all subsequent analysis.

Referring now to FIG. 4-2, a schematic representation of the effect of normalizing transformations on reducing nonlinearity of score-to-output relationships (or skewedness of distributions) is illustrated. In the transformation, the area under the curve is preserved. The transformation redistributes the position of the data values along the x-axis in order to preserve the areas under the curve between adjacent scores values while redistributing these data to best approximate a normal distribution. Equal areas under the curve between percentiles map to equal areas under the curve in the new distribution.

Comparison with Chance Performance

The mathematical foundation for the proportion of variance expected by chance given the number of parameters and the number of samples is approximated by dividing the number of parameters in the model by the number of samples. As an auxiliary verification of this estimation, we used S-Plus to generate random (chance) data N=99, normally distributed (mean=0, standard deviation=1) which was then used in place of the the actual data (symptom, treatment and outcome data) and then tested the predictive power of the model on these chance data. A backpropagation network with the same configuration used in the above described analysis (two hidden units) was used and trained and tested by the network on these random (chance) data. The purpose of this auxiliary test was to verify chance performance on chance data as a null hypothesis.

Interpretation of Backpropagation Weights

While it is clinically useful to be able to predict outcome, it is even more useful to know to what degree each of the symptoms contributes to the prediction. The symptoms of the backpropagation network model were ranked by influence on the response pattern. This gives a rough indication of the most important symptoms. Because backpropagation is nonlinear, a linear measure of the influence of a symptom (input variables) on the response does not exist. As a rough approximation, we assumed that the transfer functions at the neural network nodes operate in their linear ranges.

For each symptom, the influence was determined and ranked as follows:

1. The weight from the symptom (input) unit to Hidden Unit 1 was multiplied by the weight from hidden unit 1 to the output.
2. The weight from the symptom (input) unit to Hidden unit 2 was multiplied by the weight from hidden unit 2 to the output.
3. The symptom's influence is the sum of the products obtained in steps 1 and 2.

The symptoms then were ranked by their unsigned values. A threshold equal to 20% of the maximum unsigned value was computed. Symptoms that fell below this threshold were assumed to be not significant. Negative values were interpreted to inhibit a positive response or indicate nonresponse.

In this section it is concluded that the relationships between pre-treatment symptoms and outcome are nonlinear because the nonlinear methods explain more variance than the linear method, and that it is allowance for nonlinearity in the method rather than the specific nonlinear method that is important in obtaining the better results. We also show that outcome can be predicted, but weakly. The proportions of variance explained by the nonlinear models are highly significant, but low. The symptoms with the highest predictive power in these data were mood, severity, and middle and late sleep disturbances. Finally, the choice of the exponential form as a distribution function is validated.

Nonlinear Method Yields a Better Model

The performance of the linear regression and nonlinear models was compared using an r to z transformation. This method was used to determine if the correlation coefficients of the two models are significantly different from each other. Table 4.5 demonstrated that the nonlinear regression method (Backpropagation) explains significantly more of the variance in these data than the linear regression (Multiple Regression) model (p<0.0001). Therefore, the nonlinear regression method (Backpropagation) accounts for significantly more of the proportion of variance in the data than can be attributed to chance. Table 4.7 shows the significance (p<0.0001) of the goodness of fit of the backpropagation model to the full test and training set (N=99). The goodness of fit test was performed on the prediction results obtained from analysis of the full data set (N=99).

TABLE 4.5

Result of r to z transformation and comparison of significance of differences of the goodness of fit for the linear multiple regression model versus the nonlinear backpropagation model. N = 99

Comparison of Difference in Goodness of Fit

| System | r | z-score |
| --- | --- | --- |
| Multiple Regression | 0.373 | 0.392 |
| Backpropagation | 0.748 | 0.969 |
| Normal deviate | | −3.716 |
| p | | 0.0002 |

TABLE 4.6

Comparison of significance for linear and nonlinear methods. Significance values calculated using F-statistic for linear method and method based on maximum likelihood for nonlinear methods. TxFlag indicated that the data set included a flag indicating the treatment the patient received, * indicated p < 0.05, ns =not significant (and significance level was not listed in the chart), x indicates the analysis could not be performed (not enough data), ** indicates detailed analysis in text, r is Pearson's r, $r^2$ is the proportion of variance explained by the model, p was computed using the appropriate goodness of fit test.
Comparison of Goodness of Fit and Significance

| Data set (N = # Samples) | Multiple Regression (linear) $r^2$ (p <) | Backpropagation (nonlinear) $r^2$ (p <) | Quadratic Regression (nonlinear) $r^2$ (p <) |
|---|---|---|---|
| CBT (13) | .8810 (ns) | .4642 (ns) | X |
| DMI (49) | .1548 (ns) | .5685 (.005*) | .5399 (.01*) |
| FLU (37) | .1549 (ns) | .5510 (.079) | .8696 (.005*) |
| DMI + FLU (86) | .0895 (ns) | .3147 (.05*) | .4318 (.00043*) |
| DMI + FLU + CBT (99)** | .0917 (ns) | .3156 (.025*) | .3875 (.0005*) |
| DMI + FLU + TxFlag (86) | .1395 (ns) | .5601 (.0001*) | .4232 (.00081*) |
| DMI + FLU + CBT + TxFlag (99) | .1389 (ns) | .4389 (.0005*) | .4062 (.0005*) |

TABLE 4.7

Summary of results for the full training set. The table shows percent correct, Root Mean Square (RMS), and Proportion of Variance ($r^2$) for the backpropagation network with two hidden nodes. Input data were factor scores, raw or transformed using an exponential function (Exp). Output data were categorical or continuous. Momentum was 0.9, learning rate was 0.01. n/a = not applicable.

| Transformation | % correct | RMS | $r^2$ | F | p |
|---|---|---|---|---|---|
| Categorical output with logistic function at output | | | | | |
| Raw | 81.8 | 0.367 | 0.4646 | 2.2819 | 0.003013 |
| Exp | 75.8 | 0.368 | 0.4587 | 2.2284 | 0.003840 |
| Continuous-normalized output with logistic function at output | | | | | |
| Raw | n/a | 0.169 | 0.4533 | 2.1804 | 0.004770 |
| Exp | n/a | 0.113 | 0.6661 | 5.2459 | 0.000002 |

Nonlinear Methods Significantly Better Than Chance

As an auxiliary confirmation, a backpropagation was run on random data. The proportion of variance ($r^2$) obtained were slightly lower than out theoretical calculation. The $r^2$ obtained from predicting random variables was 0.2454, whereas $r^2$ expected was 0.2727. Table 4.6 shows that in all but the case of fluoxetine alone (FLU), the backpropagation model was significantly better than chance. The quadratic regression model also performed significantly better than chance. For the cognitive behavioral therapy data (CBT), it was not possible to run the quadratic regression model because there were too many parameters (21) for the number of samples (13). In all other data sets, the quadratic regression model was significantly better than chance. In contrast, the linear method performed at chance for all data sets.

Results Independent of Particular Nonlinear Model

This section shows that multiple linear regression on individual symptom factors was not significant, whereas multiple linear regression on the nonlinear data, which included symptom interaction terms, (quadratic regression) was significant. Table 4.8, shows the poor results obtained from individual symptom data alone, Table 4.9 shows the improved results from the quadratic regression model of comparable size to the backpropagation model. This suggests nonlinearities should be included either in the method or the data to improve performance, and that the improved performance is not a result of bias introduced by more parameters in one of the models.

TABLE 4.8

Multiple Regression on Combined Data - The results of multiple linear regression to predict outcome. Data were combined from three studies: (a) cognitive behavioral therapy (CBT, N = 13), desipramine (DMI, N = 49), and fluoxetine (FLU, N = 37). Proportion of Variance explained by the model, given by Pearson's $r^2$ = 0.09170485.

| Symptom | Value | Std. Error | t value | p |
|---|---|---|---|---|
| MLSleep | 2.068060e-01 | 0.1234877 | 1.674709e+00 | 0.09746297 |
| Mood | -1.142409e-01 | 0.1206277 | -9.470532e-01 | 0.34614758 |
| ESleep | 1.026300e-01 | 0.1115722 | 9.198525e-01 | 0.36010875 |
| Anxiety | 8.396366e-02 | 0.1084657 | 7.741031e-01 | 0.44089859 |
| Severity | 8.205999e-02 | 0.1578884 | 5.197341e-01 | 0.60452487 |
| Work | -3.288226e-02 | 0.1052959 | -3.122844e-01 | 0.75554676 |
| Energy | 3.182421e-02 | 0.1050965 | 3.028094e-01 | 0.76273390 |
| Cog | -1.524567e-02 | 0.1107273 | -1.376866e-01 | 0.89079566 |
| (Intercept) | -3.394970e-06 | 0.1004598 | -3.379431e-05 | 0.99997311 |

TABLE 4.9

The quadratic regression model with 21 parameters (K = 21). Data were combimed from two drug studies: (a) desipramine (DMI, N = 49) and fluoxetine (FLU, N = 37). Best fitting model of size 21 selected by a backwards stepwise procedure (Statistical Sciences, 1993) from the model including all two way interactions. Proportion of Variance explained by the model, given by Pearson's $r^2$ = 0.3874559.

| Symptom | Value | Std. Error | t value | p |
|---|---|---|---|---|
| Cog.Severity | 0.4654241 | 0.13375693 | 3.4796263 | 0.0008249741 |
| MLSleep | 0.3309996 | 0.10911044 | 3.0336204 | 0.0032811594 |
| Mood.Cog | -0.3621551 | 0.11982175 | -3.0224490 | 0.0033913402 |
| ESleep.Work | -0.2670521 | 0.09781181 | -2.7302645 | 0.0078202408 |
| Work.Anxiety | -0.3092271 | 0.11835542 | -2.6126992 | 0.0107732789 |
| ESleep.Severity | 0.4036986 | 0.17558200 | 2.2992025 | 0.0241699457 |
| (Intercept) | -0.2600431 | 0.11764378 | -2.2104278 | 0.0300061936 |
| ESleep | 0.2006639 | 0.10474988 | 1.9156477 | 0.0590747738 |
| Mood.Anxiety | -0.2122875 | 0.11095378 | -1.9132966 | 0.0593796231 |
| Anxiety.Severity | 0.3176015 | 0.16949988 | 1.8737565 | 0.0647092028 |

TABLE 4.9-continued

The quadratic regression model with 21 parameters (K = 21). Data were combimed from two drug studies: (a) desipramine (DMI, N = 49) and fluoxetine (FLU, N = 37). Best fitting model of size 21 selected by a backwards stepwise procedure (Statistical Sciences, 1993) from the model including all two way interactions. Proportion of Variance explained by the model, given by Pearson's $r^2$ = 0.3874559.

| Symptom | Value | Std. Error | t value | p |
|---|---|---|---|---|
| ESleep.Anxiety | −0.2007385 | 0.1197744 | −1.7926687 | 0.0769029771 |
| Cog.ESleep | −0.2234796 | 0.12811221 | −1.7444053 | 0.0850276002 |
| ESleep.Energy | −0.1731981 | 0.10063794 | −1.7210024 | 0.0892149166 |
| MLSleep.-Anxiety | −0.1866428 | 0.12750812 | −1.4637718 | 0.1472748574 |
| Severity | −0.1978865 | 0.14989573 | −1.3201611 | 0.1906423332 |
| Mood.MLSleep | 0.1340615 | 0.10611172 | 1.2633998 | 0.2102087949 |
| Cog.Anxiety | −0.1415459 | 0.11481283 | −1.2328404 | 0.2213381323 |
| Cog.Energy | 0.1359817 | 0.11237262 | 1.2100967 | 0.2298962726 |
| ESleep.MLSleep | −0.1350899 | 0.11977899 | −1.1278264 | 0.2628505714 |
| Mood.Severity | 0.1218931 | 0.12952479 | 0.9410797 | 0.3495695121 |
| Mood.ESleep | −0.1049684 | 0.11528845 | −0.9104852 | 0.3653717773 |

Relationships are Nonlinear

It is concluded that the relationships are nonlinear and the choice of the specific nonlinear model was not important in obtaining increased performance. This was demonstrated in two ways. First the quadratic regression model was created, which included variables for all two-way interactions between symptoms. A backward stepwise procedure was used to obtain a model of same size as the backpropagation. The results were comparable (see Table 4.10). To rule out the possibility that the increased number of parameters was responsible for all of the improved performance, we built another, quadratic regression model, this time matched with the number of parameters in the linear model. Table 4.11 shows the improved results of the linear regression with the inclusion of the interaction terms, but with a model size of the original regression on symptoms alone (i.e., without terms for symptom interactions). Table 4.10 shows the proportion of variance explained by each of the models. There was a significant improvement in the performance of linear regression model, but with variables that include the nonlinearities i.e., two way the interactions between symptoms.

TABLE 4.10

Comparison of variance explained $r^2$ for linear and nonlinear methods with different numbers of parameters. The number of parameters in the nonlinear model (QR) adjusted to 12 in order to match linear model. This removed the bias associated with more parameters. BP = backpropagation, QR = Quadratic regression. The numbers in parenthesis represent the number of parameters in the model. For BP the numbers vary with the data set and are specified with each entry. Significance levels are given for QR 11, Table 4.6 gives the significance levels for the other models.
Comparison of Explained Variance ($r^2$)

| Data set | BP $r^2$ | QR (21) $r^2$ | MR (11) $r^2$ | QR (11) $r^2$ p |
|---|---|---|---|---|
| DMI + FLU (N = 86) | .3147 (21) | .4318 | .0895 | .2913 (0.005) |
| DMI + FLU + CBT (N = 99) | .3156 (21) | .3875 | .0917 | .2736 (0.003) |
| DMI + FLU + TxFlag (N = 86) | .5601 (25) | .4232 | .1395 | .3199 (0.002) |
| DMI + FLU + CBT + TxFlag (N = 99) | .4389 (27) | .4062 | .1389 | .3095 (0.001) |

TABLE 4.11

The results of quadratic regression model with 11 parameters (K = 11). Data were combined from two drug studies: (a) desipramine (DMI, N = 49) and fluoxetine (FLU, N = 37) and included a variable that indicated which treatment the patient received. Best fitting model of size 11 selected by a backwards stepwise procedure †cite{SPLUS:93} from the model including all two way interactions. Proportion of Variance explained by the model, given by Pearson's $r^2$ = 0.3199294.

| Symptom | Value | Std. Error | t value | p |
|---|---|---|---|---|
| Cog.Severity | 0.3312666 | 0.12265150 | 2.700876 | 0.008545030 |
| ESleep.Work | −0.2829667 | 0.10499048 | −2.695165 | 0.008679468 |
| DMI | −0.2726085 | 0.10260370 | −2.656907 | 0.009630856 |
| Anxiety.Severity | 0.2325933 | 0.09678584 | 2.403175 | 0.018725709 |
| Mood.Cog | −0.2574497 | 0.10801041 | −2.383564 | 0.019677175 |
| Cog.ESleep | −0.2121521 | 0.11052312 | −1.919527 | 0.058721482 |
| MLSleep | 0.1912295 | 0.10154901 | 1.883125 | 0.063560872 |
| Work.Anxiety | −0.2283782 | 0.12188894 | −1.873658 | 0.064873109 |
| ESleep.Severity | 0.2464627 | 0.13517284 | 1.823315 | 0.072240277 |
| (Intercept) | −0.1698153 | 0.11105281 | −1.529140 | 0.130436621 |
| Mood.ESleep | −0.1566263 | 0.11703232 | −1.338317 | 0.184836384 |

Symptoms Are Weak Predicts of Response

Table 4.6 demonstrates that symptoms are significant predictors of outcome. They however are weak predictors of response because, in general, they account for less than half of the variance. A preliminary analysisis reported in which symptoms, symptom combinations, or symptom interactions, seem to be the most important in terms of their contribution to predicting the response.

The input patterns (symptom profiles) for which the network predicts the best possible represent prototypical patients. The weight coefficients that are important in the prediction also help refine the patient profile.

The column heading in Table 4.12 labeled influence indicates the contribution of each symptom (input) on the outcome (response). Table 4.12 ranks the contribution in terms of the percent change in response for each symptom factor. These results indicate that for the combined data (all three studies) Mood, Severity, and Middle and Late Sleep disturbance have the greatest influence in determining the outcome for the backpropagation method. For the regression method, the three most significant indicators were Cognitions and Severity combined, Middle and Late Sleep, and Mood and Cognitions combined. Mood, Severity, and Middle and Late Sleep disturbance appear in the top three for both methods, which may be an indication of a stronger relationship with outcome.

TABLE 4.12

Comparison of rank of independent variables (symptoms) on outcome between two nonlinear methods, backpropagation and quadratic regression. (−) indicates predicts poor outcome. The database used was CBT + DMI + FLU (no treatment flag).

Predictors of Response

| Backpropagation | | Quadratic Regression | |
| --- | --- | --- | --- |
| Symptom | Influence | Symptom(s) | p |
| Mood (−) | −32.925 | Cog.Severity | 0.0008249741 |
| Severity | 21.637 | MLSleep | 0.0032811594 |
| ML Sleep | 21.376 | Mood.Cog (−) | 0.0033913402 |
| Energy | 20.081 | ESleep.Work (−) | 0.0078202408 |
| Cognitions (−) | −13.354 | Work.Anxiety (−) | 0.0107732789 |
| Anxiety | 8.209 | ESleep.Severity | 0.0241699457 |
| E Sleep | 7.275 | (Intercept) (−) | 0.0300061936 |

Population Best Approximated to Exponential Function

Irregularities in the data that resulted from the limitations of ordinal scale instruments were minimized most when the data were compared after they were transformed by an exponential distribution function. As the ability of backpropagation to learn nonlinear mapping relies on a sufficient number of hidden nodes and nonlinearity of the nodes themselves, it is reasonable to examine the effect of the transformation in the continuous-normalized case with a logistic function at the output. Table 4.13 shows the Root Mean Square (RMS) error from worst to best for the raw data followed by each of the transformation. Note that the variances for backpropagation were smaller than those for multiple regression. The difference in RMS error is marginal when the transformation is good, i.e. when the transformation matches the underlying distribution and effectively linearizes the input data.

TABLE 4.13

Comparison of performance of multiple regression and backpropagation algorithms on data transformed to assume one of three probability distribution functions. Values given are Root Mean Squared (RMS) Error.

| Algorithm | Raw | Normal | Gamma | Exponential |
| --- | --- | --- | --- | --- |
| Multiple regression | 0.262 | 0.249 | 0.231 | 0.204 |
| Backpropagation | 0.241 | 0.215 | 0.203 | 0.198 |
| Difference | 0.021 | 0.034 | 0.028 | 0.006 |

Furthermore, backpropagation slightly outperformed multiple regression even with the best transformation method (which assumed exponential transformation as the underlying distribution). This indicates that the non-linear mapping capability of backpropagation enabled it to cope with the non-standard underlying distribution which could not be remedied by any of the transformations.

Outcome-discussion

The results indicate nonlinear methods may capture more of the information in the data then previously were captured by linear techniques. These preliminary results indicate that the data were nonlinear, that the nonlinear methods explained more of the variance in the data, and that it is the use of a nonlinear method that is important, not the particular nonlinear method. We also showed that symptoms are significant predictors of outcome. They are weak predictors in that they only explain up to about half of the variance in the data, i.e. Table 4.10 shows 42% $r^2$ explained using quadratic regression, 56% using backpropagation; and Table 4.7 shows 45% to 67% explained using backpropagation with a logistic function at the output node.

The results are promising to the clinical community as they indicate that the interactions among the symptoms of depression are important and that studying the interactions among symptoms may increase our understanding of depression. It is possible that depressive subtypes may emerge using nonlinear analysis that may not have been detectable when the focus was on individual symptoms alone.

In addition, existing data can be reanalyzed. New methods may be able to create new knowledge from existing data sets without the additional cost of clinical trials. By using the quadratic regression method described, which used multiplication of symptom severities to estimate interactions between symptoms, researchers can now reanalyze their data. This technique allows clinical researchers to use regression methods already familiar to them, which would facilitate reanalysis.

Statistically significant predictors of outcome have been found in individual studies, however the results are not consistent across studies. The nonlinear models we presented accounted for a significant proportion of variance, and so, we also were able to reject the null hypothesis, and state that performance was better than chance. We have shown that some information is being captured by the symptoms. On the other hand, there remain significant predictors of outcome yet to be discovered. Furthermore, we expect better models to result from further study. It would, of course, be better to have more data, in particular for the cognitive behavioral therapy study. Some references to methods that attempt to handle small sample sizes more effectively are presented. Notwithstanding the above, the nonlinear models' fit to the data are highly significant and can, in some cases, account for more than half of the proportion of variance in these data. Any improved theoretical model would have to capture the empirical relationships captured by the backpropagation and quadratic regression models.

Overall severity at baseline was not found to be a significant predictor of response using linear methods. Using quadratic regression, overall severity alone was not predictive of response, however, overall severity crossed with impairment in cognitions and overall severity crossed with early insomnia both predicted favorable response to cognitive behavioral therapy, desipramine and fluoxetine.

The best individual predictor of response to treatment was middle andlate sleep disturbance. Significant interaction terms were found for severity of depression crossed with severity of cognitive impairment, severity of mood crossed with severity of cognitions, severity of early sleep crossed with work inhibition, severity of anxiety crossed with work inhibition and severity of early sleep disturbance crossed with overall severity of the depressive syndrome. Bowden et al. (Bowden, C., et.al.; (1993) *Journal of Clinical Psychopharmacology* 13: 305–311) found no baseline symptoms to be predictive of outcome. Middle and late sleep disturbance have been found by others to be predictive of response to anitriptyline, imipramine and tranylcypromine, but not desipramine. There was no results reported for symptoms in Johnson et al. study of response to CBT Johnson, S. L., et. al. (1994) *Journal of Affective Disorders*, 31: 97–109). Further data would be needed to thoroughly substantiate the findings, but the results indicate that in CBT and DMI, the relationship between symptom severity and outcome is nonlinear. The inability of the nonlinear models to predict outcome may be a contributing factor to previous accounts where symptoms and severity were not found to be significant predictors of outcome for desipramine, fluoxetine, and cognitive behavioral therapy.

Effects of Scale Normalizing Transformations

The results indicated that the choice of the nonlinear method, i.e., backpropagation of quadratic regression was not important. From this it was concluded that it was reasonable to use the backpropagation algorithm to select the probability distribution function. Among different transformations, the exponential transformation resulted in the lowest errors overall. It is interesting that the exponential distribution gives the best result as a data transformation. The exponential transformation is the maximal entropy distribution with finite mean whose support is the entire positive half line (Rao, C. R. (1973). *Linear Statistical inference and its applications.* Wiley Series in probability and mathematical statistics. Wiley, New York, 2nd edition. A Wiley-Interscience publication).

The difference between the performance of the model produced by backpropagation and that produced by the linear regression method on the transformed data is that the backpropagation can process the scale dependent nonlinearities between the independent and dependent variables, whereas the linear method cannot. The linear method relies more on these data transformations than the nonlinear method and so an increase in performance is expected to be greater using the transformation (which normalizes the scale) and a method that can do this anyway. Scale dependent nonlinearities between dependent and independent variables, and backpropagation can cope with nonlinearity by itself, whereas multiple linear regression relies more heavily on transformations.

Backpropagation has the ability to learn arbitrary nonlinear mappings from inputs to outputs provided that there are enough hidden units and enough data to estimate the parameters. Put into the context of predicting outcome from symptoms, there is no need to assume linear relationships between symptoms and outcome. If there are nonlinearities, backpropagation will learn to approximate them by itself (FIG. 4.1), however it is harder, slower more error-prone, and needs more data to do so. So, preprocessing to normalize the scale is desirable.

Another way to cope with the inhomogeneous scale is to transform the input to make the mapping between the actual data and distribution assumption closer (FIG. 4.2). For example, assume that in the population (i.e. in the ideal limit) the symptom values in the underlying scale have a linear effect on the outcome, and that these values have some typical distribution such as the normal distribution. Then the nonlinearity can be thought to be caused by the non-homogeneous mapping from this ideal scale to the actual symptom scale employed. If so, the nonlinearity can be removed by transforming the symptom value in a non-homogeneous manner so that the observed distribution matches the ideal distribution and in effect becomes (or appears) linear.

Outcome—sample size

One drawback of nonlinear systems is that they require more data to extract explanatory rules. In situations, such as clinical research in depression, large sample sizes are difficult to achieve. As such, sample size is a limiting factor in training neural network models such as backpropagation. In this study, data from ninety-nine patients (combined from three studies) were available. Because these data are inherently noisy, and because backpropagation, as a rule of thumb, typically requires about ten input-output pairs per free parameter, ninety-nine input-output pairs must be considered as a small sample size, which severely restricts the network's ability to generalize. A larger sample size would be needed before the predictive capacity of baseline symptoms can be assessed using a backpropagation model.

Since the nonlinear methods necessitate larger sample sizes more data would be useful in order to further validate our model. In lieu of a larger sample size, other techniques may be useful in validating the predictive power of the nonlinear models. One next step would be to use techniques based on resampling theory. The resampling techniques use a stratified random sample, or resample the entire sample set (99 in this case) many times, instead of the conventional method for splitting the training and test set into two disjoint sets. Resampling techniques include the jackknife method and the bootstrap method (Efron, B. (1982) *The Jackknife, the bootstrap, and other resampling plans.* Society for Industrial and Applied Mathematics, Philadelphia, Pa.; Efron, B. and Tibshirani, R. (1991) *SCIENCE* 253: 390–395). In bootstrap methods, for example, the training and test sets are kept as one large sample. The training set is developed by resampling the entire set, i.e. each sample is replaced before another sample is taken. This method can be used to generate goodness of fit statistics.

Choice of Predictor Variables

Variables other than the Hamilton items may be used in the above method. Other clinical data, such as pre-treatment neurotransmitter metabolites from blood or urine, may also be used to define idealized patient profiles and idealized or standardized patterns of recovery of a patient receiving a specified treatment regime. Other forms of data such as non-invasive neuroimaging information, demographic information, family history, and genetic information may be used for their predictive capacity for establishing treatment outcome predictors.

Further, with the use of patient symptom profiles and patient symptom profiles in response to a treatment regime, where the outcome to treatment is variable based upon the currently observed patient symptoms, other disorders may be modeled using the instant invention by providing a database of known baseline symptoms and responses to treatment gathered from the clinical literature and experience to the symptom profiler, training the outcome profiler to provide idealized response patterns, and using the output from the trained outcome profiler to generate recommended treatment regimes and expected patterns of recovery for individual patients based upon the symptoms that each exhibits and the response to treatment that each exhibits. Such disorders, for example, may include AIDS and breast cancer. As with the method for the disorder described above, patient symptom information may be added to the system profiler to increase the precision of the idealized pattern generated by the symptom profiler and the outcome profiler.

The foregoing is considered only illustrative of the currently preferred embodiments of the invention presented herein. Since numerous modifications and changes will occur to those skilled in the art, it is not desired to limit the invention to the exact method or application of that method used to illustrate the embodiments comprising this invention.

What is claimed is:

1. An automated method for generating an expected recovery pattern for a patient having an affective disorder which is diagnosed and monitored, based upon patient symptoms, wherein patient response to treatment is variable, and wherein said patient exhibits at least one observed symptom, comprising:

a.) deriving a model of expected recovery patterns from individual patterns of known symptoms and known responses to at least one treatment option;

b.) providing a data system to integrate data comprising known symptoms, treatments and responses thereto, said data provided to said model, so that said model can generate a generalized expected pattern of outcome for a selected treatment when a particular pattern of symptoms is exhibited; and c.) applying said observed symptom and a proposed treatment option to said model wherein said model generates an expected recover pattern for said patient.

2. The method according to claim 1, wherein said model is non linear.

3. The method according to claim 2, wherein said model comprises a neural network.

4. The method according to claim 3, wherein said neural network has at least three layers and at least two hidden units, and wherein said at least one algorithm is a back-propagation learning algorithm.

5. The method according to claim 4, wherein said model is derived via quadratic regression.

6. The method according to claim 5, wherein said patient is exhibiting a first observed symptom and a second observed symptom, and further comprising using an independent variable in said quadratic regression, said variable representing an interaction between said first observed symptom and said second observed symptom.

7. The method according to claim 6, further comprising estimating said interaction by multiplying symptom severities.

8. The method according to claim 1, further comprising utilizing said model of expected recovery patterns to rank known symptoms by response influence to indicate the predictive importance of a particular known symptom.

9. The method according to claim 8, wherein said model is a multi-layer neural network utilizing a back propagation learning algorithm having three layers and two hidden units, and an output, and said influence of a known symptom determined by summing a first product and a second product, said first product being a first weight from said known symptom to a first hidden unit multiplied by a second weight from said first hidden unit to said output, and said second product being a third weight from said known symptom to a second hidden unit multiplied by a fourth weight from said second hidden unit to said output.

10. The method according to claim 1, further comprising: before deriving said model, providing a set of known baseline patient profiles and treatment outcomes, which known profiles and outcomes are used to derive said model.

11. An automated method of selecting a treatment regime to administer to a patient for an affective disorder which is diagnosable and treatable based upon a patient's symptoms and for which said patient could have a plurality of different patterns of response to said treatment regime, said method comprising:

a.) developing a clinical database containing clinical data from a series of historical patients diagnosed with said affective disorder, said clinical data comprising pre-treatment symptoms, treatments, and responses thereto, of said historical patients;

b.) developing a symptom profiler from said clinical data, said symptom profiler generating a known recovery pattern over time, said known recovery pattern based upon measurements of selected symptoms, said known recovery pattern associated with a selected treatment regime;

c.) developing a predictive database from said symptom profiler, said predictive database containing predicted outcomes in response to said treatment regimes;

d.) performing at least one measurement of a symptom on said patient diagnosed with said affective disorder so as to derive a baseline patient profile; and d.) applying said baseline patient profile to said symptom profiler in order to generate said treatment regime and a predicted outcome for said patient.

12. The method of claim 11, further comprising providing a model system to integrate said clinical data.

13. The method of claim 12 further comprising providing a processing unit that weights said clinical data, each unit of clinical data weighted to represent the strength of the effect of said unit of clinical data.

14. The method of claim 13, wherein each unit of clinical data has an activation value which is passed through a function to produce an output.

15. An automated system for generating an expected recovery pattern for a patient having an affective disorder which disorder is diagnosed and monitored, based upon patient symptoms, wherein patient response to treatment is variable, and wherein said patient is exhibiting at least one observed symptom, said automated system comprising a modeling system for modeling individual expected recovery patterns for individual patterns of known symptoms and known responses to at least one treatment option, to which said observed symptom and a proposed treatment option are applied, said modeling system generating an expected recovery pattern for said patient, said modeling system having a neural network architecture, said automated system comprising:

a.) an input;

b.) a network node for each symptom in a set of symptoms for said affective disorder;

c.) a delay node transfer function box to represent a latency of a response to said each treatment;

d.) an immediate response treatment pathway connected to said input and said delay node transfer function box;

e.) a latent response treatment pathway connected to said input and said delay node transfer box;

f.) a first set of uni-directional connections, having a first subset and a second subset, said connections representing an associated effect for each treatment in a set of treatment options; said first subset from said immediate response treatment pathway to said nodes and said second subset from said delay node transfer function box to said nodes; and g.) a second set of bi-directional connections between said nodes representing symptom interactions.

16. The system of claim 15, wherein each of said network nodes represents an intensity of each of said symptoms.

17. The system of claim 15 wherein said uni-directional connections are weighted to represent an intensity of each of said effects.

18. The system of claim 15 wherein said bi-directional connections are weighted in each direction to represent intensities of said symptom interactions.

19. The system of claim 15 wherein said delay node transfer function box comprises a delay node that is a sigmoid function having parameters that comprises length of delay and steepness of onset of said delayed effect.

20. The system of claim 15 wherein said immediate response treatment pathway is represented by a step function fixed to coincide with the onset of treatment.

21. An automated method for treating an affective disorder which is diagnosed and monitored, based upon symptoms experienced by a patient, wherein patient response to treatment is variable, comprising:

a.) selecting a first treatment regime for a patient who is diagnosed with said affective disorder and is exhibiting at least one observed symptom;

b.) using a recovery modeling system, for modeling expected recovery patterns for individual patterns of symptoms and responses to at lest one treatment option to generate an expected recovery pattern for said patient based upon said at least one observed symptom and said first treatment regime, said expected recovery pattern having an expected recovery time period;

c.) applying said treatment regime to said patient during said expected recovery time period and monitoring said patient to develop an actual recovery pattern; and d.) comparing said actual recovery pattern with said expected recovery pattern.

22. The method of claim 21 further comprising reevaluating said treatment regime at a time interval during said actual recovery period and if said actual recovery pattern does not correspond with said expected recovery pattern, discontinuing said first treatment regime and applying a second treatment regime.

23. The method of claim 21 wherein said modeling is non-linear.

24. The method of claim 21 wherein said modeling is non-linear, second order.

25. An automated method for developing a treatment regime for a patient having an affective disorder which is diagnosed and monitored, based upon at least one observable patient symptom, wherein patient response to treatment is variable, comprising:

a.) deriving a model of expected recovery patterns for individual patterns of known symptoms and known responses to at least one treatment option;

b.) selecting a first proposed treatment option for a patient who is diagnosed with said disorder and is exhibiting at least one observed symptom;

c.) applying said observed symptom and said first proposed treatment option to said model, wherein said model generates a first expected recovery pattern for said patient; and d.) reviewing said first expected recovery pattern in order to evaluate the suitability of said first proposed treatment option for said patient.

26. An automated method for facilitating selection of a treatment regime for an affective disorder which is diagnosed and monitored, based upon symptoms experienced by a patient, wherein the patient response to said treatment is variable, comprising:

a.) providing a modeling system;

b.) generating at least one expected recovery pattern for a patient exhibiting a particular set of symptoms, each said expected recovery pattern associated with a particular treatment option;

c.) analyzing said expected recovery patterns to determine the suitability of each associated particular treatment option for said patient; and d.) developing a treatment regime from said analysis.

27. The method of claim 26, wherein said modeling system comprises:

a.) inputting into a model a set of data comprising a plurality of individual patterns of symptoms and of individual responses to at least one treatment option; and b.) analyzing said set of data with said model to generate said expected recovery patterns.

28. The method of claim 26 wherein said modeling system comprises a non-linear second order differential equation model representing a recovery pattern by parameters indicative of a treatment intervention effect, a recovery latency, and a symptom interaction effect.

29. The method according to claim 28, wherein said non-linear second order differential equation model comprises a neural network that is trained to optimize parameter values with said parameter values adjusted through teaching so that the difference between the model output and patient data decreases.

30. The method according to claim 29, wherein said teaching comprises obtaining a set of teaching data, each said set of teaching data comprising known patient pre-treatment symptoms and recovery patterns; inputting each said set of teaching data into said neural network; and making said neural network learn each said set of teaching data.

31. The method according to claim 30 further comprising updating said teaching data to modify and update said expected recovery patterns to provide a predictive pattern of recovery for individual patterns of symptoms and responses to treatment.

32. The method according to claim 29, wherein generating said expected recovery pattern comprises:

obtaining a set of testing data from said patient, said set of testing data comprising test patient pre-treatment symptoms;

inputting said set of testing data into said neural network and obtaining therefrom an expected recovery pattern for said patient.

33. An automated method for monitoring the effectiveness of an assigned treatment for an affective disorder which is diagnosed and monitored, based upon a plurality of symptoms experienced by a patient, wherein a patient's response to said assigned treatment is variable, said method comprising:

a.) generating a profile for patient monitoring using the time series profile of progress;

b.) assessing at various time intervals; and c.) timely intervening in said treatment when said treatment is not progressing in accordance with said profile.

* * * * *